(12) United States Patent
Minor et al.

(10) Patent No.: US 11,981,948 B2
(45) Date of Patent: *May 14, 2024

(54) ARTIFICIAL ORGANELLES FOR ENZYMATIC COFACTOR REDUCTION

(71) Applicant: ENSOVI, INC., Scituate, MA (US)

(72) Inventors: Kyle A Minor, Sea Bright, NJ (US); Carlo D. Montemagno, Sutton, MA (US); David W. Wendell, Cincinnati, OH (US)

(73) Assignee: Ensovi, Inc., Scituate, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/051,969

(22) Filed: Nov. 2, 2022

(65) Prior Publication Data

US 2023/0212632 A1    Jul. 6, 2023

Related U.S. Application Data

(62) Division of application No. 17/143,755, filed on Jan. 7, 2021, now Pat. No. 11,535,880.

(Continued)

(51) Int. Cl.
*C12N 11/18* (2006.01)
*C07K 14/00* (2006.01)
(Continued)

(52) U.S. Cl.
CPC ............. *C12P 21/00* (2013.01); *C07K 14/00* (2013.01); *C07K 14/195* (2013.01); *C07K 14/245* (2013.01); *C07K 14/415* (2013.01); *C12N 9/0036* (2013.01); *C12N 11/18* (2013.01); *C12P 19/36* (2013.01); *C12Y 106/05003* (2013.01)

(58) Field of Classification Search
CPC .. C07K 14/245; C07K 14/415; C12N 9/0036; C12N 11/18; C12P 19/36; C12Y 106/05003

See application file for complete search history.

(56) References Cited

U.S. PATENT DOCUMENTS

| 2016/0281244 A1 | 9/2016 | Sato et al. |
| 2017/0113193 A1 | 4/2017 | Grezlakowski |

FOREIGN PATENT DOCUMENTS

| WO | 2011/084540 A1 | 7/2011 |

OTHER PUBLICATIONS

"NADH from Sigma" is a pdf of a webpage from Millipore Sigma accessed at https://www.sigmaaldrich.com/US/en/search/606-68-8?focus=products&page=1&perpage=30&sort=relevance&term=606-68-8&type=cas_number on Jun. 11, 2023 which has been available online since May 29, 2012 according to Google. (Year: 2012).*

(Continued)

*Primary Examiner* — David W Berke-Schlessel
*Assistant Examiner* — Trent R Clarke
(74) *Attorney, Agent, or Firm* — Michael Best & Friedrich LLP

(57) ABSTRACT

Described herein are engineered organelles comprising multi-component proteins from different species incorporated into a membrane structure with interior and exterior aspects. In one embodiment the artificial organelle incorporates one or more protein complexes that absorb optical energy and catalyze electron transfer in biochemical reactions that can be used to reduce $NAD^+$ to NADH or analogues thereof.

21 Claims, 21 Drawing Sheets
Specification includes a Sequence Listing.

Enlargement of "A" of FIG. 1B

Related U.S. Application Data

(60) Provisional application No. 62/959,001, filed on Jan. 9, 2020.

(51) Int. Cl.
| | |
|---|---|
| C07K 14/195 | (2006.01) |
| C07K 14/245 | (2006.01) |
| C07K 14/415 | (2006.01) |
| C12N 9/02 | (2006.01) |
| C12P 19/36 | (2006.01) |
| C12P 21/00 | (2006.01) |

(56) References Cited

OTHER PUBLICATIONS

Armstrong et al., "Reversibility and efficiency in electrocatalytic energy conversion and lessons from enzymes", Proc. Nat. Acad. Sci. USA, vol. 108, No. 34, 2011, pp. 14049-14054.
Belevich et al., "Activation of respiratory Complex I from *Escherichia coli* studied by fluorescent probes," Heliyon, vol. 3, No. 1, 2017, p. 28 pages.
Bezborodov et al. "Enzymatic Biocatalysis in Chemical Synthesis of Pharmaceuticals (Review)", Applied Biochemistry and Microbiology, vol. 52, No. 3, 2016 pp. 237-249.
Bridges et al., "Structure of inhibitor-bound mammalian complex I," Nature Comm., vol. 11, No. 5261, 2020, 11 pages.
Casadio, "Measurements of Transmembrane pH Differences of Low Extents in Bacterial Chromatophores—a Study with the Fluorescent-Probe 9-Amino, 6-Chloro, 2-Methoxyacridine," Eur. Biophys. J., vol. 19, No. 4, 1991, pp. 189-201.
D'Alessandro et al., "Quantitative evaluation of the intrinsic uncoupling modulated by ADP and Pi in the reconstituted ATP synthase of *Escherichia coli*," Biochimica Biophysica Acta Bioenerg., vol. 1807, No. 1, 2011, pp. 130-143.
Friedrich et al., "2 Binding-Sites for Naturally-Occurring Inhibitors in Mitochondrial and Bacterial Nadh-Ubiquinone Oxidoreductase (Complex-I)," Biochem Soc. Transact., vol. 22, No. 1, 1994, pp. 226-230.
Guo et al., "Architecture of Human Mitochondrial Respiratory Megacomplex I2III2IV2," Cell, vol. 170, No. 6, 2017, pp. 1247-1257.
Hazard et al., "Improved purification for thermophilic F1F0 ATP synthase using n-dodecyl beta-D-maltoside," Arch, Biochem Biophys., vol. 407, No. 1, 2002, pp. 117-124.
Hua et al., "Self-Directed Reconstitution of Proteorhodopsin with Amphiphilic Block Copolymers Induces the Formation of Hierarchically Ordered Proteopolymer Membrane Arrays", J Am Chem Soc, vol. 133, No. 8, 2011, pp. 2354-2357.
Kampjut et al., "The coupling mechanism of mammalian respiratory complex I," Science, vol. 370, No. 547, 2020, 13 pages.
Liang et al., "The directed cooperative assembly of proteorhodopsin into 2D and 3D polarized arrays", P Natl Acad Sci USA, vol. 104, No. 20, 2007, pp. 8212-8217.
Liang et al., "Inherently tunable electrostatic assembly of membrane proteins," Nano Let. vol. 8, No. 1, 2008, pp. 333-339.
Loll et al., "Towards complete cofactor arrangement in the 3.0 Å resolution structure of photosystem II," Nature, vol. 438, 2005, pp. 1040-1044.
Ohnishi et al., "Possible roles of two quinone molecules in direct and indirect proton pumps of bovine heart NADH-quinone oxidoreductase (complex I)," Biochimica Biophysica Acta Bioenerg., vol. 1797, No. 12, 2010, pp. 1891-1893.
Okuda et al., "Synthesis of Poly(Ethylene Glycol)-Bound NADP by Selective Modification at the 6-Amino Group of NADP", Eur. J. Biochem., vol. 151, 1985 pp. 33-38.
Parey et al., "High-resolution cryo-EM structures of respiratory complex I: Mechanism, assembly, and disease," Science Advances, vol. 5, No. 12, 2009, 10 pages.
Pryde et al. "Superoxide Is Produced by the Reduced Flavin in Mitochondrial Complex I a Single Unified Mechanism that Applies During Both Forward and Reverse Electron Transfer", Journal of Biological Chemistry, vol. 286, 2011, pp. 18056-18065.
Quinto et al., "Recent Trends in Biomimetic NADH Regeneration," Top. Catal., vol. 57, 2014, pp. 321-331.
Rigaud et al., "Reconstitution of membrane proteins into liposomes", Liposomes, Pt B 2003, vol. 372, pp. 65-86.
Sazanov et al.,"Structure of the hydrophilic domain of respiratory complex I from Thermus thermophilus," Science, vol. 311, No. 5766, 2006, pp. 1430-1466.
Seigneuret et al., "Analysis of Passive and Light-Driven Ion Movements in Large Bacteriorhodopsin Liposomes Reconstituted by Reverse-Phase Evaporation. 2. Influence of Passive Permeability and Back-Pressure Effects Upon Light-Induced Proton Uptake," Biochemistry, vol. 25, No. 21, 1986, pp. 6723-6730.
Shen et al., "Biomimetic membranes: A review," J. Memb. Sci., vol. 454, pp. 359-381, 2014.
Sheng et al., "Structural insight into light harvesting for photosystem II in green algae," Nature Plants, vol. 5, 2019, pp. 1320-1330.
Steffen et al., "Cation transport by the respiratory NADH: quinone oxidoreductase (complex I): facts and hypotheses", Biochem. Soc. Trans., vol. 41, 2013, pp. 1280-128.
Steuber et al., "Structure of the V. cholerae Na+-pumping NADH:quinone oxidoreductase," Nature vol. 516, 2014, pp. 62-67.
Su et al., "Structure and assembly mechanism of plant C2S2M2-type PSII-LHCII supercomplex," Science, vol. 357, No. 6353, 2017, pp. 815-820.
Umena et al., "Crystal structure of oxygen-evolving photosystem II at a resolution of 1.9 Å," Nature, vol. 473, 2011, pp. 55-60.
Van Bezouwen et al., "Subunit and chlorophyll organization of the plant photosystem II supercomplex," Nature Plants, vol. 3, 2017, 16 pages.
Vavilin, "Methods for the Isolation of Functional Photosystem II Core Particles from the Cyanobacterium *Synechocystis* sp. PCC 6803", in Photosynthesis Research Protocols, Second Edition, Ed. by Carpentier, Ed., 2011, vol. 684, pp. 29-40.
Verkhovskaya, "Energy-converting respiratory Complex I: On the way to the molecular mechanism of the proton pump", Int. J. Biochem. & Cell Biol., vol. 45, 2013, pp. 491-511.
Vinogradov et al., "Oxidation of NADH and ROS production by respiratory complex I," Biochimica Biophysica Acta Bioenerg., vol. 1857, No. 7, 2016, pp. 863-887.
Wei et al., "Structure of spinach photosystem II-LHCII supercomplex at 3.2 Å resolution," Nature, vol. 534, 2016, pp. 69-74.
Zhu et al., "Structure of mammalian respiratory complex I," Nature, vol. 536, 2016, pp. 354-358.
Zu et al., "Reversible, Electrochemical Interconversion of NADH and NAD+ by the Catalytic (Iλ) Subcomplex of Mitochondrial NADH:Ubiquinone Oxidoreductase (Complex I)," J. Am. Chem. Soc., vol. 125, No. 20, 2003, pp. 6020-6021.
Baradaran et al., "Crystal structure of the entire respiratory complex I", Nature, vol. 494, 2013, pp. 443-450.
Barber, "Photosystem II: a multisubunit membrane protein that oxidises water", Current Opinion in Structural Biology, vol. 12, 2002, pp. 523-530.
Brandt, "Energy Converting NADH: Quinone Oxidoreductase (Complex I)", Annu. Rev. Biochem, vol. 75, 2006, pp. 69-92.
Bricker et al., "Isolation of a highly active Photosystem II preparation from Synechocystis 6803 using a histidine-tagged mutant of CP 47", Biochimica et Biophysica Acta, vol. 1409, 1998, pp. 50-57.
Brudvig, "Water oxidation chemistry of photosystem II", Phil. Trans. R. Soc. B, vol. 363, 2008, pp. 1211-1219.
Efremov et al., "The architecture of respiratory complex I", Nature, vol. 465, 2010, pp. 441-447.
Friedrich et al., "Assembly of the Escherichia coli NADH: ubiquinone oxidoreductase (respiratory complex I)", Biochimica et Biophysica Acta, vol. 1857, 2016, pp. 214-223.
Glockner et al., "Structural Changes of the Oxygen-evolving Complex in Photosystem II during the Catalytic Cycle", The Journal of Biological Chemistry, vol. 288, No. 31, 2013, pp. 22607-22620.

(56) References Cited

OTHER PUBLICATIONS

Hsu et al., "The Two Binding Sites for DCMU in Photosystem II", Biochemical and Biophysical Research Communications, vol. 141, No. 2, 1986, pp. 682-688.
Kato et al., "Protein film photoelectrochemistry of the water oxidation enzyme photosystem II", Chem Soc Rev, vol. 43, 2014, pp. 6485-6497.
Kotlyar et al., "NADH oxidation and NAD+ reduction catalysed by tightly coupled inside-out vesicles from Paracoccus denitrificans", Eur. J. Biochem., vol. 269, 2002, pp. 4020-4024.
Kriegel et al., "Biomimetic Environment to Study *E. coli* Complex I through Surface-Enhanced IR Absorption Spectroscopy", Biochemistry, 2014, 8 pages.
Lee et al., "Coupling Photocatalysis and Redox Biocatalysis Toward Biocatalyzed Artificial Photosynthesis", ChemPubSoc Europe, vol. 19, 2013, pp. 4392-4406.
Liu et al., "Cofactor regeneration for sustainable enzymatic biosynthesis", Biotechnology Advances, vol. 25, 2007, pp. 369-384.
Mavelli et al., "The binding of quinone to the photosynthetic reaction centers: kinetics and thermodynamics of reactions occurring at the Qb-site in zwitterionic and anionic liposomes", Eur Biophys J., vol. 43, 2014, pp. 301-315.
Meyer et al., "The use of enzymes in organic synthesis and the life sciences: perspectives from the Swiss Industrial Biocatalysis Consortium", Catalysis Science and Technology, vol. 3, 2013, pp. 29-40.
Morina et al., "Engineering the Respiratory Complex I to Energy-converting NADPH: Ubiquinone Oxidoreductase", The Journal of Biological Chemistry, 2011, vol. 286, No. 40, pp. 34627-34634.
Muh et al., "Light-induced quinone reduction in photosytem II", Biochimica et Biophysica Acta, vol. 1817, 2012, pp. 44-65.
Nore, "Delta-pH Driven Energy-Linked NAD+ Reduction in Rhodospirillum rubrum Chromatophores", Archives of Biochemistry and Biophysics vol. 274, No. 1, 1989, pp. 285-289.
Ohnishi et al., "A new hypothesis on the simultaneous direct and indirect proton pump mechanisms in NADH-quinone oxidoreductase (complex I)", FEBS Letters, vol. 584, 2010, pp. 4131-4137.
Ohnishi et al., "Functional role of Coenzyme Q in the energy coupling of NADH-CoQ oxidoreductase (Complex I): Stabilization of the semiquinone state with the application of inside-positive membrase potential to proteoliposomes", BioFactors, vol. 32, 2008, pp. 13-22.
Pohl et al., "Lambda Red-Mediated Mutagenesis and Efficient Large Scale Affinity Purification of the *Escherichia coli* NADH: Ubiquinone Oxidoreductase (Complex I)", Biochemistry, vol. 46, 2007, pp. 10694-10702.
Qunito et al., "Recent Trends in Biomimetic NADH Regeneration", Top Catal, vol. 57, 2014, pp. 321-331.
Ramesh et al., "Isolation and characterization of an oxygen evolving photosystem 2 core complex from the thermophilic cyanobacterium Mastigocladus laminosus", Photosynthetic, vol. 40, No. 3, 2002, pp. 355-361.
Saito et al., "Mechanism of proton-coupled quinone reduction in Photosystem II", PNAS, vol. 110, No. 3, 2013, pp. 954-959.
Samec et al., "Theoretical Analysis of Electrochemical Reactions Involving Two Successive One-electron Transfers with Dimerization of Intermediate-Application to NAD+/NADH Redox Couple", J. Electroanal. Chem., vol. 133, 1982, 23 pages.
Selivanov et al., "Reactive Oxygen Species Production by Forward and Reverse Electron Fluxes in the Mitochondrial Respiratory Chain", PLoS Computational Biology, vol. 7, Issue 3, 2011, 17 pages.
Song et al., "Construction of Enzyme-Cofactor/Mediator Conjugates for Enhanced in Vitro Bioelectricty Generation", Bioconjugate Chemistry, 2018, vol. 29, No. 12, pp. 3993-3998.
Steffan et al., "Cation transport by the respiratory NADH: quinone oxidoreductase (complex I): facts and hypotheses", Biochemical Society Transactions, vol. 41, Part 5, 2013, pp. 1280-1287.
Trebst, "Inhibitors in the functional dissection of the photosynthetic edlectron transport system", Photosynth Res., vol. 92, 2007, pp. 217-224.
Uppada et al., "Cofactor Regeneration—an important aspect of biocatalysis", Current Science, vol. 106, No. 7, 2014, pp. 946-957.
Vinogradov, "Catalytic properties of the mitochondrial NADH-ubiquinone oxidoreductase (Complex I) and the pseduo-reversible active/inactive enxyme transition", Biochimica et Biophysica Acta, vol. 1364, 1998, pp. 169-185.
Wang et al., "Fast Isolation of Highly Active Photosystem II Core Complexes from Spinanch", J. of Integrative Plant Biology, vol. 52, No. 9, 2010, pp. 793-800.
Wu et al., "Methods for the regeneration of nicotinamide coenzymes", Green Chemistry Critical Review, vol. 15, 2013, pp. 1773-1789.
Ihara et al., "Light Driven CO2 Fixation by Using Cyanobacterial Photosystem I and NADPH-Dependent Formate Dehydrogenase", PLoS ONE, 2013, vol. 8, e71581, pp. 1-8.
Alte et al., "Ferredoxin: NADPH oxidoreductase is recruited to thylkaoids by binding to a polyproline type II helix in a pH-dependent manner", PNAS, 2010, vol. 107, No. 45, pp. 19260-19265.
International Preliminary Report on Patentability for Application No. PCT/US2021/012475 dated Jul. 12, 2022 (6 pages).
International Search Report and Written Opinion for Application No. PCT/US21/12475 dated Mar. 31, 2021 (14 pages).
Ren et al., "Cell-free Artificial Photosynthesis System", Transducers, 2017, pp. 1859-1862.
Nace, "The Photosynthesis Equation Made Easy", Forbes Science, <https://www.forbes.com/sites/trevornace/2019/08/26/the-photosynthesis-equation-made-easy/?sh=117f2a8b200e>, Aug. 2019, 3 pages.
Canadian Patent Office Action for Application No. 3,163,610 dated Jun. 23, 2023 (5 pages).
European Patent Office Extended European Search Report for Application No. 21738134.2, dated Dec. 21, 2023 (8 pages).
Wang, G. et al.. "Light-driven biocatalysis in liposomes and polymersomes: where are we now ?. " Catalysts 9.1 (2018): 12.
Lee, K.Y., et al. "Photosynthetic artificial organelles sustain and control ATP-dependent reactions in a protocellular system." Nature biotechnology 36.6 (2018): 530-535.
Feng, X., et al. "Coassembly of photosystem II and ATPase as artificial chloroplast for light-driven ATP synthesis." ACS nano 10.1 (2016): 556-561.

\* cited by examiner

Enlargement of "A" of FIG. 1B

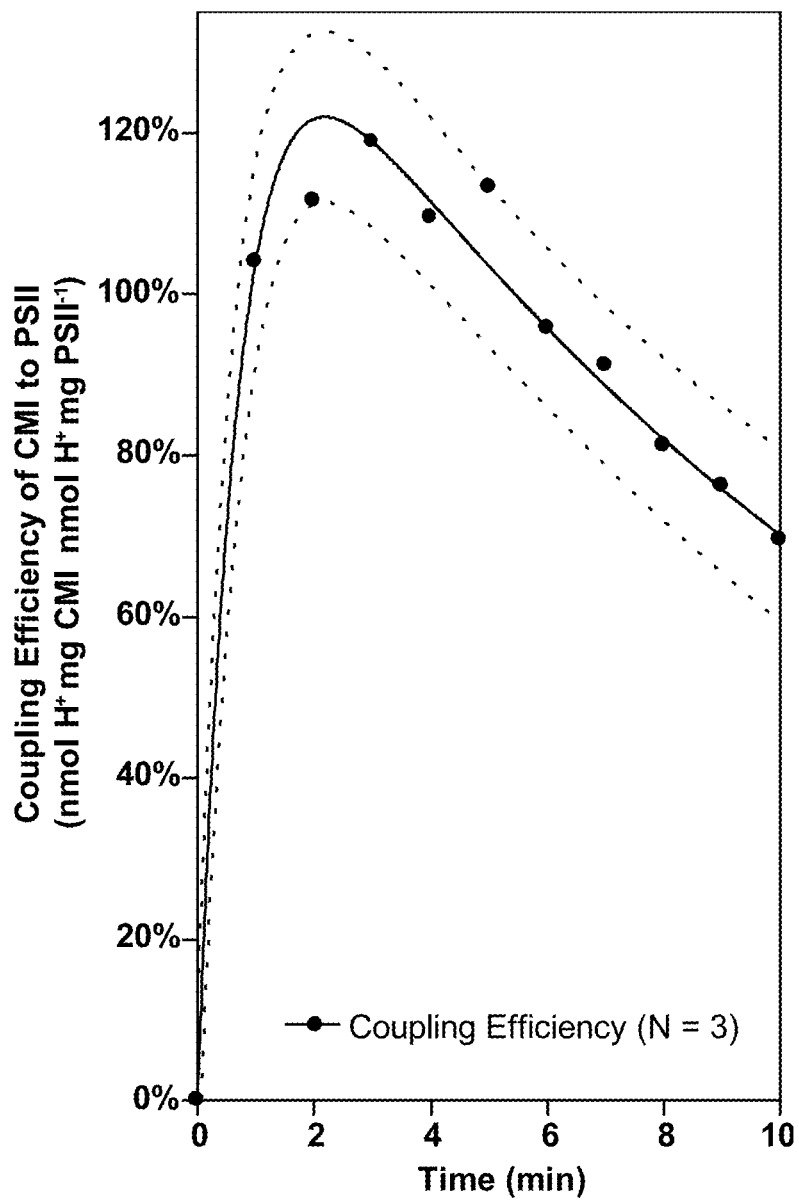

ARTIFICIAL ORGANELLES FOR ENZYMATIC COFACTOR REDUCTION

CROSS-REFERENCE TO RELATED APPLICATIONS

This application is a divisional of U.S. patent application Ser. No. 17/143,755, filed Jan. 7, 2021, which claims priority to U.S. Provisional Patent Application No. 62/959,001, filed on Jan. 9, 2020, each of which is incorporated by reference herein in its entirety.

REFERENCE TO SEQUENCE LISTING

This application was filed with a Sequence Listing XML in ST.26 XML format in accordance with 37 C.F.R. § 1.831. The Sequence Listing XML file submitted in the USPTO Patent Center, "217297-9001-US03_sequence_listing_xml 27 Mar. 2023.xml," was created on Mar. 27, 2023, contains 34 sequences, has a file size of 36.7 Kbytes, and is incorporated by reference herein in its entirety.

TECHNICAL FIELD

Described herein are engineered organelles comprising multi-component proteins from different species incorporated into a membrane structure with interior and exterior aspects. In one embodiment the artificial organelle incorporates one or more protein complexes that absorb optical energy and catalyze electron transfer in biochemical reactions that can be used to reduce $NAD^+$ to NADH or analogues thereof.

BACKGROUND

Regeneration of enzymatic cofactors is a significant technical hurdle preventing the widespread employment of biochemical synthetic reactions as a production process for fine chemical manufacturing. The high cost of the continual replacement of enzymatic cofactors limits the economic viability of this production methodology despite potentially significant improvements in product quality and an associated reduction in environmental impact.

Oxidoreductase enzymes currently are employed for over 50% of the consumer chemicals manufactured using biocatalysts. Of the known oxidoreductase enzymes, 80% require Nicotinamide coenzymes ($NAD^+$/NADH or $NADP^+$/NADPH). This makes nicotinamide coenzymes the most frequently used cofactors for consumer chemicals that are manufactured using biocatalysts [1]. Commonly, the cost of such cofactors significantly exceeds the product value. As a result, the high cost of these cofactors prohibits the use of redox enzymatic reactions in industrial applications. To make any industrial biosynthesis process that uses oxidoreductase enzymes economically feasible the consumed cofactors must be efficiently regenerated.

NADH regeneration technologies have made numerous advances in recent decades [2]. The most adopted technology by industry is the enzymatic regeneration of NADH. However, current enzymatic methods are technically difficult to execute making them unsuitable for biosynthetic transformations. These methods require a suitable enzyme to couple to the co-substrate, the engineering of an efficient separation strategy and to designing a rational reaction route [2-5]. Moreover, these methods require excess amounts of sacrificial electron donors (e.g., 1,4-butanediol, ethanol, isopropanol); the corresponding products are discarded as waste, and many produce $CO_2$.

Natural photosynthesis has exceptional features; quantum yields near unity and environmental compatibility that scientists have strived to mimic. Attempts at constructing a photobioreactor through the pairing of a biocatalysis cycle with photocatalysis, despite their progression over recent years, still pale in comparison to the efficiency found in nature [6]. Many of these technologies fail to provide the oxidation power necessary to oxidize water (1.3 V).

NADH:ubiquinone oxidoreductase (Complex I) is the first enzyme of the respiratory chain in both bacteria and mitochondria. There are three types of Complex I which are currently known: $H^+$ or $Na^+$ ion-translocating Complex I ($NDH^{-1}$ in bacterial), $Na^+$ ion-translocating Complex I ($Na^+$-NQR), and the non-electrogenic Complex I (NDH-2) found in both prokaryotes and eukaryotes [7]. The basic properties of Complex I and its function are common to both prokaryotic and eukaryotic variants [8].

The crystal structure of the entire Complex I from *Thermus thermophilus* was recently solved [9]. The prokaryotic NDH-1 is comprised of 16 subunits containing seven $Fe_4S_4$ and two $Fe_2S_2$ iron-sulfur clusters and one bound falvin mononucleotide (FMN) with an aggregate molecular weight of 536 kDa [9]. The enzyme is divided into two major domains: the membrane bound and aqueous domains, the latter of which stands tangent to the membrane bound embedded portion giving it a L-shaped structure [10]. NDH-1 is comprised of three specialized modules: (1) The hydrophilic NADH oxidizing/reducing module (N-module); (2) the hydrophobic module responsible for proton transport (P-Module); and (3) a Q-binding domain connecting the other two modules (Q-module).

The primary role of Complex I is the catalytic transfer of two electrons through oxidation of NADH produced in catabolic pathways into the respiratory chain [10]. It is a vectorial proton pump driven by electron transfer, moving protons from the positively charged to the negatively charged side of the membrane during forward electron transport. Upon binding NADH, electrons are transferred to the bound flavin mononucleotide (FMN) and passed through seven iron-sulfur (Fe—S) clusters to reduce ubiquinone (Q) [11]. The reduced form of Q, $QH_2$ acts as a reducing agent for subsequent enzymes in the respiratory system. Coupled with the electron transfer, four protons are transported into the periplasm, assisting in the generation of the proton motive force (PMF) used for driving ATP synthase [12].

It has been reported that Complex I is a reversible machine which can utilize the proton motive force for the reduction of NAD± to NADH [13-14]. It has been reported that proton motive force-dependent electron transport can occur reducing NADH through $QH_2$. In this process Q is reduced through the oxidation of succinate by membrane bound succinate dehydrogenase [15-16].

Photosystem II (PSII) from oxygenic phototrophs is a multi-subunit pigment-protein, transmembrane protein [17]. It is embedded in the thylakoid membrane of cyanobacteria, higher plants, and algae [18]. Functioning as a light-driven Water:Quinone oxidoreductase, its primary function is charge generation. PSII is the first protein complex in the photosynthesis chain. PSII harvests solar energy producing a charge separation catalyzing the splitting of water, extracting electrons, producing $O_2$ and protons contributing to the PMF for ATP synthesis [19]. The function of PSII is highly conserved across species and between kingdoms. See e.g., Thornton et al. at 122 [20].

The primary photochemical reaction takes place within the reaction center (RC), the core of PSII. The RC is comprised of two protein subunits D1 and D2. Bound to the RC are CP43 and CP47 proteins, which are responsible for the adsorption of light energy [21]. The excitation energy adsorbed by these pigment-containing proteins is transferred to the RC [22]. These subunits contain all the cofactors involved in photochemical charge separation, Q-reduction, and the oxidation of water [22]. To drive these reactions 680 nm photons are adsorbed by P680, the primary oxidant of PSII. There are four chlorophyll a (Chla) molecules and two pheophytin a (Pheo$_{D1}$/Pheo$_{D2}$) molecules, which form P680. Excitation of P680 promotes a number of electron transfer reactions [23].

Upon excitation of a Chla, P680 is converted to a strong reducing agent P680*. Very rapidly, a Pheo molecule is reduced by P680* forming a radical pair state P680*$^-$ Phe*$^-$. Within a few picoseconds Pheo*-reduces a plastoquinone (Q$^A$) molecule tightly bound to the D2 domain producing P680*$^-$PheoQ$_A^-$. With a redox potential >1 V, P680*$^+$ oxidizes a tyrosine residue (Yz) located in the D1 domain within nanoseconds, forming Y$_z$*$^+$P680PheoQA$^-$. The Y$_z$*$^+$ P680PheoQ$_A^-$ complex is responsible for the reduction of a second plastoquinone (QB) within the D1 protein forming Y$_z$*$^+$P680PheoQ$_A$Q$_B^-$. The oxidized tyrosine extracts an electron and a proton from one of four manganese atoms in the oxygen evolving complex (Mn$_4$CaO$_5$) ligated to the D1 and CP43 subunits [24]. This entire process is repeated to reduce Q$_B^-$ to Q$_B^{-2}$, which is released into Q-pool contained within lipid bilayer following protonation to QH$_2$. Two more photochemical turnovers provide the manganese cluster with four oxidizing equivalents necessary to split the two bound water molecules [21]. The overall reaction of water oxidation by PSII is given in Equation (1) [25], wherein H$^+_N$ represents protons on the negative side of the membrane, and H$^+_P$ represents protons on the positive side of the membrane.

$$2\ H_2O+2\ Q+4\ H^+_N \rightarrow O_2+2\ QH_2+4\ H^+_P \quad (1)$$

Both PSII and CMI use ubiquinone as an electron carrier. Ubiquinol is the fully reduced form of the molecule, which can be fully oxidized to ubiquinone or partially oxidized to semiquinone. There are many different analogues of ubiquinone, including for example decylubiquinone.

There is a need to provide biologically engineered organelle constructs comprising protein complexes from a variety of different organisms that can be used to convert light energy into reduced enzymatic cofactors.

SUMMARY

One embodiment described herein is an artificial cell free organelle system comprising: a membrane having two sides comprising an inner surface in contact with an inner aqueous medium and an outer surface in contact with an outer aqueous medium; one or more photosynthetic proteins and one or more oxidoreductase proteins are vectorially embedded within and traversing the membrane; one or more first redox active cofactors; one or more second redox active cofactors; water, and a photon energy source; wherein: when one or more photons are directed on the one or more photosynthetic proteins, the photosynthetic proteins harvest the photon energy and catalyze the oxidation of at least one water molecule in the inner aqueous medium, generating 0.5 equivalents of oxygen gas and yielding up to two protons and two electrons per two photons that are transferred to an oxidized form of the first redox active cofactor, generating a reduced form of the first redox active cofactor; the accumulation of protons in the inner aqueous medium generates a proton concentration gradient between the inner aqueous medium and the outer aqueous medium; and the one or more oxidoreductase proteins pumps protons from the inner aqueous medium through the membrane to the outer aqueous medium to reduce the proton concentration gradient and simultaneously catalyzes the transfer of electrons from the reduced first redox cofactor to an oxidized form of the second redox active cofactor, generating a reduced form of the second redox active cofactor and an oxidized form of the first redox active cofactor. In one aspect, the membrane comprises a biomimetic bilayer, a biomimetic three-dimensional bilayer, a unilamellar liposome, a planar membrane, or a membraneous polymer construct. In another aspect, the membraneous polymer construct comprises a triblock copolymer membrane comprising varying lengths of poly (dimethylsiloxane) (PDMS) as the hydrophobic membrane-forming block and poly(2-methyloxazoline) (PMOXA) as the hydrophilic membrane-forming block. In another aspect, the membrane comprises a closed unilamellar liposome comprising a phospholipid bilayer. In another aspect, the one or more photosynthetic proteins and one or more oxidoreductase proteins are vectorially embedded in the membrane using a detergent. In another aspect, the detergent comprises one or more of CHAPS (3-[(3-cholamidopropyl) dimethylammonio]-1-propanesulfonate), DDM (n-dodecyl-β-D-maltoside), OG (octyl-β-D-glucopyranoside), or Triton X-100. In another aspect, the one or more photosynthetic proteins comprises the photosystem II complex of proteins and/or bacteriorhodopsin. In another aspect, the photosystem II complex of proteins comprises the photosystem II complexes from *Cyanobacterium synechocystis, Synechocystis* sp., *Synechococcus elongates, Thermosynechococcus elongatus, Thermosynechococcus vulcans, Pisum sativum, Chlamydomonas reinhardtii, Spinacia oleracea*, or *Arabidopsis thaliana*; and the bacteriorhodopsin comprises the bacteriorhodopsin from *Halobacterium salinarum*. In another aspect, the photosystem II complex of proteins or bacteriorhodopsin are purified or recombinant. In another aspect, the one or more photosynthetic proteins comprise the photosystem II complex of proteins from *Synechocystis* sp. PCC6803. In another aspect, the one or more oxidoreductase enzymes comprises the Respiratory Complex I complex of proteins. In another aspect, the Respiratory Complex I complex of proteins comprises the Respiratory Complex I of *Eschericia coli, Thermus thermophilus, Vibrio cholerae, Yarrowia lipolytica, Ovis aries, Bos taurus, Mus musculus*, or *Homo sapiens*. In another aspect, the Respiratory Complex I complex of proteins are purified or recombinant. In another aspect, the one or more oxidoreductase enzymes comprises the Respiratory Complex I complex of proteins from *E. coli*. In another aspect, the one or more oxidoreductase enzymes comprises a Respiratory Complex I that has been engineered to preferentially reduce NADPH. In another aspect, the one or more oxidoreductase enzymes are vectorially incorporated into the membrane in an orientation opposite to the orientation of the oxidoreductase enzyme in vivo. In another aspect, the first redox active cofactor comprises ubiquinone or a ubiquinone analogue. In another aspect, the ubiquinone analogue has the structure:

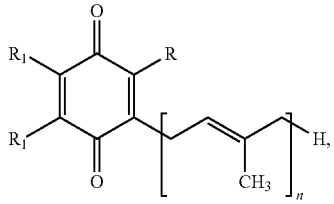

wherein R is methyl, hydroxyl, or hydrogen and $R_1$ is independently methoxy, methyl, hydroxyl or hydrogen, and n is an integer between 0 to 20, 6 to 12, or 7 to 10, including all integers within the specified ranges. In another aspect, the second redox active cofactor comprises $NAD^+$, $NADP^+$, an $NAD^+$ analogue, or an $NADP^+$ analogue. In another aspect, the $NAD^+$ or $NADP^+$ analogue has the structure:

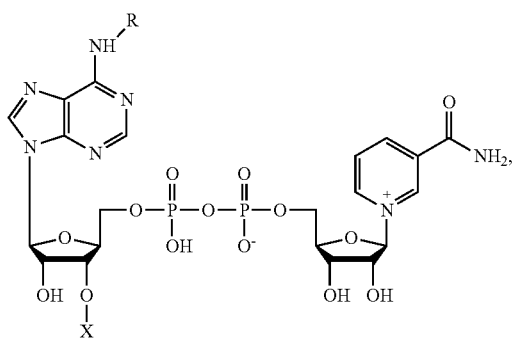

where R is a polyethylene glycol of 100 to 10,000 MW, a carbohydrate moiety or a polypeptide, and X is phosphate or hydrogen. In another aspect, the reduced form of the first redox active cofactor comprises ubiquinol, decylubiquinol, or a ubiquinol analogue. In another aspect, the ubiquinol analogue has the structure:

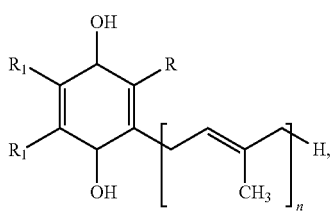

wherein R is methyl, hydroxyl, or hydrogen and $R_1$ is independently methoxy, methyl, hydroxyl or hydrogen, and n is an integer between 0 to 20, 6 to 12, or 7 to 10, including all integers within the specified ranges. In another aspect, the reduced form of the second redox active cofactor comprises NADH, NADPH, or an analogue thereof. In another aspect, the NADH or NADPH analogue has the structure:

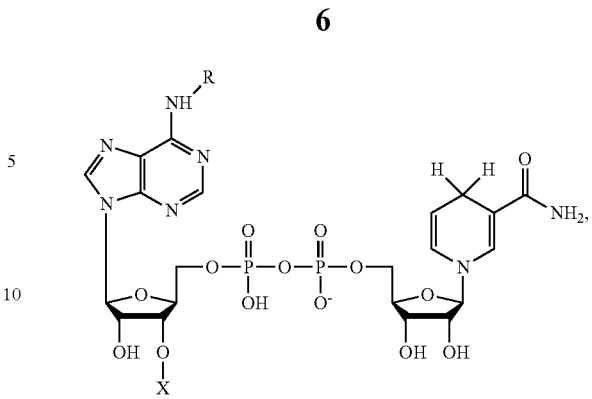

where R is a polyethylene glycol of 100 to 10,000 MW, a carbohydrate moiety, or a polypeptide, and X is phosphate or hydrogen. In another aspect, the system further comprises an ionophore comprising one or more of valinomycin, salinomycin, lasalocid, ionomycin, nonactin, beauvericin, or calcimycin. In another aspect, the system further comprises an ionophore comprising a potassium ionophore, and wherein the potassium ionophore comprises valinomycin or salinomycin.

Another embodiment described herein is a method or means for converting light energy and water into oxygen and reduced NADH, NADPH, or analogues thereof using artificial photosynthesis in an artificial cell free system, the method comprising: (a) providing an artificial cell free organelle system comprising: a membrane having two sides comprising an inner surface in contact with an inner aqueous medium and an outer surface in contact with an outer aqueous medium; one or more photosynthetic proteins comprising photosystem II or bacteriorhodopsin vectorially embedded within and traversing the membrane; one or more oxidoreductase proteins comprising Respiratory Complex I vectorially embedded within and traversing the membrane; ubiquinone or an analogue thereof; $NAD^+$, $NADP^+$ or an analogue thereof; water, and a photon energy source; (b) directing one or more photons to the one or more photosynthetic proteins; (c) the one or more photosynthetic proteins catalyzes the electron transfer from photon energy to ubiquinone or an analogue thereof, generating ubiquinol or an analogue thereof; and (d) the one or more oxidoreductase proteins catalyzes the electron transfer from ubiquinol or an analogue thereof to $NAD^+$, $NADP^+$, or analogues thereof, producing NADH, NADPH, or analogues thereof, and oxidizing ubiquinol or analogue thereof to ubiquinone or an analogue thereof. In one aspect, wherein: when one or more photons are directed on the one or more photosynthetic proteins, the photosynthetic proteins harvest the photon energy and catalyze the oxidation of at least one water molecule in the inner aqueous medium, generating 0.5 equivalents of oxygen gas and yielding up to two protons and two electrons per two photons that are transferred to ubiquinone or an analogue thereof, generating ubiquinol or an analogue thereof; the accumulation of protons in the inner aqueous medium generates a proton concentration gradient between the inner aqueous medium and the outer aqueous medium; and the oxidoreductase enzyme comprising Respiratory Complex I pumps protons from the inner aqueous medium through the membrane to the outer aqueous medium to reduce the proton concentration gradient and simultaneously catalyzes the transfer of electrons from ubiquinol or an analogue thereof to $NAD^+$, $NADP^+$, or analogues thereof, producing NADH, NADPH, or analogues thereof, and oxidizing ubiquinol or analogue thereof back to ubiquinone or a ubiquinone or an analogue thereof. In another aspect, the membrane comprises a biomimetic bilayer, a biomimetic three-dimensional bilayer, a unilamellar liposome, a planar membrane, or a membraneous polymer construct. In another aspect, the membraneous polymer construct comprises a triblock co-polymer membrane comprising varying lengths of poly(dimethylsiloxane) (PDMS) as the hydrophobic membrane-forming block and poly(2-methyloxazoline) (PMOXA) as the hydrophilic membrane-forming block. In another aspect, the membrane comprises a closed unilamellar liposome comprising a phospholipid bilayer. In another aspect, the one or more photosynthetic proteins and one or more oxidoreductase proteins are vectorially embedded in the membrane using a detergent. In another aspect, the detergent comprises one or more of CHAPS (3-[(3-cholamidopropyl)dimethylammonio]-1-propanesulfonate), DDM (n-dodecyl-β-D-maltoside), OG (octyl-β-D-glucopyranoside), or Triton X-100. In another aspect, the photosystem II complex of proteins comprises the photosystem II complexes from *Cyanobacterium synechocystis, Synechococcus elongates, Thermosynechococcus elongatus, Thermosynechococcus vulcans, Pisum sativum, Chlamydomonas reihhardtii, Spinacia oleracea,* or *Arabidopsis thaliana*; and the bacteriorhodopsin comprises the bacteriorhodopsin from *Halobacterium salinarum*. In another aspect, the photosystem II complex of proteins or bacteriorhodopsin are purified or recombinant. In another aspect, the one or more photosynthetic proteins comprise the photosystem II complex of proteins from *Cyanobacterium synechocystis*. In another aspect, the Respiratory Complex I complex of proteins comprises the Respiratory Complex I of *Eschericia coli, Thermus thermophilus, Vibrio cholerae, Yarrowia lipolytica, Ovis aries, Bos taurus, Mus musculus,* or *Homo sapiens*. In another aspect, the Respiratory Complex I complex of proteins are purified or recombinant. In another aspect, the one or more oxidoreductase enzymes comprises the Respiratory Complex I complex of proteins from *E. coli*. In another aspect, the one or more oxidoreductase enzymes comprises a Respiratory Complex I that has been engineered to preferentially reduce NADPH or an analogue thereof. In another aspect, the one or more oxidoreductase enzymes are vectorially incorporated into the membrane in an orientation opposite to the orientation of the oxidoreductase enzyme in vivo. In another aspect, the ubiquinone analogue has the structure:

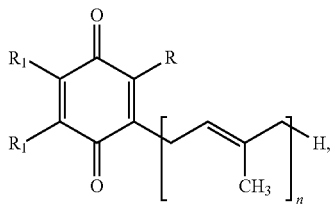

wherein R is methyl, hydroxyl, or hydrogen and R₁ is independently methoxy, methyl, hydroxyl or hydrogen, and n is an integer between 0 to 20, 6 to 12, or 7 to 10, including all integers within the specified ranges. In another aspect, the NAD⁺ or NADP⁺ analogue has the structure:

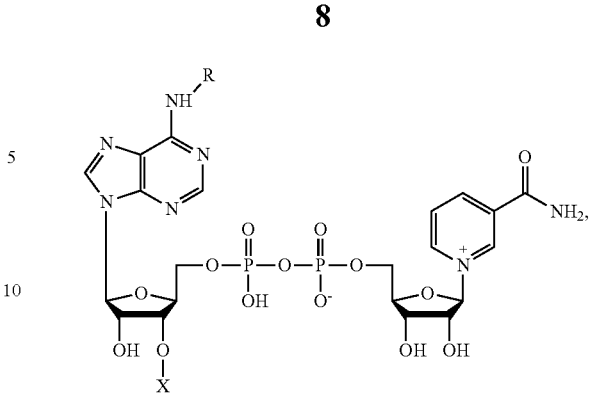

where R is a polyethylene glycol of 100 to 10,000 MW, a carbohydrate moiety or a polypeptide, and X is phosphate or hydrogen. In another aspect, the ubiquinol analogue has the structure:

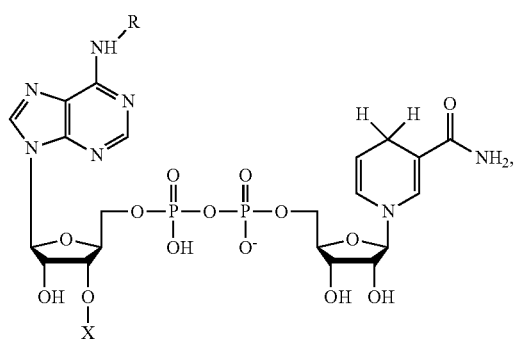

wherein R is methyl, hydroxyl, or hydrogen and R₁ is independently methoxy, methyl, hydroxyl or hydrogen, and n is an integer between 0 to 20, 6 to 12, or 7 to 10, including all integers within the specified ranges. In another aspect, the NADH or NADPH analogue has the structure:

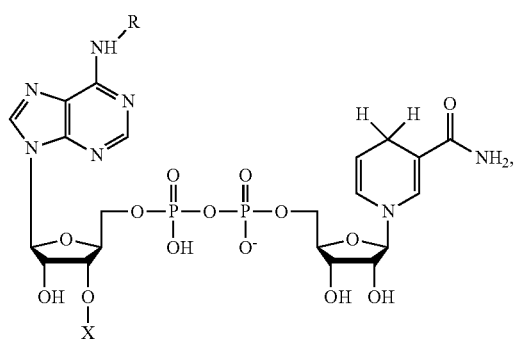

where R is a polyethylene glycol of 100 to 10,000 MW, a carbohydrate moiety, or a polypeptide, and X is phosphate or hydrogen. In another aspect, the method further comprises adding an ionophore comprising one or more of valinomycin, salinomycin, lasalocid, ionomycin, nonactin, beauvericin, or calcimycin. In another aspect, the method further comprises adding an ionophore comprising a potassium ionophore, and wherein the potassium ionophore comprises valinomycin or salinomycin.

Another embodiment described herein is NADH, NADPH, or analogues thereof produced by the methods described herein.

Another embodiment described herein is the use of an artificial cell free organelle system for converting light energy and water into oxygen and reduced NADH, NADPH, or analogues thereof using artificial photosynthesis in an artificial cell free system. In one aspect, the artificial cell free organelle system comprises: a membrane having two sides comprising an inner surface in contact with an inner aqueous medium and an outer surface in contact with an outer aqueous medium; one or more photosynthetic proteins comprising photosystem II or bacteriorhodopsin vectorially embedded within and traversing the membrane; one or more oxidoreductase proteins comprising Respiratory Complex I vectorially embedded within and traversing the membrane; ubiquinone or an analogue thereof; $NAD^+$, $NADP^+$ or an analogue thereof; water, and a photon energy source; wherein: the one or more photosynthetic proteins catalyzes the electron transfer from photon energy to ubiquinone or an analogue thereof, generating ubiquinol or an analogue thereof; and the one or more oxidoreductase proteins catalyzes the electron transfer from ubiquinol or an analogue thereof to $NAD^+$, $NADP^+$, or analogues thereof, producing NADH, NADPH, or analogues thereof, and oxidizing ubiquinol or analogue thereof to ubiquinone or an analogue thereof.

BRIEF DESCRIPTION OF THE DRAWINGS

Exemplary embodiments are illustrated in referenced figures of the drawings. It is intended that the embodiments and figures disclosed herein are to be considered illustrative rather than restrictive.

FIG. 2A shows a representative nickel affinity chromatogram. Solid dashed, and dotted lines represent absorbance at 280, 420, and 605 nm, respectively; the dashed-dotted line is the imidazole concentration. FIG. 2B shows a chromatogram on a HiLoad 16/600 Superdex 200 column. The black bars indicate fractions used in subsequent steps.

FIG. 4A shows the chromatogram from nickel affinity chromatography. The solid line, dashed line, and dotted line represent absorbance at 280, 480 and 673 nm, respectively. The dashed line overlaid with black dash-dot line is the imidazole concentration. FIG. 4B shows a chromatogram on a Superose 6 Increase 10/300 column to confirm purity. The black bar indicates fractions used in subsequent steps.

FIG. 5A shows the $NAD^+$ reduction rate vs. quantum flux of PCR-4 proteoliposomes with and without inhibition by DCMU. FIG. 5B shows the $NAD^+$ reduction rate of PCR-4 proteoliposomes with at 3000 µmol photons $s^{-1}$ $m^{-2}$ with linear equation fit for the first 3 minutes and exponential fit over 20 minutes of illumination. FIG. 5C shows the rates of $H^+$ consumption by CMI and production by PSII at 3,000 µmol photons $s^{-1}$ $m^{-2}$. FIG. 5D shows the coupling efficiency based on the stoichiometric H+ and consumption and production by CMI and PSII, respectively at 3,000 µmol photons $s^{-1}$ $m^{-2}$. The dotted lines in FIG. 5C and FIG. 5D are the 95% confidence bounds of the exponential best-fit equation. The error bars represent the SEM of N biological replicates with three technical replicates.

FIG. 8A shows NADH concentration and FIG. 8B shows ACMA signal for PCR-4 proteoliposomes (solid lines) and empty liposomes without protein (dashed lines). The results are the representation of three technical repeats of single biological replicate.

FIG. 9A shows NADH:DQ oxidoreductase (nmol NADH mg $CMI^{-1}$) activity of proteoliposomes with PCR-4 without DCMU and FIG. 9B shows results with DCMU. FIG. 9C shows the percent change in ACMA fluorescence of proteoliposomes without DCMU and FIG. 9D shows the results with DCMU. The light or dark condition is indicated along the top x-axis. The error bars represent the SEM of N biological replicates with three technical replicates for FIG. 9A-D and N biological replicates.

FIG. 11A shows NADH:DQ oxidoreductase activity of PCR-4 proteoliposomes (nmol NADH mg $CMI^{-1}$) versus time (min). The light or dark condition is indicated along the top x-axis. FIG. 11B shows NAD⁺ reduction rate (nmol NADH min$^{-1}$ mg CMI$^{-1}$) versus initial concentration of NADH (μmol) added. The error bars represent the SEM of N biological replicates each with three technical replicates for FIG. 11A and the standard deviation for N technical replicate for a single biological replicate for FIG. 11B.

FIG. 13A shows the NADH:DQ oxidoreductase activity versus time; after 5 minutes of incubation at 28° C., 200 μM NADH was added (indicated by the arrow) to samples that included Piericidin A, and CCCP. FIG. 13B shows 4ΔACMA vs. time. FIG. 13C shows the same as FIG. 13B but at 8 minutes 5 μM CCCP was added to all samples to confirm the change in ΔACMA was caused by abolishing a proton gradient. Each trace is the mean of three technical repeats of a single biological replicate.

DETAILED DESCRIPTION

Figure 1A:
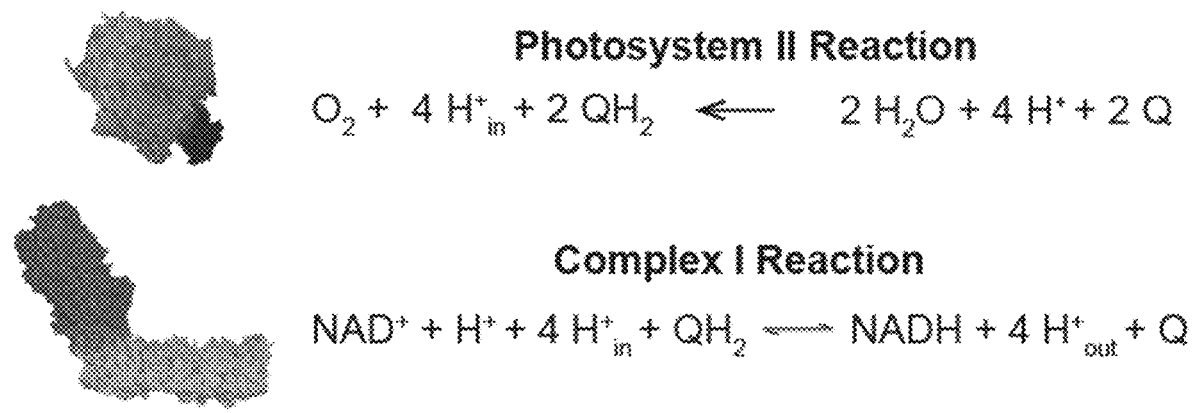
FIG. 1A is a schematic diagram showing the reactions catalyzed by Photosystem II (PSII) and Respiratory Complex I (CMI).

Unless otherwise defined, all technical and scientific terms used herein have the same meaning as commonly understood by one of ordinary skill in the art. For example, any nomenclatures used in connection with, and techniques of, cell and tissue culture, molecular biology, immunology, microbiology, genetics, and protein and nucleic acid chemistry and hybridization described herein are well known and commonly used in the art. In case of conflict, the present document, including definitions, will control. Preferred methods and materials are described below, although methods and materials similar or equivalent to those described herein can be used in practice or testing of the present invention.

As used herein, the terms "amino acid," "nucleotide," "polynucleotide," "vector," "polypeptide," and "protein" have their common meanings as would be understood by a biochemist of ordinary skill in the art. Standard single letter nucleotides (A, C, G, T, U) and standard single letter amino acids (A, C, D, E, F, G, H, I, K, L, M, N, P, Q, R, S, T, V, W, or Y) are used herein.

As used herein, the terms such as "include," "including," "contain," "containing," "having," and the like mean "comprising." The present disclosure also contemplates other embodiments "comprising," "consisting of," and "consisting essentially of," the embodiments or elements presented herein, whether explicitly set forth or not.

As used herein, the term "a," "an," "the" and similar terms used in the context of the disclosure (especially in the context of the claims) are to be construed to cover both the singular and plural unless otherwise indicated herein or clearly contradicted by the context. In addition, "a," "an," or "the" means "one or more" unless otherwise specified.

As used herein, the term "or" can be conjunctive or disjunctive.

As used herein, the term "substantially" means to a great or significant extent, but not completely.

As used herein, the term "about" or "approximately" as applied to one or more values of interest, refers to a value that is similar to a stated reference value, or within an acceptable error range for the particular value as determined by one of ordinary skill in the art, which will depend in part on how the value is measured or determined, such as the limitations of the measurement system. In one aspect, the term "about" refers to any values, including both integers and fractional components that are within a variation of up to ±10% of the value modified by the term "about." Alternatively, "about" can mean within 3 or more standard deviations, per the practice in the art. Alternatively, such as with respect to biological systems or processes, the term "about" can mean within an order of magnitude, in some embodiments within 5-fold, and in some embodiments within 2-fold, of a value. As used herein, the symbol "~" means "about" or "approximately."

All ranges disclosed herein include both end points as discrete values as well as all integers and fractions specified within the range. For example, a range of 0.1-2.0 includes 0.1, 0.2, 0.3, 0.4 . . . 2.0. If the end points are modified by the term "about," the range specified is expanded by a variation of up to ±10% of any value within the range or within 3 or more standard deviations, including the end points.

As used herein, the terms "control," or "reference" are used herein interchangeably. A "reference" or "control" level may be a predetermined value or range, which is employed as a baseline or benchmark against which to assess a measured result. "Control" also refers to control experiments or control cells.

Throughout the following description specific details are set forth in order to provide a more thorough understanding to persons skilled in the art. However, well known elements may not have been shown or described in detail to avoid unnecessarily obscuring the disclosure. Accordingly, the description and drawings are to be regarded in an illustrative, rather than a restrictive, sense.

Described herein is an artificial engineered biotic/abiotic organelle system that can be used to regenerate enzymatic cofactors. As an example, an artificial organelle was engineered to reduce NAD⁺ using light and water, producing oxygen as a by-product, to fuel metabolic chemical synthesis. This system reduces nicotinamide coenzymes using light for energy. It sources the required electrons from water and generates oxygen as the sole by-product. This is accomplished by coupling two complex membrane proteins that do not directly interact in nature: Photosystem II and Respiratory Complex I. Through controlled vectoral assembly into an example embodiment using 180 nm lipid vesicles, these two proteins have been demonstrated to function cooperatively to yield NADH. An example embodiment of this system demonstrated reduction rates of 343.55±18.55 nmol min$^{-1}$ mg Complex I$^{-1}$ (n=7) over multiple oxidation/reduction cycles. By providing a critical enzymatic energy source that is regenerated from captured light, this technology could be applied to any isolated enzyme process that requires NADH or NADPH to produce chemicals.

As used herein, the term "vectoral" as used with reference to a membrane protein refers to a membrane protein having a specific orientation within a membrane, for example having the N-terminus of the protein always (or preferentially) on only one of the interior or the exterior of a vesicle or artificial organelle. As used with reference to a direction of transport, "vectoral" or "vectorial" means unidirectional transport from a first side of a membrane to a second side of the membrane. The term "vectoral" or "vectorially" as used with reference to the incorporation or reconstitution of a membrane protein into a membrane likewise refers to incorporating the membrane protein preferentially in a specific orientation with respect to a membrane, for example reconstituting the protein so that the N-terminus of most molecules of the protein is on only one of either the interior or the exterior of a vesicle or artificial organelle.

As used herein, "vesicle" refers to a membrane-bound fluid filled sac.

As used herein, "artificial organelle" refers to a vesicle with transmembrane proteins incorporated into the membrane of the vesicle. In one embodiment, the vesicle is a liposome.

As used herein "thermostable" means a first protein that is stable to a relatively higher temperature than a second protein. A thermostable protein may be obtained, for example, by obtaining that protein from an organism that is a thermophile or extremophile.

As used herein, the term "$NAD^+$" refers to the oxidized form of nicotinamide adenine dinucleotide and "NADH" refers to the reduced form. NAD+ can be converted to NADH by the addition of two electrons and two protons as shown:

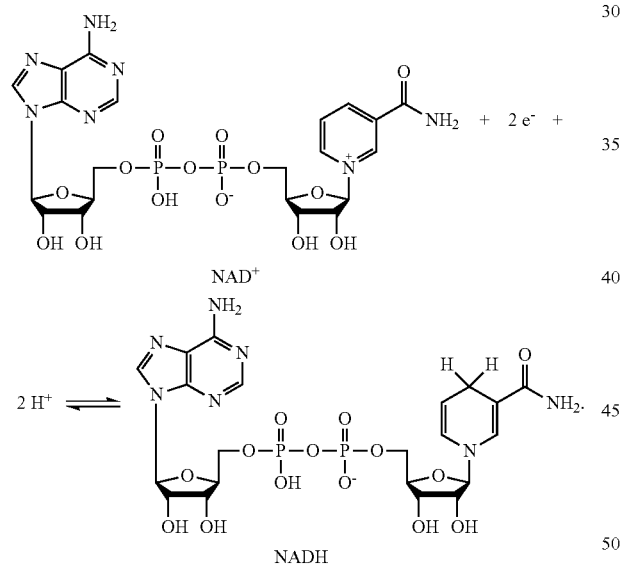

NADP+ and NADPH are analagous to $NAD^+$ and NADH and have a phosphate $(PO_4)^{2-}$ moiety attached to the adenosine ribose 2'-hydroxyl (bolded above) forming a phosphoester linkage.

As used herein, the terms "$NAD^+$ analogue," "$NADP^+$ analogue," "NADH analogue" or "NADPH analogue" refer to a modified form of $NAD^+$, $NADP^+$, NADH, or NADPH (i.e., $NADX^+$ or NADXH, for simplicity). In one embodiment the NADX/H analogue comprises a PEGylated form of NAD(P)(H) or a conjugate of NAD(P)(H) with one or more moieties including carbohydrates or proteins. [26-27]. The modification, such as pegylation can be on the 6-amino group of adenine, as shown below in structures (1) or (2):

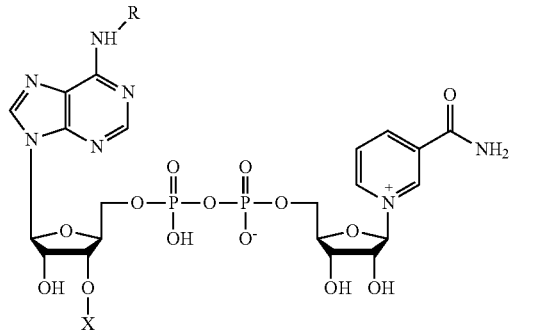

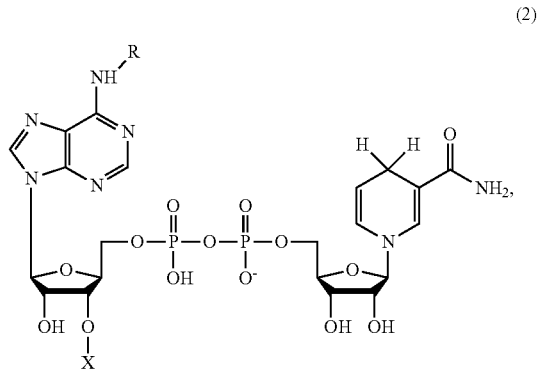

where R is a polyethylene glycol of 100 to 10,000 MW, a carbohydrate (e.g., sugar), or a polypeptide and X is a phosphate moiety or hydrogen. Other modifications include conjugates to the 2'- or 3'-hydroxyl moieties of the ribose sugars of adenosine or the nicotinamide riboside.

As used herein, the term "ubiquinone analogue" or "ubiquinol analogue" comprises compounds having the following structures (3) or (4):

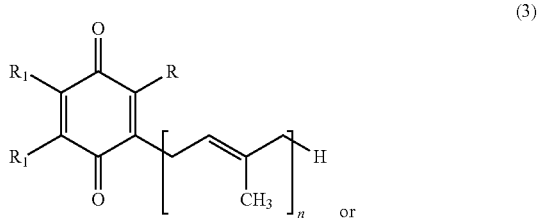

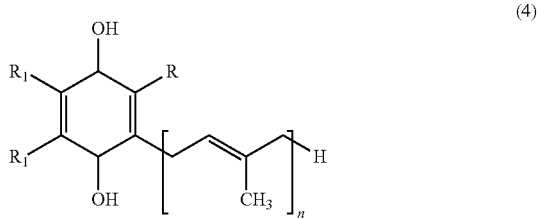

wherein R is methyl, hydroxyl, or hydrogen and $R_1$ is independently methoxy, methyl, hydroxyl or hydrogen, and n is an integer between 0 to 20, 6 to 12, or 7 to 10, including all integers within the specified ranges. Structures (3) and (4) shows a ubiquinone analogue and a ubiquinol analogue respectively but are representative of the hemi-reduced forms of ubiquinone, i.e., a "semiquinone analogue."

In one embodiment, a "ubiquinone analogue" or "ubiquinol analogue" comprises compounds having the following structures (5) or (6):

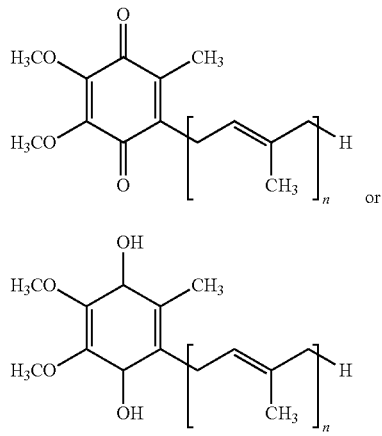

(5)

(6)

wherein n is any integer. In another embodiment, n is an integer between 6 and 12, including any value there between, e.g., 7, 8, 9, or 10. In another embodiment, n is an integer between 0 and 20, including any value there between. In another embodiment, one or more of the methyl or methoxy substituents on the benzoquinone ring is absent or comprises a different substituent group. For example, in some embodiments one or both of the methoxy groups may be absent from the benzoquinone ring or may independently be a different substituent such as a hydroxyl group. In another embodiment, the methyl group may be absent from the benzoquinone ring or may be a different substituent. Structures (5) and (6) shows ubiquinone and ubiquinol analogues but are representative of the hemi-reduced forms of ubiquinone, i.e., a "semiquinone analogue."

In one embodiment, "ubiquinone" or "Coenzyme Q" and "ubiquinol" have the following structures (7) or (8), respectively:

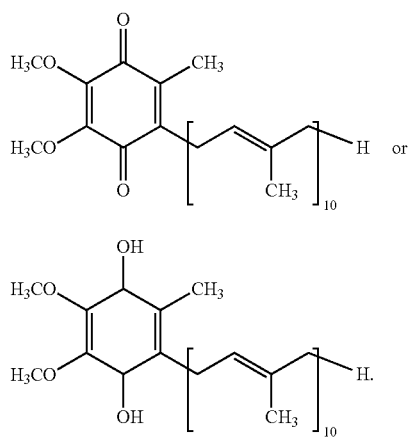

(7)

(8)

Ubiquinone has three redox states: fully oxidized (ubiquinone); partially reduced (semiquinone), and fully reduced (ubiquinol). Two electrons and two protons are required to fully reduce ubiquinone to ubiquinol as shown:

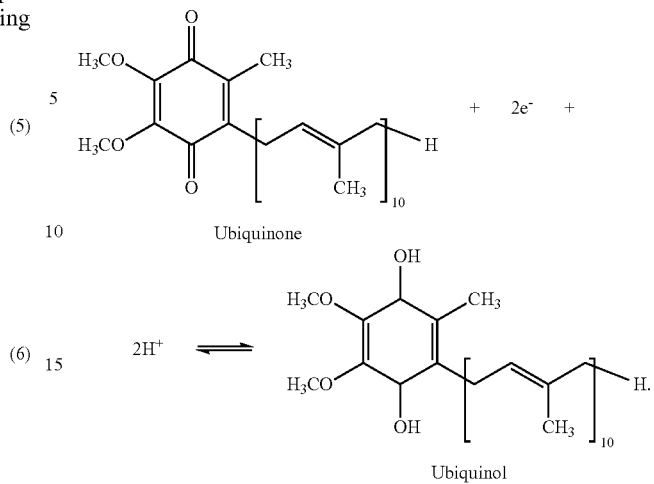

Ubiquinone

Ubiquinol

Semiquinone, not shown, is the intermediate form between a fully oxidized (ubiquinone) and fully reduced (ubiquinol) and has one hydroxyl moiety and one carbonyl moiety on the benzyl ring. As mentioned above, the analogues of ubiquinone and ubiquinol shown in structures (3)-(6) are representative of analogues of semiquinone depending on the redox state of the molecule.

Membranes suitable for use in accordance with various embodiments described herein can be any suitable material having a hydrophobic interior region surrounded by two hydrophilic regions, wherein the two hydrophilic regions are respectively in contact with aqueous solution on opposite first (e.g., inner) and second (e.g., outer) sides of the membrane. The membrane can be any suitable biomimetic membrane. The membrane can be a planar membrane or a polymer construct. For example, the membrane can be a solid substrate supported lipid or polymers with functionalized end groups which can be an azide, an alkyne, an alkene, a vinyl, an azidophenyl, or a thiol. The functionalized lipid or polymer can be coupled to a solid support surface by reaction of at least one functional group of at least one of the plurality of functionalized lipids or polymers. For example, in some embodiments the membrane comprises triblock co-polymers, which in some embodiments are in the form of a vesicle. Examples of biomimetic membranes are described by Shen et al., *J. Mem. Sci.* 454: 359-381 [28], which is incorporated by reference herein in its entirety for such teachings. In another embodiment, the triblock co-polymer comprises varying lengths of poly(dimethylsiloxane) (PDMS) as the hydrophobic membrane-forming block and poly(2-methyloxazoline) (PMOXA) as the hydrophilic membrane-forming block. In another embodiment, the membrane can be a lipid layer or a lipid bilayer. In some embodiments the membrane is in the form of a liposome. In another embodiment, the membrane comprises a unilamellar liposome. In another embodiment, the membrane comprises a closed unilamellar liposome.

In another embodiment, an engineered enzymatic cofactor regeneration system is constructed by incorporating a photosynthetic reaction center and an oxidoreductase enzyme into a membrane to use light energy to regenerate an enzymatic cofactor. In another embodiment, the photosynthetic reaction center uses energy from photons (i.e., hv or light), to: (1) split water to produce protons on a first side of the membrane to form a proton gradient from the first side of the membrane to a second side of the membrane; and (2)

reduce ubiquinone (or an analogue thereof) to ubiquinol (or analogue thereof) within the hydrophobic portion of the membrane. In another embodiment, the oxidoreductase enzyme uses energy provided by the proton gradient and the ubiquinol (or analogue thereof) produced by the photosynthetic reaction center to carry out reverse electron transfer to reduce the enzymatic cofactor, thereby regenerating the enzymatic cofactor. In the process, water is used as the source of electrons to reduce the enzymatic cofactor, and oxygen is produced as a byproduct.

Any suitable method of achieving vectoral orientation of a membrane protein in a membrane can be used. Conventional approaches include mechanical means or detergent assisted reconstitution and rely on van der Waals and hydrophobic interactions to encourage the removal of detergent and embedding into the membrane material. This may be a slow process (days to weeks) and requires an external mechanical or thermodynamic force to drive detergent removal and offers limited control of transmembrane protein orientation [29]. Other methods for vectoral incorporation of membrane proteins into membranes are known. Liang et al. were the first to examine the impact of tuning electrostatic interactions between transmembrane proteins and the membrane material [30]. Transmembrane proteins are heterogeneously charged; the hydrophobic membrane spanning domains are largely anionic and the extramembrane domains comprise various charged amino acids. Using cationic lipids, transmembrane proteins can be rapidly assembled into the lipid bilayer and directed through electrostatic interactions [31]. This paradigm of charge-interaction-directed reconstitution (CIDR) translated to "rationally" designed amphiphilic block copolymers [32].

In another embodiment, the engineered enzymatic cofactor regeneration system comprises an artificial organelle, i.e., a vesicle formed from a membrane with the incorporated photosynthetic reaction center and oxidoreductase enzyme. In another embodiment, the artificial organelle comprises a proteoliposome, in which the membrane comprises a lipid bilayer membrane. In another embodiment, the artificial organelle contains a vectorially incorporated photosynthetic reaction center and a vectorially incorporated oxidoreductase enzyme. In another embodiment, the photosynthetic reaction center is oriented to produce a proton gradient from the inside to the outside of the vesicle, and the oxidoreductase enzyme is oriented to pump protons from the inside to the outside of the vesicle to carry out reverse electron transfer to reduce the enzymatic cofactor to be regenerated.

In one embodiment, the light harvesting protein is photosystem II (PSII) from any species of photosynthetic organism including plants, archaea, blue green algae, or the like. In another embodiment, the light harvesting protein is a thermostable photosystem II (PSII) from an extremophilic or thermophilic organism. In one embodiment, the light harvesting protein is photosystem II (PSII) is from *Cyanobacterium synechocystis, Synechocystis* sp., *Synechococcus elongates, Thermosynechococcus elongatus, Thermosynechococcus vulcans, Pisum sativum, Chlamydomonas reinhardtii, Spinacia oleracea*, or *Arabidopsis thaliana*.

In one embodiment, the photosynthetic reaction center is photosystem II (PSII) from *Synechocystis* sp. (strain PCC 6803).

In one embodiment, the photosynthetic reaction center is photosystem II (PSII) from *Synechocystis* sp. (strain PCC 6803) which comprises polypeptides having 90% to 100% identity to the polypeptides listed in Table 1 and SEQ ID NO: 1-20.

TABLE 1

Photosystem II Proteins *Synechocystis* sp. (strain PCC 6803)

| UNIPROT ID | Name | SEQ ID NO |
|---|---|---|
| P05429 | Photosystem II CP47 reaction center protein; 507 residues | SEQ ID NO: 1 |

MGLPWYRVHTVVLNDPGRLISVHLMHTALVAGWAGSMALYELAIFDSSDAVLNPMWRQGMFVLPFMARLGVTSSWN
GWSVTGETGLDPGFWSFEGVAAAHIVLSGLLFLAAVWHWVFWDLELFVDPRTGESALDLPKMFGIHLFLSGLLCFG
FGAFHLTGVWGPGMWVSDPYGLTGHVQPVAPEWGPAGFNPFNPGGVVAHHIAAGIVGIIAGLFHLTVRPPERLYKA
LRMGNIETVLSSSIAAVFFAAFVVAGTMWYGNATTPIELFGPTRYQWDKGYFQEEIQRRVDSQLAEGASLSEAWST
IPEKLAFYDYVGNSPAKGGLFRTGAMNSGDGIAQEWIGHPIFKDKEGRELEVRRMPNFFETFPVIMTDADGVVRAD
IPFRRSESKFSVEQTGVTVSFYGGALDGQTFSNPSDVKKFARKAQLGEGFDFDTETFNSDGVFRTSPRGWFTFGHA
VFALLFFFGHIWHGSRTLFRDVFAGVDPGLEEQVEFGVFAKVGDLSTRKEA

| P09193 | Photosystem II CP43 reaction center protein; 460 residues | SEQ ID NO: 2 |

MVTLSNTSMVGGRDLPSTGFAWWSGNARLINLSGKLLGAHVAHAGLIVFWAGAMTLFEVAHFIPEKPMYEQGLILL
PHIATLGWGVGPAGEVTDIFPPFVVGVLHLISSAVLGLGGIYHALRGPEVLEEYSSFFGYDWKDKNQMTNIIGYHL
ILLGCGALLLVFKAMFFGGVYDTWAPGGGDVRVITNPTLNPAIIFGYLLKAPFGGEGWIISVNNMEDIIGGHIWIG
LICISGGIWHILTKPFGWARRALIWSGEAYLSYSLGALSLMGFIASVFVWFNNTAYPSEFYGPTGMEASQSQAFTF
LVRDQRLGANIASAQGPTGLGKYLMRSPSGEIIFGGETMRFWDFRGPWLEPLRGPNGLDLDKLRNDIQPWQVRRAA
EYMTHAPLGSLNSVGGVITDVNSFNYVSPRAWLATSHFVLGFFFLVGHLWHAGRARAAAAGFEKGIDRETEPTLFM
PDLD

| P14835 | Photosystem II reaction center protein H; 64 residues | SEQ ID NO: 3 |

MAQRTRLGDILRPLNSEYGKVVPGWGTTPVMGVFMALFLVFLLIILQIYNSSLILEGFSVDWAG

| Q54697 | Photosystem II reaction center protein I; 38 residues | SEQ ID NO: 4 |

MLTLKIAVYIVVGLFISLFIFGFLSSDPTRNPGRKDFE

| P73070 | Photosystem II reaction center protein J; 39 residues | SEQ ID NO: 5 |

MFAEGRIPLWVVGVVAGIGAIGVLGLFFYGAYAGLGSSM

TABLE 1-continued

Photosystem II Proteins *Synechocystis* sp. (strain PCC 6803)

| UNIPROT ID | Name | SEQ ID NO |
|---|---|---|
| P15819 | Photosystem II reaction center protein K; 45 residues | SEQ ID NO: 6 |

METIYLLAKLPEAYQIFDPLVDVLPVIPLFFLALAFVWQAAVGFK

| Q55354 | Photosystem II reaction center protein L; 39 residues | SEQ ID NO: 7 |

MDRNSNPNRQPVELNRTSLYLGLLLVAVLGILFSSYFFN

| P72701 | Photosystem II reaction center protein M; 35 residues | SEQ ID NO: 8 |

MQVNNLGFIASILFVLVPTVFLLILFIQTGKQSES

| P74787 | Photosystem II reaction center protein T; 31 residues | SEQ ID NO: 9 |

MESVAYILVLTMALAVLFFAIAFREPPRIEK

| P72575 | Photosystem II reaction center X protein; 39 residues | SEQ ID NO: 10 |

MTPSLANFLWSLVLGAAIVLIPATVGLIFISQKDKITRS

| P73676 | Photosystem II protein Y; 39 residues | SEQ ID NO: 11 |

MDWRVIVVVSPLLIAATWAAINIGAAAIRQLQDVLGREA

| Q55438 | Photosystem II reaction center protein Ycf12; 39 residues | SEQ ID NO: 12 |

MELLAALNLEPIFQLTFLGLIVLAGPAVVFVLAFRGGDL

| P73528 | Photosystem II reaction center protein Z; 62 residues | SEQ ID NO: 13 |

MSIVFQIALAALVLFSFVMVVGVPVAYASPQNWDRSKPLLYLGSGIWAILVIVVALLNFLVV

| Q55356 | Photosystem II reaction center Psb28 protein; 112 residues | SEQ ID NO: 14 |

MAEIQFSKGVAETVVPEVRLSKSKNGQSGMAKFYFLEPTILAKESTDDITGMYLIDDEGEIITREVKGKFINGRPT
AIEATVILNSQPEWDRFMRFMERYGAENGLGFSKSE

| P07826 | Photosystem II protein D11; 360 residues | SEQ ID NO: 15 |

MTTTQLGLQEQSLWSRFCCWITSTSNRLYIGWFGVLMIPTLLTATTCFIIAFIAAPPVDIDGIREPIAGSLLYGNN
IITAAVVPSSNAIGLHFYPIWEAHSLDEWLYNGGPYQLIVFHFLIGIFCYLGRQWELSYRLGMRPWICVAYSAPVA
AATATLLIYSIGQGSFSDGLPLGISGTFNFMLVLQAEHNVLMHPFHMLGVAGVFGGALFAAMHGSLVTSSLIRETT
EVESQNQGYKFGQEEETYNIVAAHGYFGRLIFQYASFNNSRALHFFLGAWPVVGIWFAALAVCCFAFNLNGFNFNQ
SILDAQGRPVSTWADVINRANIGFEVMHERNVHNFPLDLASGDAQMVALNAPAIEG

| P16033 | Photosystem II protein D12; 360 residues | SEQ ID NO: 16 |

MTTTLQQRESASLWEQFCQWVTSTNNRIYVGWFGTLMIPTLLTATTCFIIAFIAAPPVDIDGIREPVAGSLLYGNN
IISGAVVPSSNAIGLHFYPIWEAASLDEWLYNGGPYQLVVFHFLIGIFCYMGRQWELSYRLGMRPWICVAYSAPVS
AATAVFLIYPIGQGSFSDGMPLGISGTFNFMIVFQAEHNILMHPFHMLGVAGVFGGSLFSAMHGSLVTSSLVRETT
EVESQNYGYKFGQEEETYNIVAAHGYFGRLIFQYASFNNSRLHFFLGAWPVIGIWFTAMGVSTMAFNLNGFNFNQ
SILDSQGRVIGTWADVLNRANIGFEVMHERNAHNFPLDLASGEQAPVALTAPAVNG

| P09192 | Photosystem II D2 protein; 352 residues | SEQ ID NO: 17 |

MTIAVGRAPVERGWFDVLDDWLKRDRFVFIGWSGLLLFPCAFMALGGWLIGTTFVTSWYTHGLASSYLEGANFLTV
AVSSPADAFGHSLLFLWGPEAQGNLTRWFQIGGLWPFVALHGAFGLIGFMLRQFEISRLVGIRPYNAIAFSGPIAV
FVSVFLHMYPLGQSSWFFAPSFGVAGIFRFILFLQGFHNWTLNPFHMMGVAGILGGALLCAIHGATVENTLFEDGED
SNTFRAFEPTQAEETYSMVTANRFWSQIFGIAFSNKRWLHFFMLFVPVTGLWMSSVGIVGLALNLRAYDFVSQELR
AAEDPEFETFYTKNILLNEGMRAWMAPQDQPHENFIFPEEVLPRGNAL

| P10549 | Photosystem II manganese-stabilizing polypeptide; 274 residues | SEQ ID NO: 18 |

MRFRPSIVALLSVCFGLLTFLYSGSAFAVDKSQLTYDDIVNTGLANVCPEISSFTRGTIEVEPNTKYFVSDFCMEP
QEYFVKEEPVNKRQKAEYVKGKVLTRQTTSLEQIRGSIAVGADGTLTFKEKDGIDFQPITVLLPGGEEVPFFFTVK
NFTGTTEPGFTSINSSTDFVGDFNVPSYRGAGFLDPKARGLYTGYDNAVALPSAADKFRINKKETPLGKGILSLQV
TQVDGSTGEIAGIFESEQPSDTDLGAKEPLDVKVRGIFYGRVDTDV

| P74367 | Photosystem II lipoprotein Psb27; 134 residues | SEQ ID NO: 19 |

MSFLKNQLSRLLALILVVAIGLTACDSGTGLTGNYSQDTLTVIATLREAIDLPQDAPNRQEVQDTARGQINDYISR
YRRKGDAGGLKSFTTMQTALNSLAGYYTSYGARPIPEKLKKRLQLEFTQAERSIERGV

| Q55332 | Photosystem II 12 kDa extrinsic protein; 131 residues | SEQ ID NO: 20 |

MKFISRLLVACSLLIGLMGFLGADLAQALTPNPILAELNAVDAKLTTDFGQKIDLNNSDIRDFRGLRGFYPNLASE
IIKNAPYDTVEEVLDIPGLSETQKSRLEANLGSFTVTEPSIELTSGDDRINPGVY

In another embodiment, the light harvesting protein is a bacteriorhodopsin (BR), proteorhodopsin (PR), archaerhodopsin (AR), xanthorhodopsin (xR) or Gloeobacter rhodopsin (GR). In one embodiment, the bacteriorhodopsin comprises thermostable or extremophilic 5 bacteriorhodopsin from a thermophilic or extremophilic organism. In one embodiment, the bacteriorhodopsin comprises the bacteriorhodopsin from *Halobacterium salinarum*.

In one embodiment, bacteriorhodopsin from *Halobacterium salinarum* which comprises polypeptides having 90% to 100% identity to the polypeptide listed in Table 2 and SEQ ID NO: 21.

TABLE 2

| Bacteriorhodopsin Halobacterium salinarum (strain ATCC 29341) | | |
|---|---|---|
| UNIPROT ID | Name | SEQ ID NO |
| B0R5N9 | Bacteriorhodopsin; 262 residues | SEQ ID NO: 21 |

```
MLELLPTAVEGVSQAQITGRPEWIWLALGTALMGLGTLYFLVKGMGVSDPDAKKFYAITTLVPAIAFTMYLSMLLG
YGLTMVPFGGEQNPIYWARYADWLFTTPLLLLDLALLVDADQGTILALVGADGIMIGTGLVGALTKVYSYRFVWWA
ISTAAMLYILYVLFFGFTSKAESMRPEVASTFKVLRNVTVVLWSAYPVVWLIGSEGAGIVPLNIETLLFMVLDVSA
KVGFGLILLRSRAIFGEAEAPEPSAGDGAAATSD
```

In another embodiment, the oxidoreductase enzyme is respiratory complex (I) (CMI, NADH:Ubiquinone oxidoreductase), which is used to carry out reverse electron transfer to reduce the enzymatic cofactor, for example by reducing NAD$^+$ to NADH. In another embodiment, the CMI is from any organism or species. In another embodiment, the CMI is thermostable CMI from an extremophilic or thermophilic organism. In another embodiment, the CMI is from *Eschericia coli, Thermus thermophilus, Vibrio cholerae, Yarrowia lipolytica, Ovis aries, Bos taurus, Mus musculus,* or *Homo sapiens*. In one embodiment, the oxidoreductase enzyme is respiratory complex (I) (CMI, NADH:Ubiquinone oxidoreductase), from *E. coli*.

In one embodiment, oxidoreductase enzyme is respiratory complex (I) (CMI, NADH:Ubiquinone oxidoreductase), from *E. coli* which comprises polypeptides having 90% to 100% identity to the polypeptides listed in Table 3 and SEQ ID NO: 22-34.

TABLE 3

| Respiratory Complex I proteins Escherichia coli (strain K12) | | |
|---|---|---|
| UNIPROT ID | Name | SEQ ID NO |
| P0AFC3 | NADH-quinone oxidoreductase subunit A; 147 residues | SEQ ID NO: 22 |

```
MSMSTSTEVIAHHWAFAIFLIVAIGLCCLMLVGGWFLGGRARARSKNVPFESGIDSVGSARLRLSAKFYLVAMFFV
IFDVEALYLFAWSTSIRESGWVGFVEAAIFIPVLLAGLVYLVRIGALDWTPARSRRERMNPETNSIANRQR
```

| P0AFC7 | NADH-quinone oxidoreductase subunit B; 220 residues | SEQ ID NO: 23 |
|---|---|---|

```
MDYTLTRIDPNGENDRYPLQKQEIVTDPLEQEVNKNVFMGKLNDMVNWGRKNSIWPYNFGLSCCYVEMVTSFTAVH
DVARFGAEVLRASPRQADLMVVAGTCFTKMAPVIQRLYDQMLEPKWVISMGACANSGGMYDIYSVVQGVDKFIPVD
VIIPGCPPRPEAYMQALMLLQESIGKERRPLSWVVGDQGVYRANMQSERERKRGERIAVTNLRTPDEI
```

| P33599 | NADH-quinone oxidoreductase subunit C/D; 596 residues | SEQ ID NO: 24 |
|---|---|---|

```
MTDLTAQEPAWQTRDHLDDPVIGELRNREGPDAFTVQATRTGVPVVWIKREQLLEVGDFLKKLPKPYVMLFDLHGM
DERLRTHREGLPAADFSVFYHLISIDRNRDIMLKVALAENDLHVPTFTKLFPNANWYERETWDLFGITFDGHPNLR
RIMMPQTWKGHPLRKDYPARATEFSPFELTKAKQDLEMEALTFKPEEWGMKRGTENEDFMELNLGPNHPSAHGAFR
IVLQLDGEEIVDCVPDIGYHHRGAEKMGERQSWHSYIPYTDRIEYLGGCVNEMPYVLAVEKLAGITVPDRVNVIRV
MLSELFRINSHLLYISTFIQDVGAMTPVFFAFTDRQKIYDLVEAITGERMHPAWFRIGGVAHDLPRGWDRLLREFL
DWMPKRLASYEKAALQNTILKGRSQGVAAYGAKEALEWGTTGAGLRATGIDFDVRKARPYSGYENFDFEIPVGGGV
SDCYTRVMLKVEELRQSLRILEQCLNNMPEGPFKADHPLTTPPPKERTLQHIETLITHFLQVSWGPVMPANESFQM
IEATKGINSYYLTSDGSTMSYRTRVRTPSFAHLQQIPAAIRGSLVSDLIVYLGSIDFVMSDVDR
```

| P0AFD1 | NADH-quinone oxidoreductase subunit E; 166 residues | SEQ ID NO: 25 |
|---|---|---|

```
MHENQQPQTEAFELSAAEREAIEHEMHHYEDPRAASIEALKIVQKQRGWVPDGAIHAIADVLGIPASDVEGVATFY
SQIFRQPVGRHVIRYCDSVVCHINGYQGIQAALEKKLNIKPGQTTFDGRFTLLPTCCLGNCDKGPNMMIDEDTHAH
LTPEAIPELLERYK
```

| P31979 | NADH-quinone oxidoreductase subunit F; 445 residues | SEQ ID NO: 26 |
|---|---|---|

```
MKNIIRTPETHPLTWRLRDDKQPVWLDEYRSKNGYEGARKALTGLSPDEIVNQVKDAGLKGRGGAGFSTGLKWSLM
PKDESMNIRYLLCNADEMEPGTYKDRLLMEQLPHLLVEGMLISAFALKAYRGYIFLRGEYIEAAVNLRRAIAEATE
AGLLGKNIMGTGFDFELFVHTGAGRYICGEETALINSLEGRRANPRSKPPFPATSGAWGKPTCVNNVETLCNVPAI
LANGVEWYQNISKSKDAGTKLMGFSGRVKNPGLWELPFGTTAREILEDYAGGMRDGLKFKAWQPGGAGTDFLTEAH
LDLPMEFESIGKAGSRLGTALAMAVDHEINMVSLVRNLEEFFARESCGWCTPCRDGLPWSVKILRALERGEGQPGD
IETLEQLCRFLGPGKTFCAHAPGAVEPLQSAIKYFREEFEAGIKQPFSNTHLINGIQPNLLKERW
```

| P33602 | NADH-quinone oxidoreductase subunit G; 908 residues | SEQ ID NO: 27 |
|---|---|---|

```
MATIHVDGKEYEVNGADNLLEACLSLGLDIPYFCWHPALGSVGACRQCAVKQYQNAEDTRGRLVMSCMTPASDGTF
ISIDDEEAKQFRESVVEWLMTNHPHDCPVCEEGGNCHLQDMTVMTGHSFRRYRFTKRTHRNQDLGPFISHEMNRCI
ACYRCVRYYKDYADGTDLGVYGAHDNVYFGRPEDGTLESEFSGNLVEICPTGVFTDKTHSERYNRKWDMQFAPSIC
QQCSIGCNISPGERYGELRRIENRYNGTVNHYFLCDRGRFGYGYVNLKDRPRQPVQRRGDDFITLNAEQAMQGAAD
ILRQSKKVIGIGSPRASVESNFALRELVGEENFYTGIAHGEQERLQLALKVLREGGIYTPALREIESYDAVLVLGE
DVTQTGARVALAVRQAVKGKAREMAAAQKVADWQIAAILNIGQRAKHPLFVTNVDDTRLDDIAAWTYRAPVEDQAR
LGFAIAHALDNSAPAVDGIEPELQSKIDVIVQALAGAKKPLIISGTNAGSLEVIQAAANVAKALKGRGADVGITMI
ARSVNSMGLGIMGGGSLEEALTELETGRADAVVVLENDLHRHASAIRVNAALAKAPLVMVVDHQRTAIMENAHLVL
SAASFAESDGTVINNEGRAQRFFQVYDPAYYDSKTVMLESWRWLHSLHSTLLSREVDWTQLDHVIDAVVAKIPELA
GIKDAAPDATFRIRGQKLAREPHRYSGRTAMRANISVHEPRQPQDIDTMFTFSMEGNNQPTAHRSQVPFAWAPGWN
SPQAWNKFQDEVGGKLRFGDPGVRLFETSENGLDYFTSVPARFQPQDGKWRIAPYYHLFGSDELSQRAPVFQSRMP
QPYIKLNPADAAKLGVNAGTRVSFSYDGNTVTLPVEIAEGLTAGQVGLPMGMSGIAPVLAGAHLEDLKEAQQ
```

TABLE 3-continued

Respiratory Complex I proteins *Escherichia coli* (strain K12)

| UNIPROT ID | Name | SEQ ID NO |
|---|---|---|

P0AFD4 NADH-quinone oxidoreductase subunit H; 325 residues   SEQ ID NO: 28
MSWISPELIEILLTILKAVVILLVVVTCGAFMSFGERRLLGLVGWGGSLQLVADMIKMFFKEDWIPK
FSDRVIFTLAPMIAFTSLLLAFAIVPVSPGWVVADLNIGILFFLMMAGLAVYAVLFAGWSSNNKYSLLGAMRASAQ
TLSYEVFLGLSLMGVVAQAGSFNMTDIVNSQAHVWNVIPQFFGFITFAIAGVAVCHRHPFDQPEAEQELADGYHIE
YSGMKFGLFFVGEYIGIVTISALMVTLFFGGWQGPLLPPFIWFALKTAFFMMMFILIRASLPRPRYDQVMSFGWKI
CLPLTLINLLVTAAVILWQAQ P0AFD6 NADH-quinone oxidoreductase subunit I; 180 residues   SEQ ID NO: 29
MTLKELLVGFGTQVRSIWMIGLHAFAKRETRMYPEEPVYLPPRYRGRIVLTRDPDGEERCVACNLCAVACPVGCIS
LQKAETKDGRWYPEFFRINFSRCIFCGLCEEACPTTAIQLTPDFEMGEYKRQDLVYEKEDLLISGPGKYPEYNFYR
MAGMAIDGKDKGEAENEAKPIDVKSLLP P0AFE0 NADH-quinone oxidoreductase subunit J; 184 residues   SEQ ID NO: 30
MEFAFYICGLIAILATLRVITHINPVHALLYLIISLLAISGVFFSLGAYFAGALEIIVYAGAIMVLFVFVVMMLNL
GGSEIEQERQWLKPQVWIGPAILSAIMLVVIVYAILGVNDQGIDGTPISAKAVGITLFGPYVLAVELASMLLLAGL
VVAFHVGREERAGEVLSNRKDDSAKRKTEEHA P0AFE4 NADH-quinone oxidoreductase subunit K; 100 residues   SEQ ID NO: 31
MIPLQHGLILAAILFVLGLTGLVIRRNLLFMLIGLEIMINASALAFVVAGSYWGQTDGQVMYILAISLAAAEASIG
LALLLQLHRRRQNLNIDSVSEMRG P33607 NADH-quinone oxidoreductase subunit L; 613 residues   SEQ ID NO: 32
MNMLALTIILPLIGFVLLAFSRGRWSENVSAIVGVGSVGLAALVTAFIGVDFFANGEQTYSQPLWTWMSVGDFNIG
FNLVLDGLSLTMLSVVTGVGFLIHMYASWYMRGEEGYSRFFAYTNLFIASMVVLVLADNLLLMYLGWEGVGLCSYL
LIGFYYTDPKNGAAAMKAFVVTRVGDVFLAFALFILYNELGTLNFREMVELAPAHFADGNNMLMWATLMLLGGAVG
KSAQLPLQTWLADAMAGPTPVSALIHAATMVTAGVYLIARTHGLFLMTPEVLHLVGIVGAVTLLLAGFAALVQTDI
KRVLAYSTMSQIGYMFLALGVQAWDAAIFHLMTHAFFKALLFLASGSVILACHHEQNIFKMGGLRKSIPLVYLCFL
VGGAALSALPLVTAGFFSKDEILAGAMANGHINLMVAGLVGAFMTSLYTFRMIFIVFHGKEQIHAHAVKGVTHSLP
LIVLLILSTFVGALIVPPLQGVLPQTTELAHGSMLTLEITSGVVAVVGILLAAWLWLGKRTLVTSIANSAPGRLLG
TWWYNAWGFDWLYDKVFVKPFLGIAWLLKRDPLNSMMNIPAVLSRFAGKGLLLSENGYLRWYVASMSIGAVVVLAL
LMVLR P0AFE8 NADH-quinone oxidoreductase subunit M; 409 residues   SEQ ID NO: 33
MLLPWLILIPFIGGFLCWQTERFGVKVPRWIALITMGLTLALSLQLWLQGGYSLTQSAGIPQWQSEFDMPWIPRFG
ISIHLAIDGLSLLMVVLTGLLGVLAVLCSWKEIEKYQGFFHLNLMWILGGVIGVFLAIDMFLFFFFWEMMLVPMYF
LIALWGHKASDGKTRITAATKFFIYTQASGLVMLIAILALVFVHYNATGVWTFNYEELLNTPMSSGVEYLLMLGFF
IAFAVKMPVVPLHGWLPDAHSQAPTAGSVDLAGILLKTAAYGLLRFSLPLFPNASAEFAPIAMWLGVIGIFYGAWM
APAQTDIKRLIAYTSVSHMGFVLIAIYTGSQLAYQGAVIQMIAHGLSAAGLFILCGQLYERIHTRDMRMMGGLWSK
MKWLPALSLFFAVATLGMPGTGNFVGEFMILFGSFQVVPVITVISTFGLVFASVYSLAMLHRAYFGKAKSQIASQE
LPGMSLRELFMILLLVVLLVLLGFYPQPILDTSHSAIGNIQQWFVNSVTTTRP P0AFF0 NADH-quinone oxidoreductase subunit N; 485 residues   SEQ ID NO: 34
MTITPQNLIALLPLLIVGLTVVVVMLSIAWRRNHFLNATLSVIGLNAALVSLWFVGQAGAMDVTPLMRVDGFAMLY
TGLVLLASLATCTFAYPWLEGYNDNKDEFYLLVLIAALGGILLANANHLASLFLGIELISLPLFGLVGYAFRQKRS
LEASIKYTILSAAASSFLLFGMALVYAQSGDLSFVALGKNLGDGMLNEPLLLAGFGLMIVGLGFKLSLVPFHLWTP
DVYQGAPAPVSTFLATASKIAIFGVVMRLFLYAPVGDSEAIRVVLAIIAFASIIFGNLMALSQINIKRLLGYSSIS
HLGYLLVALIALQTGEMSMEAVGVYLAGYLFSSLGAFGVVSLMSSPYRGPDADSLFSYRGLFWHRPILAAVMTVMM
LSLAGIPMTLGFIGKFYVLAVGVQAHLWWLVGAVVVGSAIGLYYYLRVAVSLYLHAPEQPGRDAPSNWQYSAGGIV
VLISALLVLVLGVWPQPLISIVRLAMPLM Other protein complexes are useful for the artificial cell free organelle systems described herein. For example, Photosystem II complexes from *Thermosynechococcus elongatus* (PBD ID: 2AXT), *Thermosynechococcus vulcanus* (PDB ID: 3WU2), *Pisum sativum* (PDB ID: 5XNL), *Chlamydomonas reinhardtii* (PDB ID: 6KAD), *Spinacia oleracea* (PDB ID: 3JCU), and *Arabidopsis thaliana* (PDB ID: 5M DX) have solved biomolecular structures and can be purified to homogeneity [56-62]; the polypeptide sequences of the structures in the indicated Protein Data Base accession numbers and publication references are incorporated by reference herein for such teachings. Similarly, oxidoreductase complex I structures have been solved for *Thermus thermophilus* (PDB ID 3IAM), *Vibrio cholerae* (PDB ID 4P6V), *Yarrowia lipolytica* (PDB ID: 6RFR), *Ova aries* (PDB ID: 6ZKJ), *Bos taurus* (PDB ID: 5LDX), *Mus musculus* (PDB ID: 6ZTQ), and *Homo sapiens* (PDB ID: 5XTD) [63-68]; the polypeptide sequences of the structures in the indicated Protein Data Base accession numbers and publication references are incorporated by reference herein for such teachings. Other homologous PSII, bacteriorhodopsin, and oxidoreductase complex I proteins and protein complexes may be used in the cell free organelle systems described herein.

The proteins and protein complexes for the photosynthetic proteins or oxidoreductase proteins can be purified from their natural organisms or recombinantly expressed in typical expression organisms. Generally, with complex multi-protein complexes, it is preferable to purify the protein complex from the natrual source.

In one embodiment described herein, the artificial cell free organelle system is reconstituted with a light harvesting or photosynthetic protein or protein complex from one organsim and an oxidoreductase protein or protein complex from another organism. Each protein or protein complex is vectorially incorporated into an artificial membrane system.

This permits precise control of the reconstitution stoichiometry, the membrane composition, buffer systems, and concentrations of the enzymatic cofactors such as ubiquinone, ubiquinol or analogues thereof and $NAD^+$, $NADP^+$, NADH, NADPH, or analogues thereof.

In one embodiment, the artificial cell free organelle system uses ubiquinone or an analogue thereof as an enzymatic cofactor or coenzyme. In another embodiment, the system uses ubiquinol, decylubiquinol, or an analogue of ubiquinol as a coenzyme.

In another embodiment, the artificial cell free organelle system uses $NAD^+$, NADH, or an analogue thereof as an enzymatic cofactor or coenzyme. In another embodiment, the enzymatic cofactor is $NADP^+$, NADPH (nicotinamide adenine dinucleotide phosphate), or an analogue thereof. For example, some researchers have produced CMI containing point mutations that increase its affinity for binding $NADP^+$/NADPH over $NAD^+$/NADH [33], and such constructs can be used to regenerate NADPH in the same manner as described with reference to the exemplary embodiment used to regenerate NADH. In one embodiment, the desired product of the artificial cell free organelle system is NADH, NADPH, or analogues thereof.

In one embodiment, water ($H_2O$) is used as the electron donor to regenerate the enzymatic cofactor. In another embodiment, oxygen ($O_2$) is essentially the only byproduct produced in the process of regenerating the enzymatic cofactor (e.g., NADH, NADPH, or analogues thereof).

In another embodiment, an ionophore, for example a potassium ionophore, is added to the reaction mixture to reduce the electrical component of the pH gradient produced by the photosynthetic reaction center, which in some embodiments allows a higher pH gradient to be established across the membrane. In another embodiment, the potassium ionophore is valinomycin. In other embodiments, the potassium ionophore is salinomycin. In other embodiments, the ionophore is lasalocid, ionomycin, nonactin, beauvericin, calcimycin, or the like.

Figure 1B:
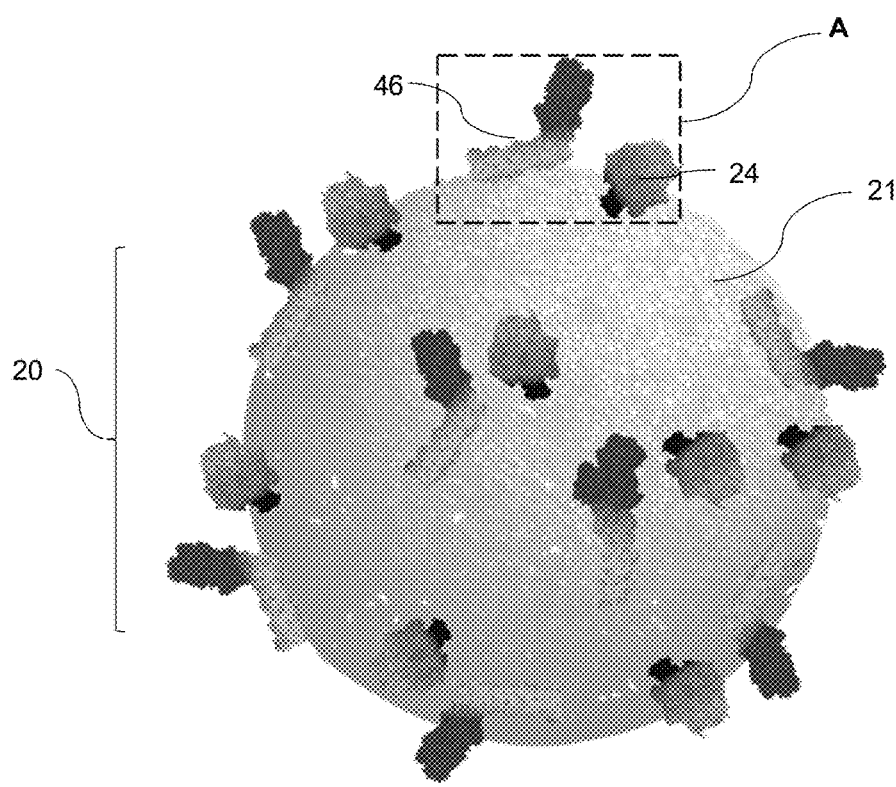
FIG. 1B shown an exemplary proteoliposome 20 comprising a membrane, which is a lipid bilayer 21 in the illustrated embodiment. The proteoliposome contains Photosystem II (PSII) 24 and Respiratory Complex I (CMI) 46 integrated into the phospholipid bilayer 21 of the membrane. An enlarged view of the area indicated as "A" is shown in FIG. 1C.
Figure 1C:
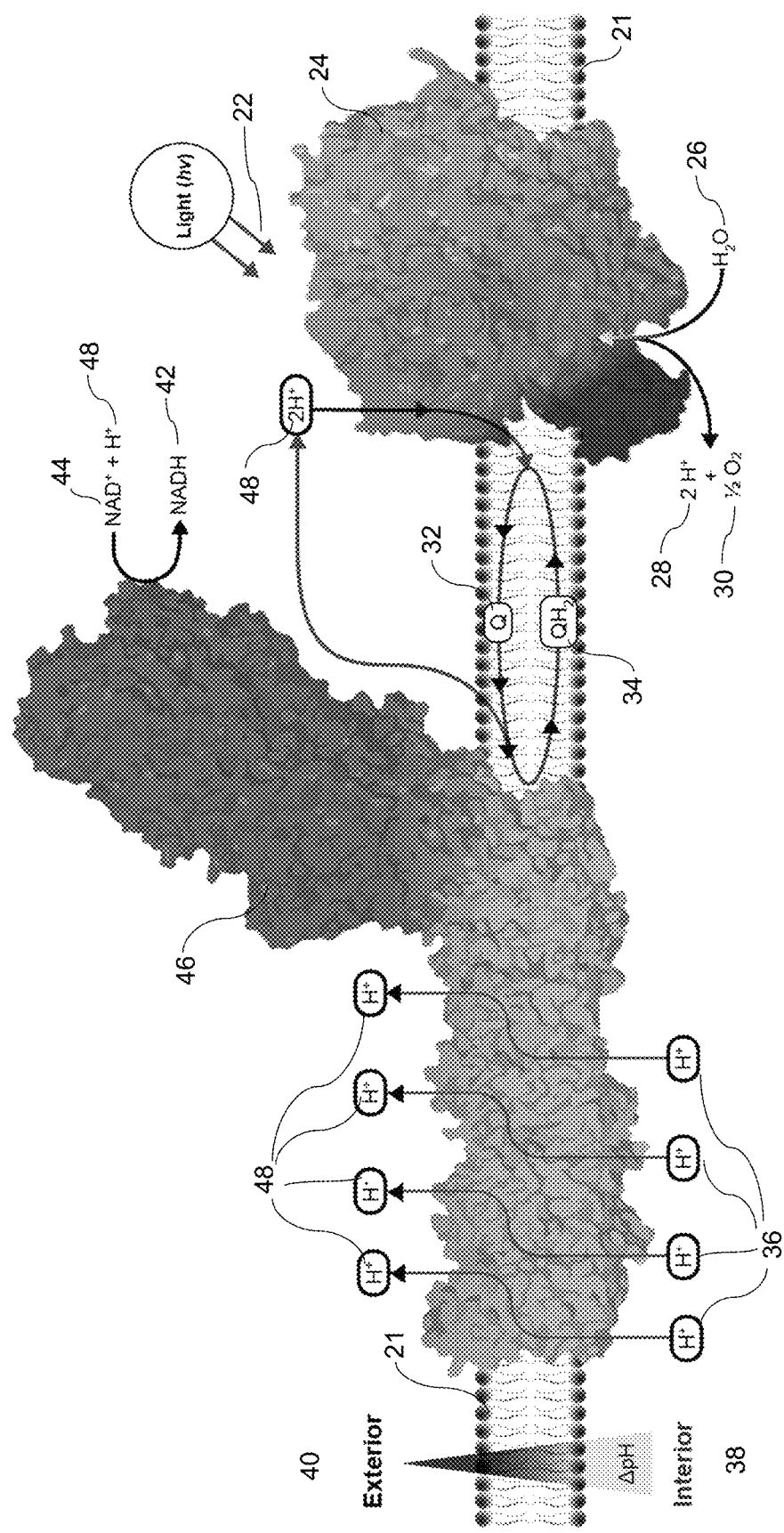
FIG. 1C shows an enlarged view of the "A" region of FIG. 1B and illustrates the specific reactions that occur on the interior 38 and exterior 40 of the phospholipid bilayer 21 of the membrane. PSII 24 harvests light energy 22, splitting water 26 to oxygen 30 and protons 28 on the inside 38 of the proteoliposome; electrons are transferred from water 26 to Q 32 to form $QH_2$ 34 within the lipid bilayer 21 of the proteoliposome. The production of 4 protons in the interior of the proteoliposomes by PSII 24 generates a PMF driving the reverse reaction of CMI 46. CMI 46 oxidizes the $QH_2$ 34 produced by PSII 24 transferring the electrons and a proton 48 to $NAD^+$ 44 resulting in NADH 42, and the cycle repeats.

In one exemplary embodiment, Photosystem II (PSII) 24 and Respiratory Complex I (CMI) (NADH:ubiquinone oxidoreductase) 46 are integrated into liposomes to form proteoliposomes 20, resulting in an artificial organelle capable of $NAD^+$ photoreduction (see FIG. 1A-C, with an enlarged view of FIG. 1B, region A provided in FIG. 1C). PSII 24 harvests light energy 22, splitting water 26 to oxygen 30 and protons 28 on the inside 38 of the proteoliposome; electrons are transferred from water 26 to Q 32 to form $QH_2$ 34 within the lipid bilayer 21 of the proteoliposome. The production of 4 protons in the interior of the proteoliposomes by PSII 24 generates a PMF driving reverse electron transfer of CMI 46. CMI 46 oxidizes the $QH_2$ 34 produced by PSII 24 transferring the electrons and a proton 48 to $NAD^+$44 resulting in NADH 42 and the cycle repeats.

In more detail, the proteoliposomes 20 comprise a membrane, which is a lipid bilayer 21 in the illustrated embodiment (FIG. 1B). Photons 22 harvested by PSII 24 result in water oxidation generating oxygen and protons as part of the process (illustrated in FIG. 1A as one molecule of $H_2O$ (26) yielding 2 $H^+$ (28) +½ $O_2$ (30) in the inside 38 of the proteoliposomes). The electrons from water are transferred to ubiquinone (Q) (32) within the lipid bilayer 21, producing ubiquinol ($QH_2$) (34) [34-35].

The accumulation of protons 36 on the inside 38 of the lipid bilayer 21 as compared with the outside 40 of the lipid bilayer 21 generates a proton motive force (PMF) that diminishes the thermodynamic gap of the standard redox potentials between NADH/$NAD^+$ (42/44) and $QH_2$/Q (34/32) to permit reverse electron transfer (RET) from $QH_2$ 34 to $NAD^+$44 by CMI 46 [36] as protons 36 from the inside 38 of the lipid bilayer 21 are pumped through CMI 46 to the outside 40 of the lipid bilayer 21 (illustrated as protons 48). By artificially coupling the associated metabolisms of these two enzymes, NADH 48 is produced from $NAD^+$ using light 22 and water 26 as substrates, with oxygen 30 as the only by-product. While $NAD^+$/NADH are used as exemplary coenzymes in FIG. 1A-C, $NAD^+$/NADH, $NADP^+$/NAPH, or analogues thereof can be used in the systems described herein. Similarly, ubiquinone, ubiquinol, or analogues thereof can be used in the systems described herein.

In another embodiment, the artificial cell free organelle system comprises an enzymatic cofactor regeneration system, for example in the form of proteoliposomes 20, is incorporated into or supplied to a primary reaction system that requires the regeneration of spent NADH or NADPH (e.g., $NAH^+$, $NADP^+$, or analogues thereof). Examples of reaction systems that require regeneration of NADH, NADPH, or analogues thereof include diketoreductase, ketoreductase, oxidoreductase, aminoacid dehydrogenases, transaminases, and alpha-transaminase. See e.g., Bezborodov and Zagustina [37].

In another embodiment, supplying the engineered enzymatic cofactor regeneration system to the primary reaction system comprises adding an artificial organelle comprising a membrane, a photosynthetic reaction center (e.g., PSII) and an oxidoreductase enzyme (e.g., CMI) as described herein to the primary reaction system. In another embodiment, ubiquinol or an analogue thereof are incorporated into the membrane of the artificial organelle. In another embodiment, an ionophore, optionally a potassium ionophore, is also supplied to the primary reaction system. By applying light to the primary reaction system incorporating the artificial organelle, the artificial organelle is able to regenerate NADH, NADPH, or analogues thereof for use by the primary reaction system. Because the artificial organelle uses water as the source of electrons and produces only oxygen as a byproduct, use of the artificial organelle is unlikely to interfere with the primary reaction system.

One embodiment described herein is an artificial cell free organelle system comprising: a membrane having two sides comprising an inner surface in contact with an inner aqueous medium and an outer surface in contact with an outer aqueous medium; one or more photosynthetic proteins and one or more oxidoreductase proteins are vectorially embedded within and traversing the membrane; one or more first redox active cofactors; one or more second redox active cofactors; water, and a photon energy source; wherein: when one or more photons are directed on the one or more photosynthetic proteins, the photosynthetic proteins harvest the photon energy and catalyze the oxidation of at least one water molecule in the inner aqueous medium, generating 0.5 equivalents of oxygen gas and yielding up to two protons and two electrons per two photons that are transferred to an oxidized form of the first redox active cofactor, generating a reduced form of the first redox active cofactor; the accumulation of protons in the inner aqueous medium generates a proton concentration gradient between the inner aqueous medium and the outer aqueous medium; and the one or more oxidoreductase proteins pumps protons from the inner aqueous medium through the membrane to the outer aqueous medium to reduce the proton concentration gradient and simultaneously catalyzes the transfer of electrons from the reduced first redox cofactor to an oxidized form of the second redox active cofactor, generating a reduced form of the second redox active cofactor and an oxidized form of the first redox active cofactor. In one aspect, the membrane comprises a biomimetic bilayer, a biomimetic three-dimensional bilayer, a unilamellar liposome, a planar membrane, or a membraneous polymer construct. In another aspect, the membraneous polymer construct comprises a triblock copolymer membrane comprising varying lengths of poly(dimethylsiloxane) (PDMS) as the hydrophobic membrane-forming block and poly(2-methyloxazoline) (PMOXA) as the hydrophilic membrane-forming block. In another aspect, the membrane comprises a closed unilamellar liposome comprising a phospholipid bilayer. In another aspect, the one or more photosynthetic proteins and one or more oxidoreductase proteins are vectorially embedded in the membrane using a detergent. In another aspect, the detergent comprises one or more of CHAPS (3-[(3-cholamidopropyl) dimethylammonio]-1-propanesulfonate), DDM (n-dodecyl-β-D-maltoside), OG (octyl-β-D-glucopyranoside), or Triton X-100. In another aspect, the one or more photosynthetic proteins comprises the photosystem II complex of proteins and/or bacteriorhodopsin. In another aspect, the photosystem II complex of proteins comprises the photosystem II complexes from *Cyanobacterium synechocystis, Synechocystis* sp., *Synechococcus elongates, Thermosynechococcus elongatus, Thermosynechococcus vulcans, Pisum sativum, Chlamydomonas reinhardtii, Spinacia oleracea,* or *Arabidopsis thaliana*; and the bacteriorhodopsin comprises the bacteriorhodopsin from *Halobacterium salinarum*. In another aspect, the photosystem II complex of proteins or bacteriorhodopsin are purified or recombinant.

In another aspect, the one or more photosynthetic proteins comprise the photosystem II complex of proteins from *Synechocystis* sp. PCC6803. In another aspect, the one or more oxidoreductase enzymes comprises the Respiratory Complex I complex of proteins. In another aspect, the Respiratory Complex I complex of proteins comprises the Respiratory Complex I of *Eschericia coli, Thermus thermophilus, Vibrio cholerae, Yarrowia lipolytica, Ovis aries, Bos taurus, Mus musculus,* or *Homo sapiens*. In another aspect, the Respiratory Complex I complex of proteins are purified or recombinant. In another aspect, the one or more oxidoreductase enzymes comprises the Respiratory Complex I complex of proteins from *E. coli*. In another aspect, the one or more oxidoreductase enzymes comprises a Respiratory Complex I that has been engineered to preferentially reduce NADPH. In another aspect, the one or more oxidoreductase enzymes are vectorially incorporated into the membrane in an orientation opposite to the orientation of the oxidoreductase enzyme in vivo. In another aspect, the first redox active cofactor comprises ubiquinone or a ubiquinone analogue. In another aspect, the ubiquinone analogue has the structure:

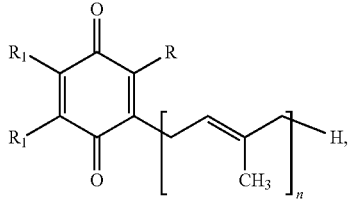

wherein R is methyl, hydroxyl, or hydrogen and $R_1$ is independently methoxy, methyl, hydroxyl or hydrogen, and n is an integer between 0 to 20, 6 to 12, or 7 to 10, including all integers within the specified ranges. In another aspect, the second redox active cofactor comprises $NAD^+$, $NADP^+$, an $NAD^+$ analogue, or an $NADP^+$ analogue. In another aspect, the $NAD^+$ or $NADP^+$ analogue has the structure:

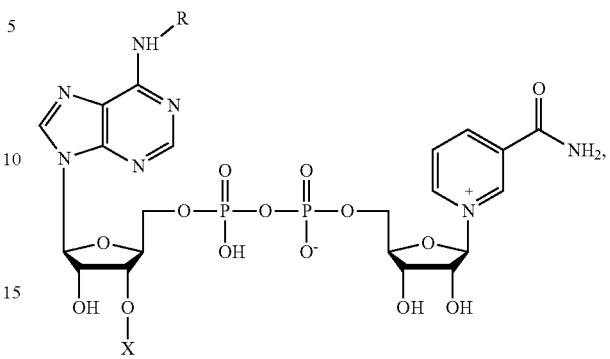

where R is a polyethylene glycol of 100 to 10,000 MW, a carbohydrate moiety or a polypeptide, and X is phosphate or hydrogen. In another aspect, the reduced form of the first redox active cofactor comprises ubiquinol, decylubiquinol, or a ubiquinol analogue. In another aspect, the ubiquinol analogue has the structure:

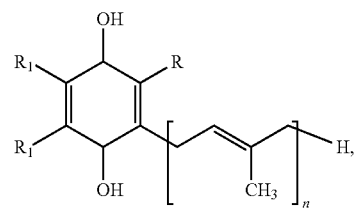

wherein R is methyl, hydroxyl, or hydrogen and $R_1$ is independently methoxy, methyl, hydroxyl or hydrogen, and n is an integer between 0 to 20, 6 to 12, or 7 to 10, including all integers within the specified ranges. In another aspect, the reduced form of the second redox active cofactor comprises NADH, NADPH, or an analogue thereof. In another aspect, the NADH or NADPH analogue has the structure:

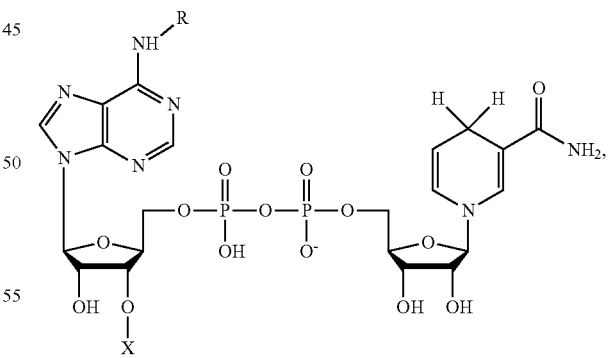

where R is a polyethylene glycol of 100 to 10,000 MW, a carbohydrate moiety, or a polypeptide, and X is phosphate or hydrogen. In another aspect, the system further comprises an ionophore comprising one or more of valinomycin, salinomycin, lasalocid, ionomycin, nonactin, beauvericin, or calcimycin. In another aspect, the system further comprises an ionophore comprising a potassium ionophore, and wherein the potassium ionophore comprises valinomycin or salinomycin.

Another embodiment described herein is a method or means for converting light energy and water into oxygen and reduced NADH, NADPH, or analogues thereof using artificial photosynthesis in an artificial cell free system, the method comprising: (a) providing an artificial cell free organelle system comprising: a membrane having two sides comprising an inner surface in contact with an inner aqueous medium and an outer surface in contact with an outer aqueous medium; one or more photosynthetic proteins comprising photosystem II or bacteriorhodopsin vectorially embedded within and traversing the membrane; one or more oxidoreductase proteins comprising Respiratory Complex I vectorially embedded within and traversing the membrane; ubiquinone or an analogue thereof; $NAD^+$, $NADP^+$ or an analogue thereof; water, and a photon energy source; (b) directing one or more photons to the one or more photosynthetic proteins; (c) the one or more photosynthetic proteins catalyzes the electron transfer from photon energy to ubiquinone or an analogue thereof, generating ubiquinol or an analogue thereof; and (d) the one or more oxidoreductase proteins catalyzes the electron transfer from ubiquinol or an analogue thereof to $NAD^+$, $NADP^+$, or analogues thereof, producing NADH, NADPH, or analogues thereof, and oxidizing ubiquinol or analogue thereof to ubiquinone or an analogue thereof. In one aspect, wherein: when one or more photons are directed on the one or more photosynthetic proteins, the photosynthetic proteins harvest the photon energy and catalyze the oxidation of at least one water molecule in the inner aqueous medium, generating 0.5 equivalents of oxygen gas and yielding up to two protons and two electrons per two photons that are transferred to ubiquinone or an analogue thereof, generating ubiquinol or an analogue thereof; the accumulation of protons in the inner aqueous medium generates a proton concentration gradient between the inner aqueous medium and the outer aqueous medium; and the oxidoreductase enzyme comprising Respiratory Complex I pumps protons from the inner aqueous medium through the membrane to the outer aqueous medium to reduce the proton concentration gradient and simultaneously catalyzes the transfer of electrons from ubiquinol or an analogue thereof to $NAD^+$, $NADP^+$, or analogues thereof, producing NADH, NADPH, or analogues thereof, and oxidizing ubiquinol or analogue thereof back to ubiquinone or a ubiquinone or an analogue thereof. In another aspect, the membrane comprises a biomimetic bilayer, a biomimetic three-dimensional bilayer, a unilamellar liposome, a planar membrane, or a membraneous polymer construct. In another aspect, the membraneous polymer construct comprises a triblock co-polymer membrane comprising varying lengths of poly(dimethylsiloxane) (PDMS) as the hydrophobic membrane-forming block and poly(2-methyloxazoline) (PMOXA) as the hydrophilic membrane-forming block. In another aspect, the membrane comprises a closed unilamellar liposome comprising a phospholipid bilayer. In another aspect, the one or more photosynthetic proteins and one or more oxidoreductase proteins are vectorially embedded in the membrane using a detergent. In another aspect, the detergent comprises one or more of CHAPS (3-[(3-cholamidopropyl)dimethylammonio]-1-propanesulfonate), DDM (n-dodecyl-β-D-maltoside), OG (octyl-β-D-glucopyranoside), or Triton X-100. In another aspect, the photosystem II complex of proteins comprises the photosystem II complexes from *Cyanobacterium synechocystis*, *Synechococcus elongates*, *Thermosynechococcus elongatus*, *The rmosynechococcus vulcans*, *Pisum sativum*, *Chlamydomonas reihhardtii*, *Spinacia oleracea*, or *Arabidopsis thaliana*; and the bacteriorhodopsin comprises the bacteriorhodopsin from *Halobacterium salinarum*. In another aspect, the photosystem II complex of proteins or bacteriorhodopsin are purified or recombinant. In another aspect, the one or more photosynthetic proteins comprise the photosystem II complex of proteins from *Cyanobacterium synechocystis*. In another aspect, the Respiratory Complex I complex of proteins comprises the Respiratory Complex I of *Eschericia coli*, *Thermus thermophilus*, *Vibrio cholerae*, *Yarrowia lipolytica*, *Ovis aries*, *Bos taurus*, *Mus musculus*, or *Homo sapiens*. In another aspect, the Respiratory Complex I complex of proteins are purified or recombinant. In another aspect, the one or more oxidoreductase enzymes comprises the Respiratory Complex I complex of proteins from *E. coli*. In another aspect, the one or more oxidoreductase enzymes comprises a Respiratory Complex I that has been engineered to preferentially reduce NADPH or an analogue thereof. In another aspect, the one or more oxidoreductase enzymes are vectorially incorporated into the membrane in an orientation opposite to the orientation of the oxidoreductase enzyme in vivo. In another aspect, the ubiquinone analogue has the structure:

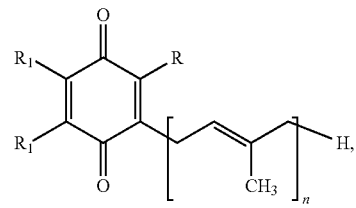

wherein R is methyl, hydroxyl, or hydrogen and $R_1$ is independently methoxy, methyl, hydroxyl or hydrogen, and n is an integer between 0 to 20, 6 to 12, or 7 to 10, including all integers within the specified ranges. In another aspect, the $NAD^+$ or $NADP^+$ analogue has the structure:

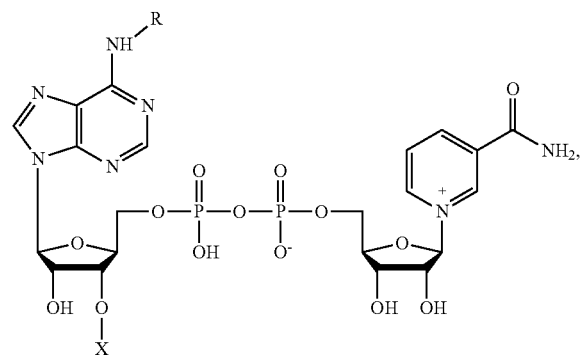

where R is a polyethylene glycol of 100 to 10,000 MW, a carbohydrate moiety or a polypeptide, and X is phosphate or hydrogen. In another aspect, the ubiquinol analogue has the structure:

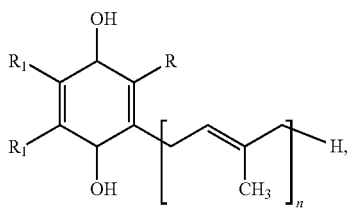

wherein R is methyl, hydroxyl, or hydrogen and $R_1$ is independently methoxy, methyl, hydroxyl or hydrogen, and n is an integer between 0 to 20, 6 to 12, or 7 to 10, including all integers within the specified ranges. In another aspect, the NADH or NADPH analogue has the structure:

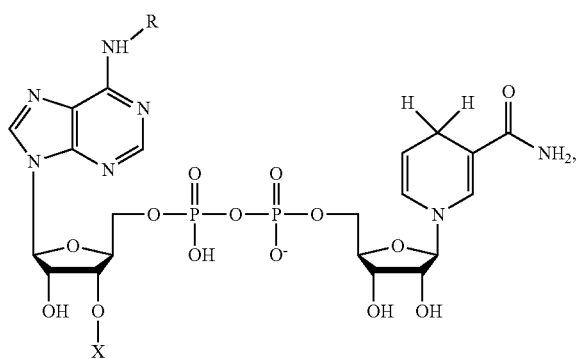

where R is a polyethylene glycol of 100 to 10,000 MW, a carbohydrate moiety, or a polypeptide, and X is phosphate or hydrogen. In another aspect, the method further comprises adding an ionophore comprising one or more of valinomycin, salinomycin, lasalocid, ionomycin, nonactin, beauvericin, or calcimycin. In another aspect, the method further comprises adding an ionophore comprising a potassium ionophore, and wherein the potassium ionophore comprises valinomycin or salinomycin.

Another embodiment described herein is NADH, NADPH, or analogues thereof produced by the methods described herein.

Another embodiment described herein is the use of an artificial cell free organelle system for converting light energy and water into oxygen and reduced NADH, NADPH, or analogues thereof using artificial photosynthesis in an artificial cell free system. In one aspect, the artificial cell free organelle system comprises: a membrane having two sides comprising an inner surface in contact with an inner aqueous medium and an outer surface in contact with an outer aqueous medium; one or more photosynthetic proteins comprising photosystem II or bacteriorhodopsin vectorially embedded within and traversing the membrane; one or more oxidoreductase proteins comprising Respiratory Complex I vectorially embedded within and traversing the membrane; ubiquinone or an analogue thereof; $NAD^+$, $NADP^+$ or an analogue thereof; water, and a photon energy source; wherein: the one or more photosynthetic proteins catalyzes the electron transfer from photon energy to ubiquinone or an analogue thereof, generating ubiquinol or an analogue thereof; and the one or more oxidoreductase proteins catalyzes the electron transfer from ubiquinol or an analogue thereof to $NAD^+$, $NADP^+$, or analogues thereof, producing NADH, NADPH, or analogues thereof, and oxidizing ubiquinol or analogue thereof to ubiquinone or an analogue thereof.

Further embodiments described herein include nucleic acid molecules comprising polynucleotides having nucleotide sequences about 50%, 55%, 60%, 65%, 70%, 75%, 80%, 85%, 90%, 91%, 92%, 93%, 94%, 95%, 96%, 97%, 98%, or 99% identical, and more preferably at least about 90-99% or 100% identical to (a) nucleotide sequences, or degenerate, homologous, or codon-optimized variants thereof, encoding polypeptides having the amino acid sequences in SEQ ID NO: 1-34; (b) nucleotide sequences, or degenerate, homologous, or codon-optimized variants thereof, encoding polypeptides having the amino acid sequences in SEQ ID NO: 1-34; and (c) nucleotide sequences capable of hybridizing to the complement of any of the nucleotide sequences in (a) or (b) above and capable of expressing functional polypeptides of amino acid sequences in SEQ ID NO: 1-34.

By a polynucleotide having a nucleotide sequence at least, for example, 90-99% "identical" to a reference nucleotide sequence encoding a protein as described herein is intended that the nucleotide sequence of the polynucleotide be identical to the reference sequence except that the polynucleotide sequence can include up to about 10 to 1 point mutations, additions, or deletions per each 100 nucleotides of the reference nucleotide sequence encoding the proteins described herein.

In other words, to obtain a polynucleotide having a nucleotide sequence about at least 90-99% identical to a reference nucleotide sequence, up to 10% of the nucleotides in the reference sequence can be deleted, added, or substituted, with another nucleotide, or a number of nucleotides up to 10% of the total nucleotides in the reference sequence can be inserted into the reference sequence. These mutations of the reference sequence can occur at the 5'- or 3'-terminal positions of the reference nucleotide sequence or anywhere between those terminal positions, interspersed either individually among nucleotides in the reference sequence or in one or more contiguous groups within the reference sequence. The same is applicable to polypeptide sequences about at least 90-99% identical to a reference polypeptide sequence.

As noted above, two or more polynucleotide sequences can be compared by determining their percent identity. Two or more amino acid sequences likewise can be compared by determining their percent identity. The percent identity of two sequences, whether nucleic acid or peptide sequences, is generally described as the number of exact matches between two aligned sequences divided by the length of the shorter sequence and multiplied by 100. An approximate alignment for nucleic acid sequences is provided by the local homology algorithm of Smith and Waterman, *Advances in Applied Mathematics* 2: 4 82-489 (1981). This algorithm can be extended to use with peptide sequences using the scoring matrix developed by Dayhoff, *Atlas of Protein Sequences and Structure*, M. O. Dayhoff ed., 5 suppl. 3: 353-358, National Biomedical Research Foundation, Washington, D.C., USA, and normalized by Gribskov, *Nucl. Acids Res.* 14(6): 6745-6763 (1986).

For example, due to the degeneracy of the genetic code, one having ordinary skill in the art will recognize that a large number of the nucleic acid molecules having a sequence at least 50%, 55%, 60%, 65%, 70%, 75%, 80%, 85%, 90%, 91%, 92%, 93%, 94%, 95%, 96%, 97%, 98%, 99%, or 100% identical to the nucleic acid sequences encoding the polypeptides shown in SEQ ID NO: 1-34, or degenerate, homologous, or codon-optimized variants thereof, will encode a protein described herein.

The polynucleotides described herein include those encoding mutations, variations, substitutions, additions, deletions, and particular examples of the polypeptides described herein. For example, guidance concerning how to make phenotypically silent amino acid substitutions is provided in Bowie et al., "Deciphering the Message in Protein Sequences: Tolerance to Amino Acid Substitutions," *Science* 247: 1306-1310 (1990), wherein the authors indicate that proteins are surprisingly tolerant of amino acid substitutions.

Thus, fragments, derivatives, or analogs of the polypeptides of SEQ ID NO: 1-34 can be (i) ones in which one or more of the amino acid residues (e.g., 1, 2, 3, 4, 5, 7, 8, 9, 10, 11, 12, 13, 14, 15, 16, 17, 18, 19, 20, 25, 30, 35, 40, 45, or 50 residues, or even more) are substituted with a conserved or non-conserved amino acid residue (preferably a conserved amino acid residue). Such substituted amino acid residues may or may not be one encoded by the genetic code, or (ii) ones in which one or more of the amino acid residues includes a substituent group (e.g., 1, 2, 3, 4, 5, 7, 8, 9, 10, 15, 20, 25, 30, 35, 40, 45, or 50 residues or even more), or (iii) ones in which the mature polypeptide is fused with another polypeptide or compound, such as a compound to increase the half-life of the polypeptide (for example, polyethylene glycol), or (iv) ones in which the additional amino acids are fused to the mature polypeptide, such as an IgG Fc fusion region peptide or leader or secretory sequence or a sequence which is employed for purification of the mature polypeptide or a proprotein sequence. Such fragments, derivatives, and analogs are deemed to be within the scope of those skilled in the art from the teachings herein.

In addition, fragments, derivatives, or analogs of the polypeptides of SEQ ID NO: 1-34 can be substituted with one or more conserved or non-conserved amino acid residue (preferably a conserved amino acid residue). In some cases these polypeptides, fragments, derivatives, or analogs thereof will have a polypeptide sequence at least 50%, 55%, 60%, 65%, 70%, 75%, 80%, 85%, 90%, 91%, 92%, 93%, 94%, 95%, 96%, 97%, 98%, 99% or 100% identical to the polypeptide sequence shown in SEQ ID NO: 1-34 and will comprise functional or non-functional proteins or enzymes. Similarly, additions or deletions to the polypeptides can be made either at the N- or C-termini or within non-conserved regions of the polypeptide (which are assumed to be non-critical because they have not been photogenically conserved).

As described herein, in many cases the amino acid substitutions, mutations, additions, or deletions are preferably of a minor nature, such as conservative amino acid substitutions that do not significantly affect the folding or activity of the protein or additions or deletions to the N- or C-termini. Of course, the number of amino acid substitutions, additions, or deletions a skilled artisan would make depends on many factors, including those described herein. Generally, the number of substitutions, additions, or deletions for any given polypeptide will not be more than about 100, 90, 80, 70, 60, 50, 40, 30, 25, 20, 19, 18, 17, 16, 15, 14, 13, 12, 11, 10, 9, 8, 7, 5, 6, 4, 3, 2, or 1.

Another embodiment described herein is a reaction mixture for reducing a spent enzymatic cofactor to yield a regenerated enzymatic cofactor upon exposure to light, the reaction mixture comprising: an engineered enzymatic cofactor regeneration system comprising: a membrane; a photosynthetic reaction center vectorially incorporated in the membrane; an oxidoreductase enzyme vectorially incorporated into the membrane; ubiquinol (2,3-dimethoxy-5-methyl-6-poly prenyl-1,4-benzoquinol) or an analogue thereof; and water ($H_2O$). In one aspect, the membrane comprises first and second hydrophilic layers surrounding an interior hydrophobic layer. In another aspect, the membrane comprises a lipid bilayer or a triblock co-polymer membrane. In another aspect, the membrane comprises a biomimetic membrane. In another aspect, the triblock co-polymer membrane comprises varying lengths of poly(dimethylsiloxane) (PDMS) as the hydrophobic membrane-forming block and poly(2-methyloxazoline) (PMOXA) as the hydrophilic membrane-forming block. In another aspect, the photosynthetic reaction center comprises photosystem II from any species. In another aspect, the photosynthetic reaction center comprises a thermostable photosystem II. In another aspect, the oxidoreductase enzyme comprises respiratory complex I. In another aspect, the respiratory complex I comprises respiratory complex I from any species. In another aspect, the respiratory complex I comprises a thermostable respiratory complex I. In another aspect, the oxidoreductase enzyme is vectorially incorporated into the membrane in an orientation opposite to the orientation of the oxidoreductase enzyme in vivo. In another aspect, the photosynthetic reaction center is vectorially incorporated in the membrane so that, upon exposure to light, the photosynthetic reaction center forms a proton gradient on a first side of the membrane. In another aspect, the oxidoreductase enzyme is vectorially incorporated in the membrane so that the oxidoreductase enzyme can carry out reverse electron transfer using the energy provided by the proton gradient by pumping protons from the first side of the membrane to a second side of the membrane. In another aspect, the membrane comprises a lipid bilayer, the engineered enzymatic cofactor regeneration system comprises proteoliposomes, and the photosynthetic reaction center and the oxidoreductase enzyme are vectorially incorporated into the membrane using CHAPS (3-[(3-cholamidopropyl)dimethylammonio]-1-propanesulfonate) as the detergent. In another aspect, the membrane comprises a triblock co-polymer membrane, and the engineered enzymatic cofactor regeneration system comprises vesicles formed from the membrane. In another aspect, the photosynthetic reaction center is vectorially incorporated into the proteoliposomes or the vesicles so that, upon exposure to light, the photosynthetic reaction center forms a proton gradient with an increased concentration of proteins on the inside of the proteoliposomes or vesicles. In another aspect, the oxidoreductase enzyme is vectorially incorporated in the proteoliposomes or the vesicles so that it can carry out reverse electron transfer using the energy provided by the proton gradient by pumping protons from the inside of the proteoliposomes or the vesicles to the outside of the proteoliposomes or the vesicles. In another aspect, the ubiquinol or analogue thereof comprises a compound having the following structure:

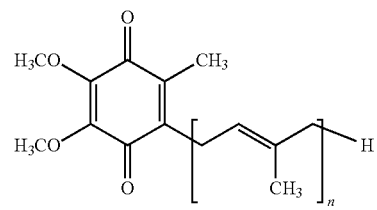

wherein n is an integer, wherein optionally n is between 0 and 20, or wherein optionally n is between 6 and 10, wherein optionally one or more of the methyl or methoxy substituents on the benzoquinone ring is absent or comprises a different substituent group, wherein optionally the ubiquinol or analogue thereof comprises ubiquinol or decylubiquinol. In another aspect, the spent enzymatic cofactor comprises $NAD^+$ or an analogue thereof and the regenerated enzymatic cofactor comprises NADH or an analogue thereof. In another aspect, the spent enzymatic cofactor comprises $NADP^+$ and the regenerated enzymatic cofactor comprises NADPH or an analogue thereof. In another aspect, the oxidoreductase enzyme comprises a respiratory complex 1 that has been engineered to preferentially reduce NADPH or an analogue thereof. In another aspect, the reaction mixture further comprises an ionophore, wherein the ionophore optionally comprises valinomycin, salinomycin, lasalocid, ionomycin, nonactin, beauvericin, or calcimycin. In another aspect, the ionophore comprises a potassium ionophore, and wherein the potassium ionophore optionally comprises valinomycin or salinomycin. In another aspect, the water ($H_2O$) supplies electrons to reduce the spent enzymatic cofactor upon exposure of the reaction mixture to light, and wherein essentially the only byproduct produced by the reaction mixture upon exposure to light is oxygen ($O_2$).

Another embodiment described herein is a method of regenerating a spent enzymatic cofactor using a reaction mixture as described herein, the method comprising: supplying the reaction mixture with the spent enzymatic cofactor; and supplying light to the reaction mixture. In one aspect, the reaction mixture further comprising: gathering energy from photons using the photosynthetic reaction center to cause the photosynthetic reaction center to transport protons across the membrane to form a proton gradient from a first side of the membrane to a second side of the membrane and reduce the ubiquinone or analogue thereof to ubiquinol or analogue thereof; and allowing the oxidoreductase enzyme to use energy provided by the proton gradient to carry out reverse electron transfer to reduce the spent enzymatic cofactor while oxidizing ubiquinol or analogue thereof to ubiquinone or analogue thereof.

Another embodiment described herein is a method of regenerating a spent enzymatic cofactor in a synthetic chemical process carried out in a primary reaction solution, the method comprising providing a reaction mixture as described herein in the primary reaction solution. In one aspect, the spent enzymatic cofactor comprises $NAD^+$, $NADP^+$ or analogues thereof.

Another embodiment described herein is an engineered enzymatic cofactor regeneration system comprising: a membrane; a photosynthetic reaction center vectorially incorporated in the membrane; and an oxidoreductase enzyme vectorially incorporated into the membrane.

Another embodiment described herein is an enzymatic cofactor regeneration system comprises one or more characteristics of the enzymatic cofactor regeneration system of the reaction mixture as described herein.

Another embodiment described herein is an artificial organelle for carrying out reduction of a spent enzymatic cofactor to produce a regenerated enzymatic cofactor, the artificial organelle comprising an engineered enzymatic cofactor regeneration system as described herein.

It will be apparent to one of ordinary skill in the relevant art that suitable modifications and adaptations to the compositions, formulations, methods, processes, apparata, assemblies, and applications described herein can be made without departing from the scope of any embodiments or aspects thereof. The compositions, apparata, assemblies, and methods provided are exemplary and are not intended to limit the scope of any of the disclosed embodiments. All the various embodiments, aspects, and options disclosed herein can be combined in any variations or iterations. The scope of the compositions, formulations, methods, apparata, assemblies, and processes described herein include all actual or potential combinations of embodiments, aspects, options, examples, and preferences described herein. The compositions, formulations, apparata, assemblies, or methods described herein may omit any component or step, substitute any component or step disclosed herein, or include any component or step disclosed elsewhere herein. The ratios of the mass of any component of any of the compositions or formulations disclosed herein to the mass of any other component in the formulation or to the total mass of the other components in the formulation are hereby disclosed as if they were expressly disclosed. Should the meaning of any terms in any of the patents or publications incorporated by reference conflict with the meaning of the terms used in this disclosure, the meanings of the terms or phrases in this disclosure are controlling. All patents and publications cited herein are incorporated by reference herein for the specific teachings thereof.

REFERENCES

A number of references are of interest with respect to the subject matter described herein.

1. Meyer et al., "The use of enzymes in organic synthesis and the life sciences: perspectives from the Swiss Industrial Biocatalysis Consortium (SIBC)," *Catal. Sci. Technol.* 3: 29-40 (2013).
2. Wu et al., "Methods for the regeneration of nicotinamide coenzymes," *Green Chem.* 15: 1773-1789 (2013).
3. Quinto et al., "Recent Trends in Biomimetic NADH Regeneration," *Top. Catal.* 57: 321-331 (2014).
4. Liu and Wang, "Cofactor regeneration for sustainable enzymatic biosynthesis," *Biotechnol. Adv.* 25: 369-384 (2007).
5. Uppada et al., "Cofactor regeneration—an important aspect of biocatalysis," *Curr. Sci. India* 106: 946-957 (2014).
6. Lee et al., "Coupling Photocatalysis and Redox Biocatalysis Toward Biocatalyzed Artificial Photosynthesis," *Chem. Eur. J.* 19: 4392-4406 (2013).
7 Steffen and Steuber, "Cation transport by the respiratory NADH: quinone oxidoreductase (complex I): facts and hypotheses," *Biochem. Soc. Trans.* 41: 1280-1287 (2013).
8. Verkhovskaya and Bloch, "Energy-converting respiratory Complex I: On the way to the molecular mechanism of the proton pump," *Int. J. Biochem. Cell. Biol.* 491-511 (2013).
9. Baradaran et al., "Crystal structure of the entire respiratory complex I." *Nature* 494(7438): 443-448 (2013).
10. Brandt, "Energy Converting NADH: Quinone Oxidoreductase (Complex I)," *Ann. Rev. Biochem.* 75 (1): 69-92 (2006).
11. Efremov et al., "The architecture of respiratory complex I," *Nature* 465(7297): 441-451 (2010).
12. Ohnishi et al., "A new hypothesis on the simultaneous direct and indirect proton pump mechanisms in NADH-quinone oxidoreductase (complex I)," *FEBS Lett.* 584 (19): 4131-4137 (2010).
13. Nore, "ΔpH driven energy-linked $NAD^+$ reduction in *Rhodospirillum rubrum* chromatophores," *Arch. Biochem. Biophys.* 274(1): 285-289 (1989).
14. Ohnishi et al., "Functional role of Coenzyme Q in the energy coupling of NADH-CoQ oxidoreductase (Complex I): Stabilization of the semiquinone state with the application of inside-positive membrane potential to proteoliposomes," *BioFactors* 32(1-4), 13-22 (2008).

15. Selivanov et al., "Reactive Oxygen Species Production by Forward and Reverse Electron Fluxes in the Mitochondrial Respiratory Chain," *PLoS Comput. Biol.* 7(3): e1001115 (2011).
16. Kotlyar and Borovok, "NADH oxidation and $NAD^+$ reduction catalysed by tightly coupled inside-out vesicles from *Paracoccus denitrificans*," *Eur. J. Biochem.* 269 (16): 4020-4024 (2002).
17. Wang et al., "Fast Isolation of Highly Active Photosystem II Core Complexes from Spinach," *J. Integr. Plant. Biol.* 52(9): 793-800 (2010).
18. Ramesh et al., "Isolation and characterization of an oxygen evolving photosystem 2 core complex from the thermophilic cyanobacterium *Mastigocladus laminosus*," *Photosynthetica*, 40(3): 355-361 (2002.
19. Kato et al., "Reisner, E., Protein film photoelectrochemistry of the water oxidation enzyme photosystem II," *Chem. Soc. Rev.* 43(18): 6485-6497 (2014).
20. Thornton et al., "The Low Molecular Weight Proteins of Photosystem II," in Wydrzynski and Satoh, Eds., Photosystem II The Light-Driven Water:Plastoquinone Oxidoreductase, Springer, 2006.
21. Barber, "Photosystem II: a multisubunit membrane protein that oxidises water," *Cur. Opin. Struct. Biol.* 12(4): 523-530 (2002).
22. Saito et al., "Mechanism of proton-coupled quinone reduction in Photosystem II," *Proc. Natl. Acad. Sci. USA* 110(3): 954-959 (2013).
23. Mavelli et al., "The binding of quinone to the photosynthetic reaction centers: kinetics and thermodynamics of reactions occurring at the Q(B)-site in zwitterionic and anionic liposomes," *Eur. Biophys. J. Biophy.* 43(6-7): 301-315 (2014).
24. Glockner et al., "Structural Changes of the Oxygen-evolving Complex in Photosystem II during the Catalytic Cycle," *J. Biol. Chem.* 288(31): 22607-22620 (2013).
25. Brudvig, "Water oxidation chemistry of photosystem II," *Philos. Trans. Royal Soc. B: Biol. Sci.* 363(1494): 1211-1219 (2008).
26. Liu and Wang, "Cofactor regeneration for sustainable enzymatic biosynthesis," *Biotechnol. Adv.* 25(4): 369-384 (2007).
27. Okuda et al., "Synthesis of Poly(Ethylene Glycol)-Bound NADP by Selective Modification at the 6-Amino Group of NADP," *Eur. J. Biochem.* 151,33-38 (1985).
28. Shen et al., "Biomimetic membranes: A review," *J. Memb. Sci.*, 454:359-381 (2014).
29. Rigaud and Levy, "Reconstitution of membrane proteins into liposomes," *Liposomes, Pt B*, 372: 65-86 (2003).
30. Liang et al., "Inherently tunable electrostatic assembly of membrane proteins," *Nano Let.* 8(1): 333-339 (2008).
31. Hua et al., "Self-Directed Reconstitution of Proteorhodopsin with Amphiphilic Block Copolymers Induces the Formation of Hierarchically Ordered Proteopolymer Membrane Arrays," *J. Am. Chem. Soc.* 133(8): 2354-2357 (2011).
32. Liang et al., "The directed cooperative assembly of proteorhodopsin into 2D and 3D polarized arrays," *Proc. Natl. Acad. Sci. USA* 104(20): 8212-8217 (2007).
33. Morina et al. "Engineering the Respiratory Complex I to Energy-converting NADPH:Ubiquinone Oxidoreductase," *J. Biolog. Chem.* 268 (40): 34627-34634 (2011).
34. Muh et al., Light-induced quinone reduction in photosystem II," *Biochimica Biophysica Acta Bioenerg.* 1817: 44-65 (2012).
35. Barber, "Photosystem II: a multisubunit membrane protein that oxidises water," *Cur. Opin. Struc. Biol.* 12: 523-530 (2002).
36. Brandt, "Energy Converting NADH: Quinone Oxidoreductase (Complex I)," *Ann. Rev. Biochem.* 75: 69-92 (2006).
37. Bezborodov and Zagustina, "Enzymatic Biocatalysis in Chemical Synthesis of Pharmaceuticals," *App. Biochem. Microbiol.* 52(3): 237-249 (2016).
38. Pohl et al., "Lambda Red-mediated mutagenesis and efficient large scale affinity purification of the *Escherichia coli* NADH:ubiquinone oxidoreductase (complex I)," *Biochemistry* 46, 10694-10702 (2007).
39. Bricker et al., "Isolation of a highly active Photosystem II preparation from Synechocystis 6803 using a histidine-tagged mutant of CP47," *Biochimica Biophysica Acta Bioenerg.* 1409: 50-57 (1998).
40. Vavilin, in Photosynthesis Research Protocols, Second Edition, R. Carpentier, Ed., Humana Press Inc, Totowa, 684: 29-40 (2011).
41. Rigaud and Levy, "Reconstitution of membrane proteins into liposomes," *Liposomes, Pt B* 372: 65-86 (2003).
42. Pryde and Hirst, "Superoxide is produced by the reduced flavin in mitochondrial complex I: a single, unified mechanism that applies during both forward and reverse electron transfer," *J. Biolog. Chem.* 286:18056-18065 (2011).
43. Kotlyar and Vinogradov, "Slow Active Inactive Transition of the Mitochondrial Nadh-Ubiquinone Reductase," *Biochimica Biophysica Acta Bioenerg.* 1019:151-158 (1990).
44. Hsu et al., "The two binding sites for DCMU in Photosystem II," *Biochem. Biophys. Res. Comm.* 141: 682-688 (1986).
45. Trebst, "Inhibitors in the functional dissection of the photosynthetic electron transport system," *Photosynth. Res.* 92: 217-224 (2007).
46. Vinogradov et al., "Catalytic properties of mitochondrial NADH-ubiquinone reductase (Complex I)," *Biochemistry* 64:136-152 (1999).
46. Armstrong and Hirst, "Reversibility and efficiency in electrocatalytic energy conversion and lessons from enzymes," *Proc. Nat. Acad. Sci. USA* 108(34): 14049-14054 (2011).
47. Seigneuret and Rigaud, "Analysis of Passive and Light-Driven Ion Movements in Large Bacteriorhodopsin Liposomes Reconstituted by Reverse-Phase Evaporation. 2. Influence of Passive Permeability and Back-Pressure Effects Upon Light-Induced Proton Uptake," *Biochemistry* 25(21): 6723-6730 (1986).
48. Hazard and Montemagno, "Improved purification for thermophilic $F_1 F_0$ ATP synthase using n-dodecyl beta-D-maltoside," *Arch, Biochem Biophys.* 407(1): 117-124 (2002).
49. Vinogradov and Grivennikova, "Oxidation of NADH and ROS production by respiratory complex I," *Biochimica Biophysica Acta Bioenerg.* 1857(7): 863-871 (2016).
50. Zu et al., "Reversible, Electrochemical Interconversion of NADH and $NAD^+$ by the Catalytic (Iλ) Subcomplex of Mitochondrial NADH:Ubiquinone Oxidoreductase (Complex I)," *J. Am. Chem. Soc.* 125(20): 6020-6021 (2003).
51. Friedrich et al., "2 Binding-Sites for Naturally-Occurring Inhibitors in Mitochondrial and Bacterial Nadh-Ubiquinone Oxidoreductase (Complex-I)," *Biochem Soc. Transact.* 22(1): 20 226-230 (1994).

52. Ohnishi et al., "Possible roles of two quinone molecules in direct and indirect proton pumps of bovine heart NADH-quinone oxidoreductase (complex I)," *Biochimica Biophysica Acta Bioenerg.* 1797(12): 1891-1893 (2010).
53. Belevich et al., "Activation of respiratory Complex I from *Escherichia coli* studied by fluorescent probes," *Heliyon* 3(1): e00224 (2017).
54. Casadio, "Measurements of Transmembrane pH Differences of Low Extents in Bacterial Chromatophores—a Study with the Fluorescent-Probe 9-Amino, 6-Chloro, 2-Methoxyacridine," *Eur. Biophys. J.* 19(4): 189-201 (1991).
55. D'Alessandro et al., "Quantitative evaluation of the intrinsic uncoupling modulated by ADP and Pi in the reconstituted ATP synthase of *Escherichia coli*," *Biochimica Biophysica Acta Bioenerg.* 1807(1): 130-143 (2011).
56. Loll et al., "Towards complete cofactor arrangement in the 3.0 Å resolution structure of photosystem II," *Nature* 438: 1040-1044 (2005).
57. Umena et al., "Crystal structure of oxygen-evolving photosystem II at a resolution of 1.9 Å," *Nature* 473: 55-60 (2011).
58. Su et al., "Structure and assembly mechanism of plant $C_2S_2M_2$-type PSII-LHCII supercomplex," *Science* 357 (6353): 815-820 (2017).
59. Sheng et al., "Structural insight into light harvesting for photosystem II in green algae," *Nature Plants* 5: 1320-1330 (2019).
60. Wei et al., "Structure of spinach photosystem II-LHCII supercomplex at 3.2 Å resolution," *Nature* 534: 69-74 (2016).
61. van Bezouwen et al., "Subunit and chlorophyll organization of the plant photosystem II supercomplex," *Nature Plants* 3: 17080 (2017).
62. Sazanov and Hinchliffe, "Structure of the hydrophilic domain of respiratory complex I from *Thermus thermophilus*," *Science* 311(5766): 1430-1466 (2006).
63. Steuber et al., "Structure of the *V. cholerae* Na+-pumping NADH:quinone oxidoreductase," *Nature* 516: 62-67 (2014).
64. Parey et al., "High-resolution cryo-EM structures of respiratory complex I: Mechanism, assembly, and disease," *Science Advances* 5(12): eaax9484 (2019).
65. Kampjut and Sazanov, "The coupling mechanism of mammalian respiratory complex I," *Science* 370 (6516): eabc4209 (2020).
66. Zhu et al., "Structure of mammalian respiratory complex I," *Nature* 536: 354-358 (2016).
67. Bridges et al., "Structure of inhibitor-bound mammalian complex I," *Nature Comm.* 11(5261) (2020).
68. Guo et al., "Architecture of Human Mitochondrial Respiratory Megacomplex $I_2III_2IV_2$," *Cell* 170(6): 1247-1257 (2017).

EXAMPLES

Example 1

Materials and Methods

Purification of NADH:Ubiquinone Oxidoreductase (Complex I)

Figure 2A:
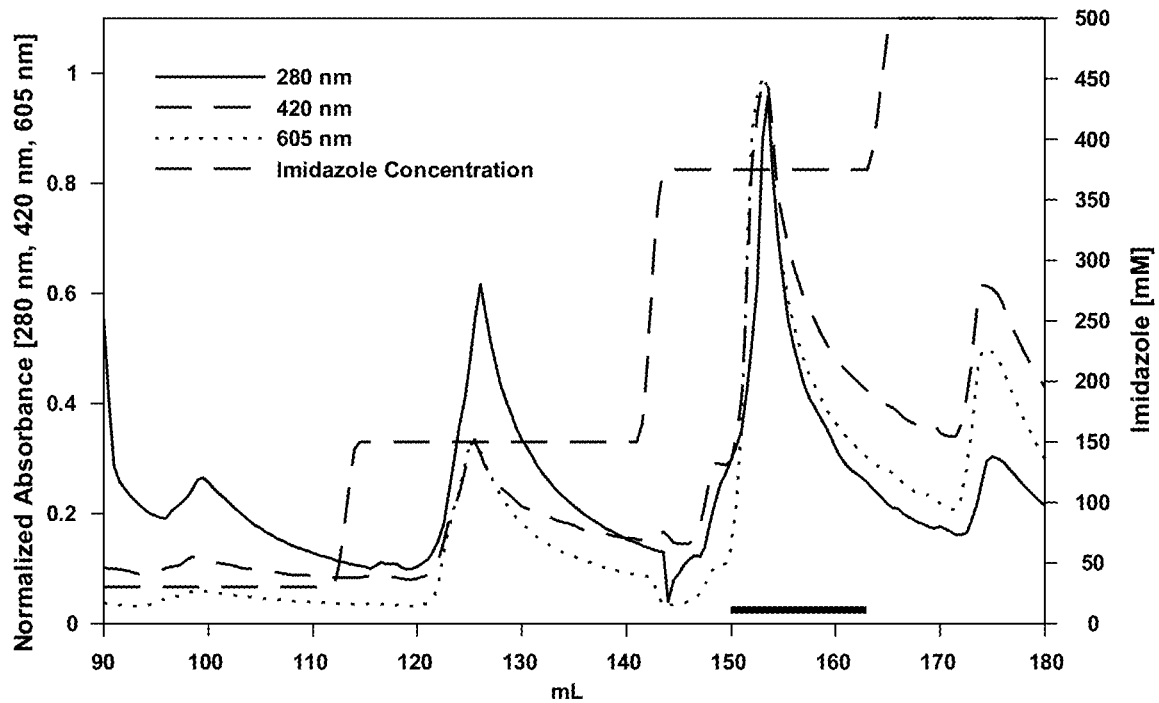
FIG. 2A-B show the purification of NADH:ubiquinone oxidoreductase (Complex 1) from *E. coli*.
Figure 2B:
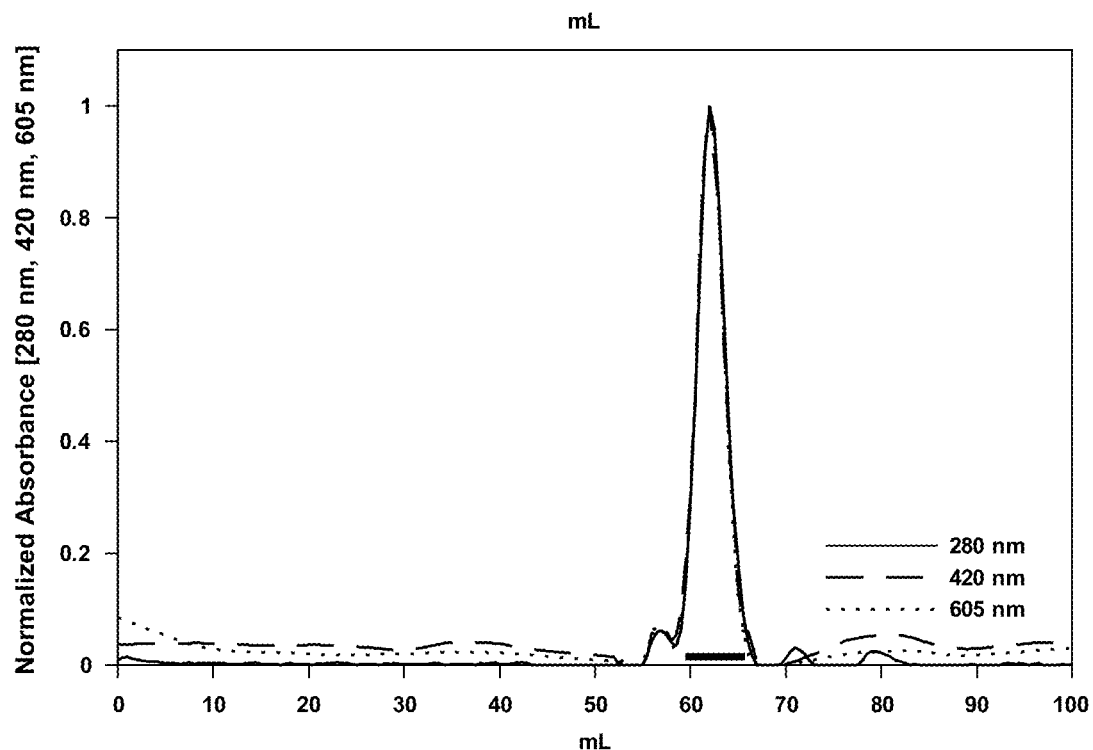
Figure 3:
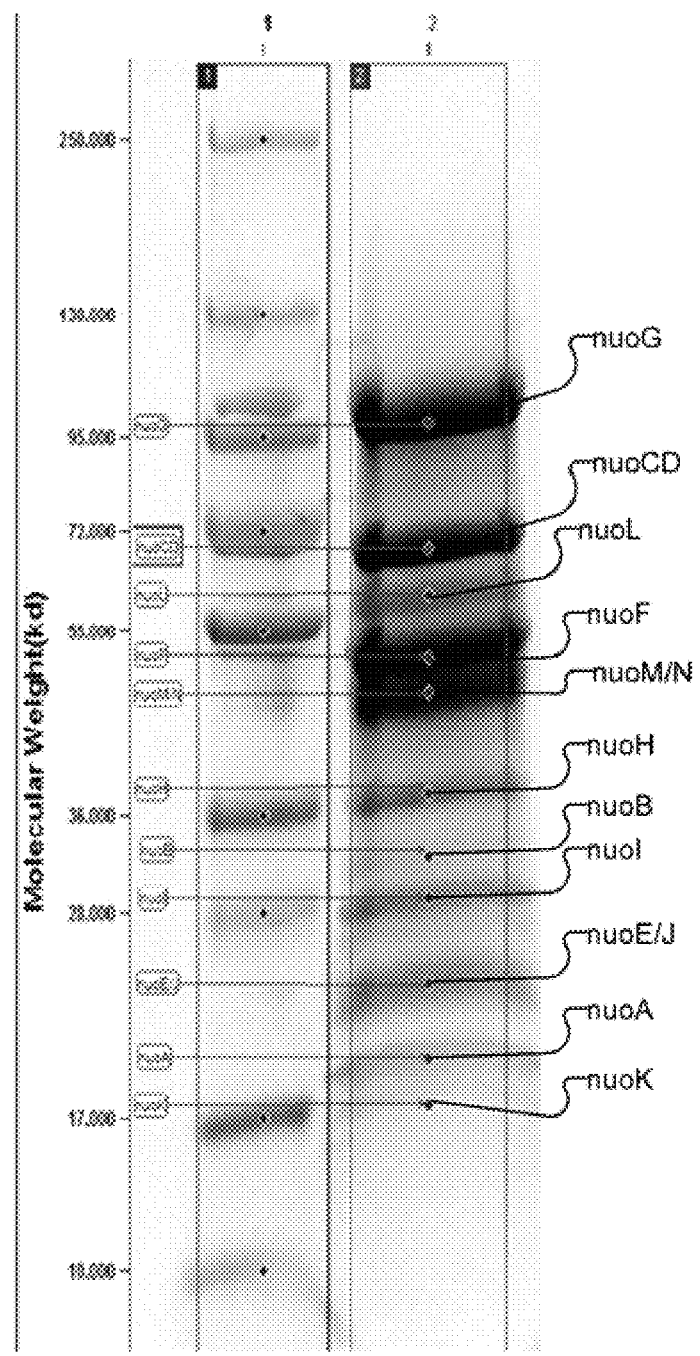
FIG. 3 shows a sodium dodecyl sulfate-polyacrylamide gel electrophoresis SDS-PAGE of purified Complex I from *E. coli*. Lane 1, molecular weight markers; Lane 2, 100 µg of purified Complex I. All 13 subunits of *E. coli* Complex I are present with no contaminating bands. Bands are labeled by the apparent molecular weight of the subunits.

Respiratory Complex I (CMI) was purified from *E. coli* overexpression strain ANN0221 using modifications to the methods described by Pohl et al. [38]. All chromatographic steps were performed using a GE ÄKTApure 25 or ÄKTAavant 125. The anion exchange step was omitted, and affinity chromatography was completed using a Tricorn 10 mm×100 mm (GE Healthcare Life Sciences, Inc.) column packed with High-Performance $Ni^{2+}$ resin (GE Healthcare Life Sciences, Inc.). The sample was adjusted to a final imidazole concentration of 50 mM and 200 mM NaCl, followed by sample loading at 153 cm $h^{-1}$; the column was washed with 150 mM imidazole and CMI was eluted with 375 mM imidazole step gradient at 76.5 cm $h^{-1}$ in up-flow operation (FIG. 2A). The fractions containing CMI (indicated by black bar) were concentrated using a 100 kD MWCO Amicon® Ultra centrifugal filter (EMD Millipore, Inc.) to 2-3 mL. The concentrated protein sample was polished and desalted into 50 mM MES, pH 6.0, 50 mM NaCl 0.1%(w/v) DDM by applying to a HiLoad 16/600 Superdex 200 (GE Healthcare Life Sciences, Inc.) size exclusion column (FIG. 2B). Fractions containing CMI (indicated by black bar) were concentrated to 4-5 mg $mL^{-1}$ using Amicon® Ultra centrifugal filters, aliquoted, snap frozen, and stored at −80° C. FIG. 3 shows SDS-PAGE of the purified CMI confirming that all 13 subunits of Complex I are present with no contaminating bands.

Purification of Photosystem II

Figure 4A:
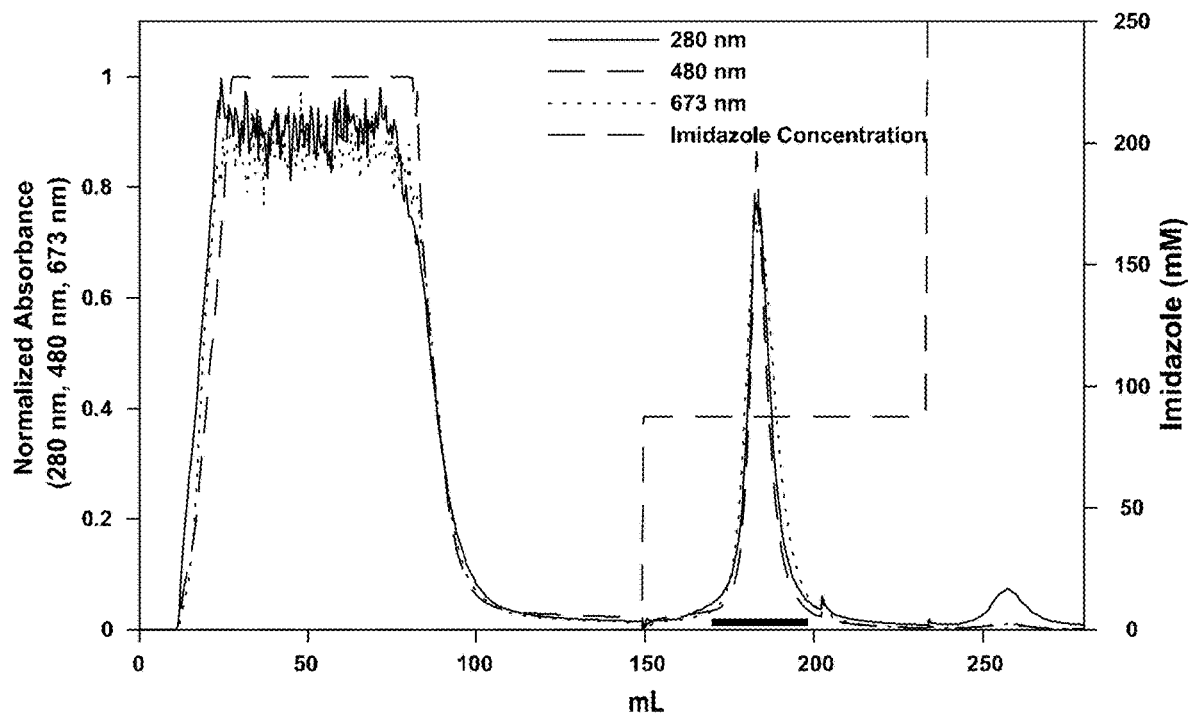
FIG. 4A-B show the purified Photosystem II (PSII) from Cyanobacterium *synechocystis* 6803 (*Synechocystis* sp. PCC 6803) used in the examples.
Figure 4B:
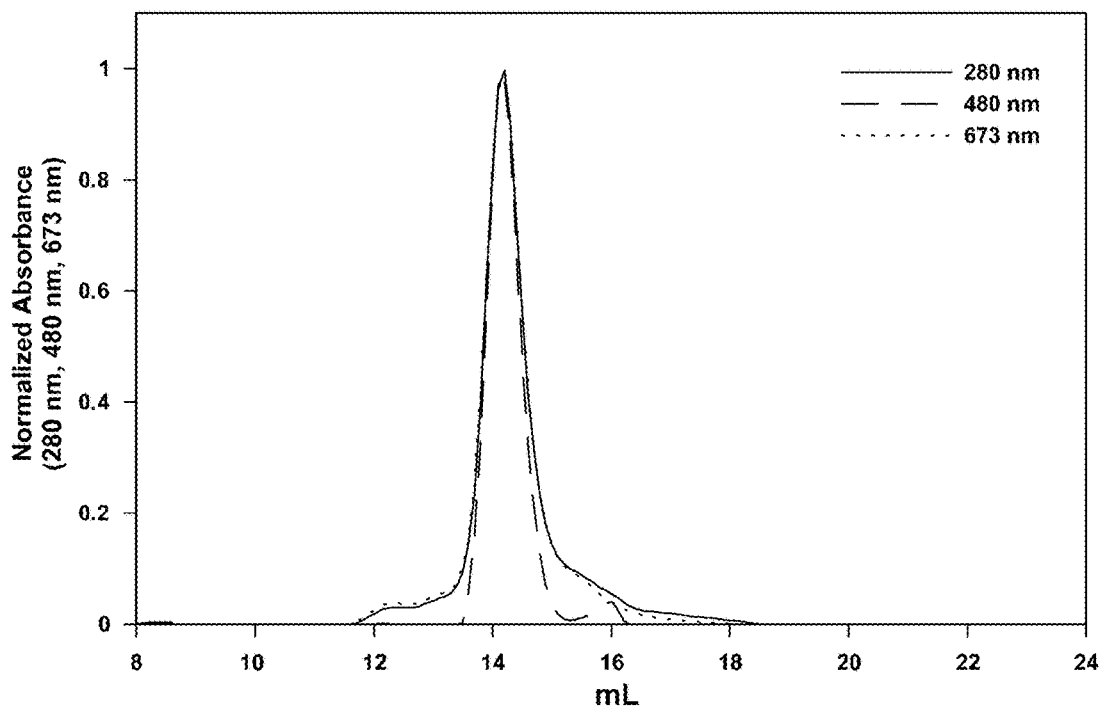

Photosystem II (PSII) with a histidine tag located on the CD47 subunit was isolated from *Cyanobacterium synechocystis* 6803 (*Synechocystis* sp. PCC6803) [39]. Isolated thylakoid membranes were resuspended to 1 mg ChlA $mL^{-1}$ in 50 mM MES, pH 6.0 10 mM $MgCl_2$, 5 mM $CaCl_2$, 25% (v/v) glycerol. The membranes were solubilized by dropwise addition of 20% (w/v) DDM to a final concentration of 0.8% (w/v) and incubated at 4° C. for 20 min. Non-solubilized material was removed by centrifugation using a multiple speed increase 100 rcf×1 min, 2,900 rcf×1 min, 4,900 rcf×1 min, 8,000 rcf×1 min, 15,100 rcf×1 min and 22,100 rcf×10 minutes using a Beckman Coulter Type 45-Ti Rotor. All chromatography steps were performed using an ÄKTAPure 25. The sample was loaded onto an XK 20/10 column (GE Healthcare Life Sciences, Inc.) packed with High-Performance $Ni^{2+}$ resin (GE Healthcare Life Sciences, Inc.) pre-equilibrated with binding buffer at a linear flow rate of 38 cm $h^{-1}$. Column washing was continued with binding buffer at 38 cm $h^{-1}$ until the absorbance at 280 nm fell below 90 mAU. PSII was eluted using 87.5 mM L-Histidine in up-flow operation at 22.6 38 cm $h^{-1}$ and 2 mL fractions were collected (FIG. 4A). Fractions containing PSII (shown by black bar) were pooled and concentrated using a 100 kD MWCO Amicon® Ultra centrifugal filter (EMD Millipore, Inc.). Removal of L-histidine was completed by diluting the concentrated sample 10-fold with binding buffer and concentrated; this was repeated 3 times. Samples were concentrated to 2-3 mg $mL^{-1}$ using Amicon® Ultra centrifugal filters, aliquoted, snap frozen and stored at −80° C. Chlorophyll A concentration was determined using 80% (v/v) acetone extraction [40]. Purity of the obtained PSII was verified by size exclusion chromatography on a Superose 6 Increase 10/300 column (FIG. 4B); black bars indicate fractions used in subsequent steps).

Unilamellar Liposome Preparation

Total *E. coli* lipid extract (Avanti Lipids Polar, Inc.) were dissolved in chloroform ($CHCl_3$) at 20 mg $mL^{-1}$ in a glass scintillation vial. A thin film was formed by removal of the $CHCl_3$ under vacuum at 0 mm Hg using a rotary evaporator.

The thin film was rehydrated to 15.34 mg mL$^{-1}$ using 5 mM MES, pH 6.5 50 mM KCl, 5 mM MgCl$_2$ 2 mM CaCl$_2$ buffer and placed in a sonication bath for 5 min followed by two freeze-thaw cycles before being extruded through a 0.4 μm polycarbonate membrane 21 times. The mean diameter was measured by dynamic light scattering; a typical preparation was 180 nm.

Enzyme Reconstitution

The unilamellar liposome suspension was diluted to a final lipid concentration of 4 mg mL$^{-1}$ and CHAPS concentration of 5 mM by the combination of appropriate amounts of the corresponding buffer, 200 mM CHAPS in the corresponding buffer and concentrated protein. The liposomes-detergent mixture was incubated for 10 min before the addition of protein. The appropriate amount of CMI (4.7 mg mL$^{-1}$, 50 mM MES, pH 6.0, 50 mM NaCl 1.95 mM n-dodecyl-β-D-maltoside (DDM)) and PSII (2.6 mg mL$^{-1}$, 50 mM MES, pH 6.0 10 mM MgCl$_2$, 5 mM CaCl$_2$, 25% (v/v) glycerol, 0.78 mM DDM) were added to the CHAPS-solubilized preformed liposomes and incubated for 30 min at 4° C. will gentle mixing in the dark. For control experiments which did not contain an enzyme, the difference in volume was adjusted with buffer.

After the incubation period, the detergent was removed from the lipid-detergent-protein mixture by 3 successive additions of Bio-Beads SM-2 (80 mg mL$^{-1}$) every 60 min followed by a final addition of 240 mg mL$^{-1}$ and 60 min incubation.

Complex I Activity Measurements

Complex I NADH:DQ oxidoreductase and proton pumping activity were measured simultaneously using a Flexstation 3 (Molecular Devices, Inc.). NADH:DQ oxidoreductase activity was monitored through NADH oxidation by fluorescence spectroscopy ($\lambda_{exictation}$=340 nm, $\lambda_{emission}$=455 nm), while proton gradient generation was determined by quenching of ACMA ($\lambda_{exictation}$=410 nm, $\lambda_{emission}$=480 nm). The assay was conducted at 28° C. in the corresponding buffer, 25 μL of proteoliposomes were added to 175 μL assay mixture containing 100 μM DQ, 200 μM NADH, 0.2 μM valinomycin, 2.5 μM ACMA and for decoupling and inhibition assays 5 μM CCCP (carbonyl cyanide 3-chlorophenylhydrazone) and 50 μM Piericidin A, respectively. The sample was incubated for 5 min prior to reaction initiation by addition of NADH. When conducting inhibition assays proteoliposomes were incubated for 5 min with Piericidin A before the addition of DQ.

For these experiments, decylubiquinone (DQ) was selected as the analogue of ubiquinone because it could be readily incorporated into the proteoliposomes and could be used by both PSII and CMI. One skilled in the art could use alternative analogues of ubiquinone or ubiquinol for use in any particular situation.

Photosystem II Activity Measurements

Oxygen evolution assays were performed using 50 mM MES, pH 6.5, 10 mM NaCl, 5 mM MgCl$_2$, 20 mM CaCl$_2$ using a Clarke-type electrode (Hansatech Instruments, Ltd.). 2 mM ferricyanide and either 300 μM 2,5-dicholor-1,4-benzoquinone (DCBQ) or 50 μM DQ was added as electron acceptor with 5×10$^{-10}$ μg of ChlA of the sample to a final volume of 1.5 mL. The reaction took place at 28° C. and was initiated by red light at 2800 μmol s$^{-1}$ m$^{-2}$.

ATAD$^+$ Photoreduction Assay

Photoreduction by CMI:PSII proteoliposomes were routinely performed at 28° C. in 5 mM MES, pH 6.5, 50 mM KCl, 5 mM MgCl$_2$ 2 mM CaCl$_2$, 25 μL of proteoliposomes were added to 175 μL assay mixture containing 50 μM DQ, 0.2 μM valinomycin, 2.5 μM ACMA; and for decoupling and inhibition assays: 5 μM CCCP and 100 μM DCMU, respectively. The potassium ionophore, valinomycin, was added to collapse the electrical component of the PMF and generate a higher ΔpH. Without being bound by any theory, the reverse electron transfer activity of CMI is believed to be more dependent on the proton component of the pH gradient than the electrical component of the pH gradient. Saturating white light >2200 μmol photons m$^{-2}$ s$^{-1}$ was provided by a 100 W Mercury lamp. The light was passed through a 2 L water bath. The reaction was monitored using Flexstation 3 (Molecular Devices, Inc.), NADH concentration was monitored by fluorescence spectroscopy ($\lambda_{exictation}$=340 nm, $\lambda_{emission}$=455 nm), while the proton gradient generation was determined by the change in ACMA signal ($\lambda_{exictation}$=410 nm, $\lambda_{emission}$=480 nm).

Protein Concentration

Protein concentration was routinely determined using Millipore Direct Detect® infrared spectrometer (EMD Millipore, Inc.).

Example 2

Production of Exemplary Proteoliposome Constructs

The isolated enzymes were reconstituted into liposomes following the methods delineated by Riguard [41]. When reconstituting membrane proteins, preservation of structure and activity, and also vectoral insertion of the membrane protein into the membrane in the correct orientation are important. Control of the concentrations of buffer and salt, and control of pH, can be used to preferentially drive reconstitution of the membrane protein with the desired orientation in the membrane.

Successful co-reconstitution of both enzymes into a single liposome initially required detergent screening experiments to reconstitute each enzyme independently (results shown in Tables 4 and 5). The optimal detergent and concentration were selected based upon their impact both on the PMF generation and enzymatic activity for each reconstituted enzyme/detergent pair.

The zwitterionic surfactant CHAPS (3-[(3-cholamidopropyl)dimethylammonio]-1-propanesulfonate) was found most suitable for co-reconstitution under the conditions tested. Other tested detergents were DDM (n-dodecyl-β-D-maltopyranoside), Triton X100™ (polyethylene glycol p-(1,1,3,3-tetramethylbutyl)-phenyl ether), and OG (n-octyl-β-D-glucoside).

TABLE 4

Detergent Screening for CMI.

| Detergent | Detergent Concentration (mM) | ACMA Fluorescence decrease | NADH:DQ oxidoreductase activity (umol min$^{-1}$ mg CMI$^{-1}$) |
|---|---|---|---|
| DDM | 3.8 | 1.46% | 13.43 |
| DDM | 7 | 0.32% | 0.76 |
| Triton X-100 ™ | 1.8 | −2.75% | −0.00 |
| Triton X-100 ™ | 7 | −4.90% | 9.05 |
| OG | 18 | 0.71% | 5.24 |
| OG | 26 | −0.16% | 8.95 |
| CHAPS | 3.0 | 0.58% | N/A[1] |
| CHAPS | 7 | 74.54% | N/A[1] |

[1]Rates were too fast to measure, and were confirmed by the inhibition with 50 μM Piericidin A.
Rates for inhibited samples CHAPS 3.0 and 7.0 mM proteoliposomes were −1.05 and −0.48 (umol min$^{-1}$ mg CMI$^{-1}$), respectively.

TABLE 5

Detergent Screening for PSII.

| Detergent | Detergent Concentration (mM) | O$_2$ Evolution (umol O$_2$ hr$^{-1}$ ug ChlA) (mean ± S.D.) |
|---|---|---|
| CHAPS | 3.0 | 178.08 ± 9.91 |
| CHAPS | 7 | 509.24 ± 256.84 |
| DDM | 3.8 | 565.87 ± 25.19 |
| DDM | 6.8 | 396.55 ± 69.76 |
| OG | 18 | 306.95 ± 44.24 |
| OG | 26 | 481.01 ± 192.16 |
| TRITON X-100 ™ | 1.8 | 530.72 ± 2.53 |
| TRITON X-100 ™ | 7 | 218.69 ± 67.01 |

Figure 5A:
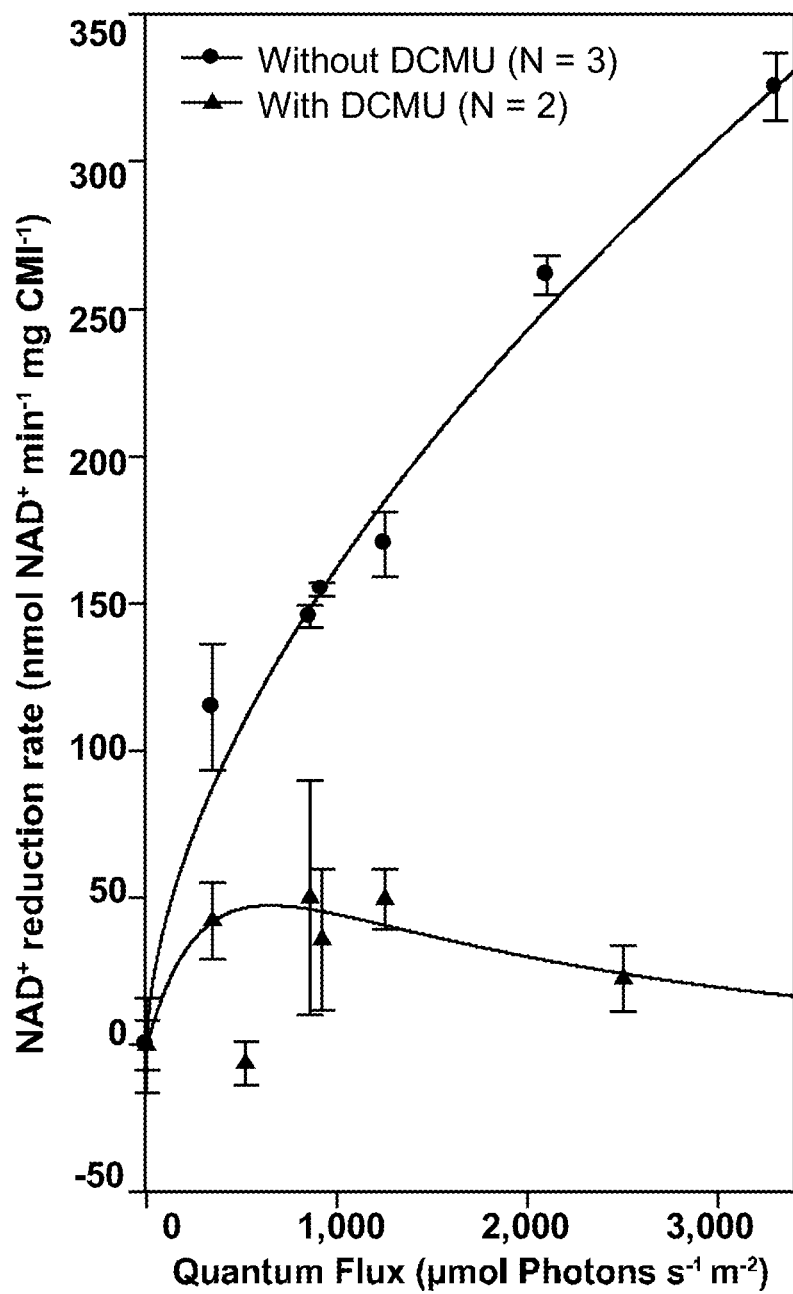
FIG. 5A-C show activity versus quantum flux and Coupling efficiency of PSII and Complex I.

To confirm that CMI was reconstituted into the liposomes both NADH:decylubiquinone (DQ) oxidoreductase activity and proton translocation were measured by monitoring NADH oxidation with the corresponding quenching of the pH sensitive fluorophore 9-amino-6-chloro-2-methoxyacridine (ACMA), respectively. The results are shown in FIG. 5. In FIG. 5A, after 5 min of incubation at 28° C., 200 μM NADH was added, and the depletion of NADH (dashed lines) and ACMA signal (solid lines) was monitored. The ACMA signal begins to increase at ~5 min due to the complete oxidation of NADH by CMI.

Figure 5B:
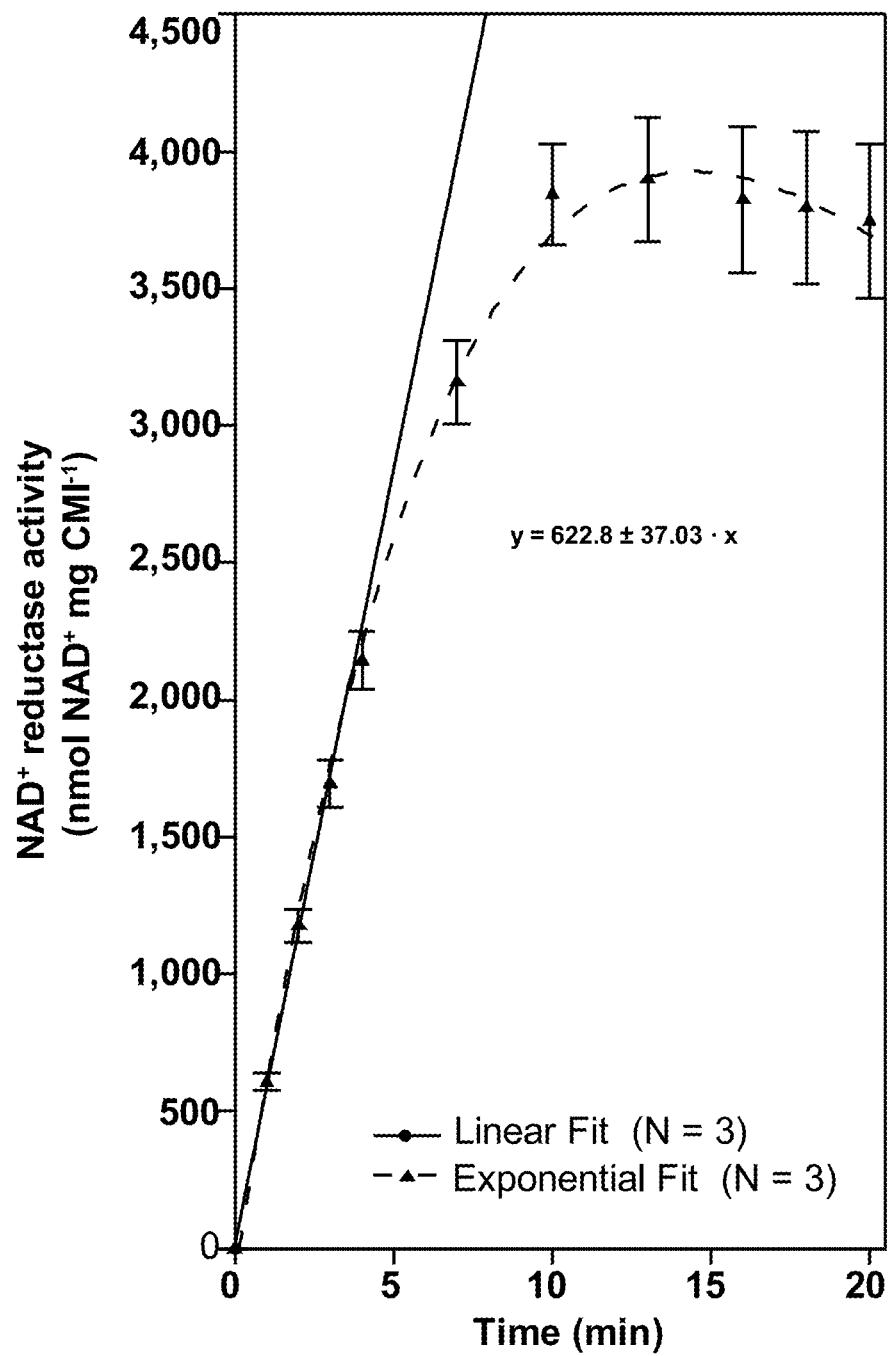
Figure 5C:
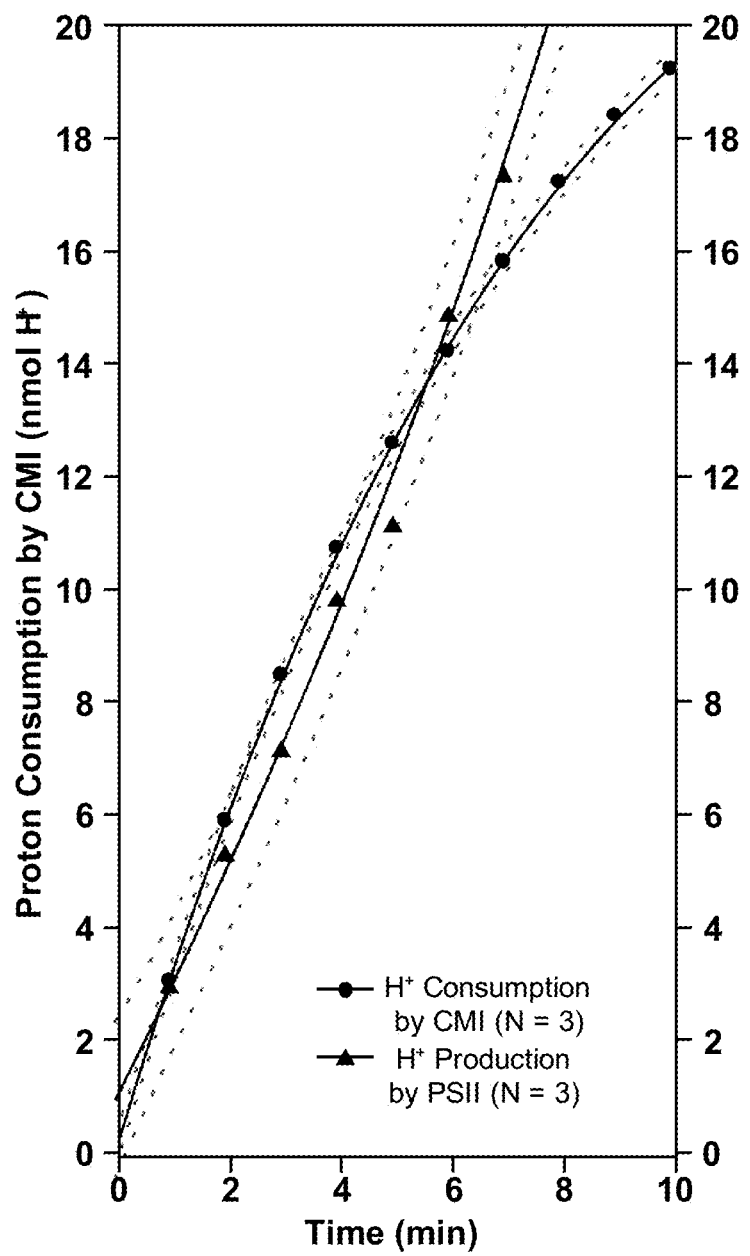

In FIG. 5B, the effect on PMF formation by CMI proteoliposomes of NADH alone (dot-dashed line, labelled ACMA), NADH plus Piericidin A (dashed line) and NADH plus CCCP (solid line) are shown. Samples were incubated for 5 min with addition reagents (CCCP or Piericidin A as indicated) before the addition of 200 μM NADH at the indicated point. At 8 min 5 μM CCCP was added to all samples and the proton gradient was abolished. The data in FIG. 5 represent the mean of three independent measurements of a single preparation.

CMI proteoliposome preparations result in an ~80% decrease in ACMA fluorescence with a NADH:DQ oxidoreductase specific activity of 3,200 nmol NADH min$^{-1}$ mg CMI$^{-1}$ (FIG. 5A), solid line labelled ACMA). The decrease in ACMA signal was confirmed to be the result of CMI activity from incubation with the protonophore carbonyl cyanide 3-chlorophenylhydrazone (CCCP) (which quenches the proton gradient), because minimal change in ACMA fluorescence was observed (FIG. 5A), solid line labelled ACMA 5 μM CCCP). Additionally, the NADH:DQ oxidoreductase specific activity of CMI proteoliposomes was inhibited >95% when incubated with 50 μM Piericidin A (FIG. 5A), compare dashed line labelled NADH 50 μM Piericidin A with dashed line labeled NADH; a potent CMI inhibitor [38].

Figure 6:
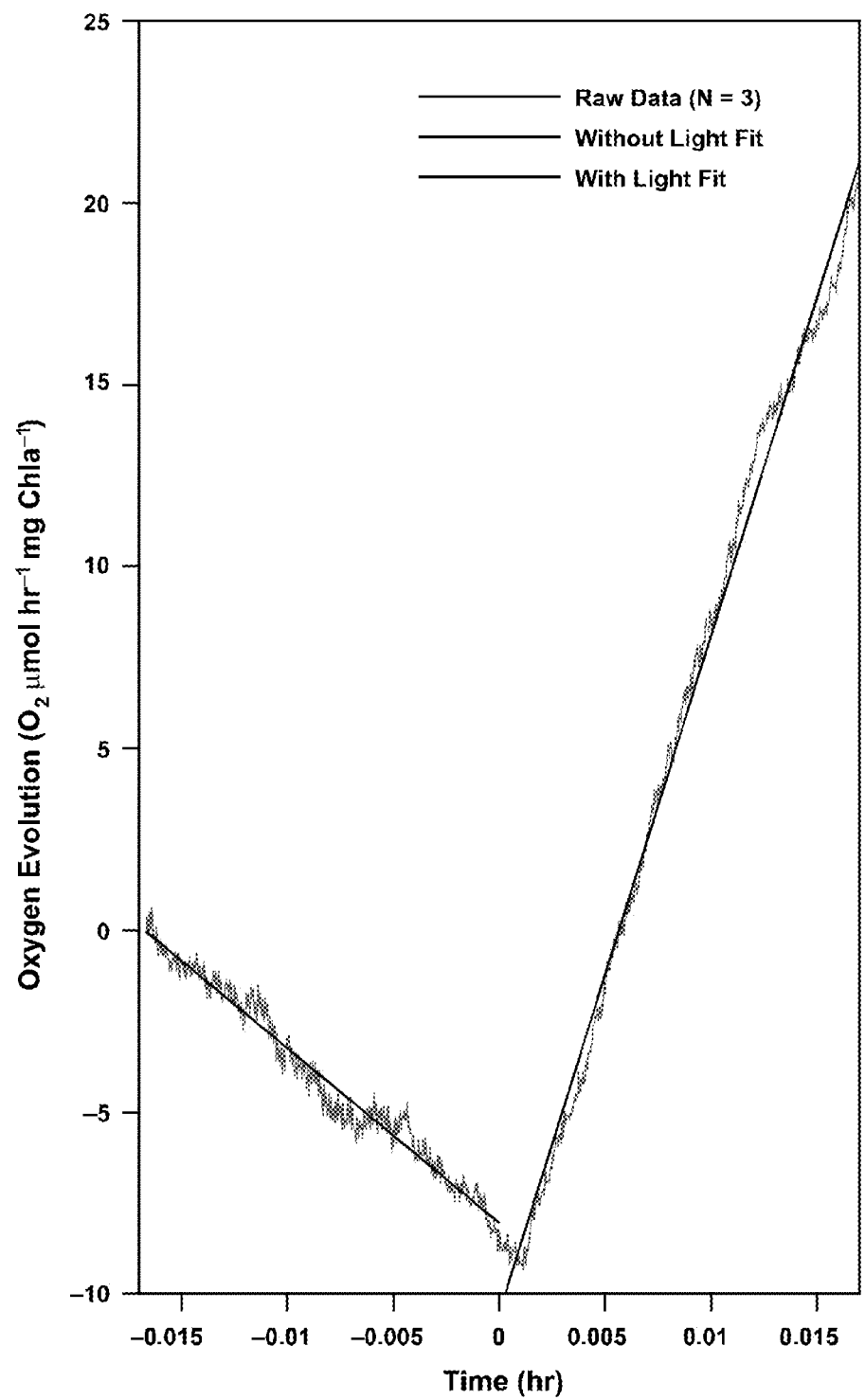
FIG. 6 shows oxygen evolution activity of purified Photosystem II. Results of one technical measurements of N PSII preparations. At time=0, Photosystem II was activated by the addition of saturated red light. The solid lines are $1^{st}$ degree polynomial fits of the dark (y=−(481±6.6)·x −(8.051±0.064)) and light (y=−(1863±11)·x−(10.53±0.11)) portions of the experiment. The dark correct oxygen evolution rate is 2343.9±24.75 µmol $O_2$ $hr^{-1}$ mg $Chla^{-1}$.

The reconstitution procedure for PSII was identical to that of the CMI proteoliposomes. The lipid to PSII ratio was fixed at 30:1 (w/w) to simplify the interpretation of the effect on the PSII to CMI ratio. FIG. 6 shows oxygen evolution by reconstituted PSII for one example tested. Results are shown from three independent measurements of a single PSII preparation. Saturated red light was added at 0 sec. The maximum rate of oxygen evolution was calculated as 1996.0±156.2 μmol O$_2$ hr$^{-1}$ mg Chlorophyll-a$^{-1}$.

For reconstituted proteoliposomes incorporating both PSII and CMI, oxygen evolution in addition to proton production of the resulting proteoliposomes were measured using a Clarke-type electrode and ACMA, respectively. Typical preparations resulted in a 35% decrease in ACMA signal with oxygen evolution rates of 509.24±256.84 μmol O$_2$ hr$^{-1}$ mg Chlorophyll-a$^{-1}$ (ChlA) with saturated light.

Example 3

Varying Ratios of CMI and PSII

Proteoliposomes containing CMI and PSII were prepared using the same method for the reconstitution of the individual proteins using 5 mM CHAPS. A suite of experiments varying CMI to PSII ratio were conducted including two PSII:CMI ratios; approximately 2 and 4 PSII molecules per molecule of CMI. The rationale for including more PSII then CMI was to allow PSII to rapidly generate and maintain the PMF necessary for the NAD$^+$:DQH$_2$ oxidoreductase activity of CMI.

Figure 7:
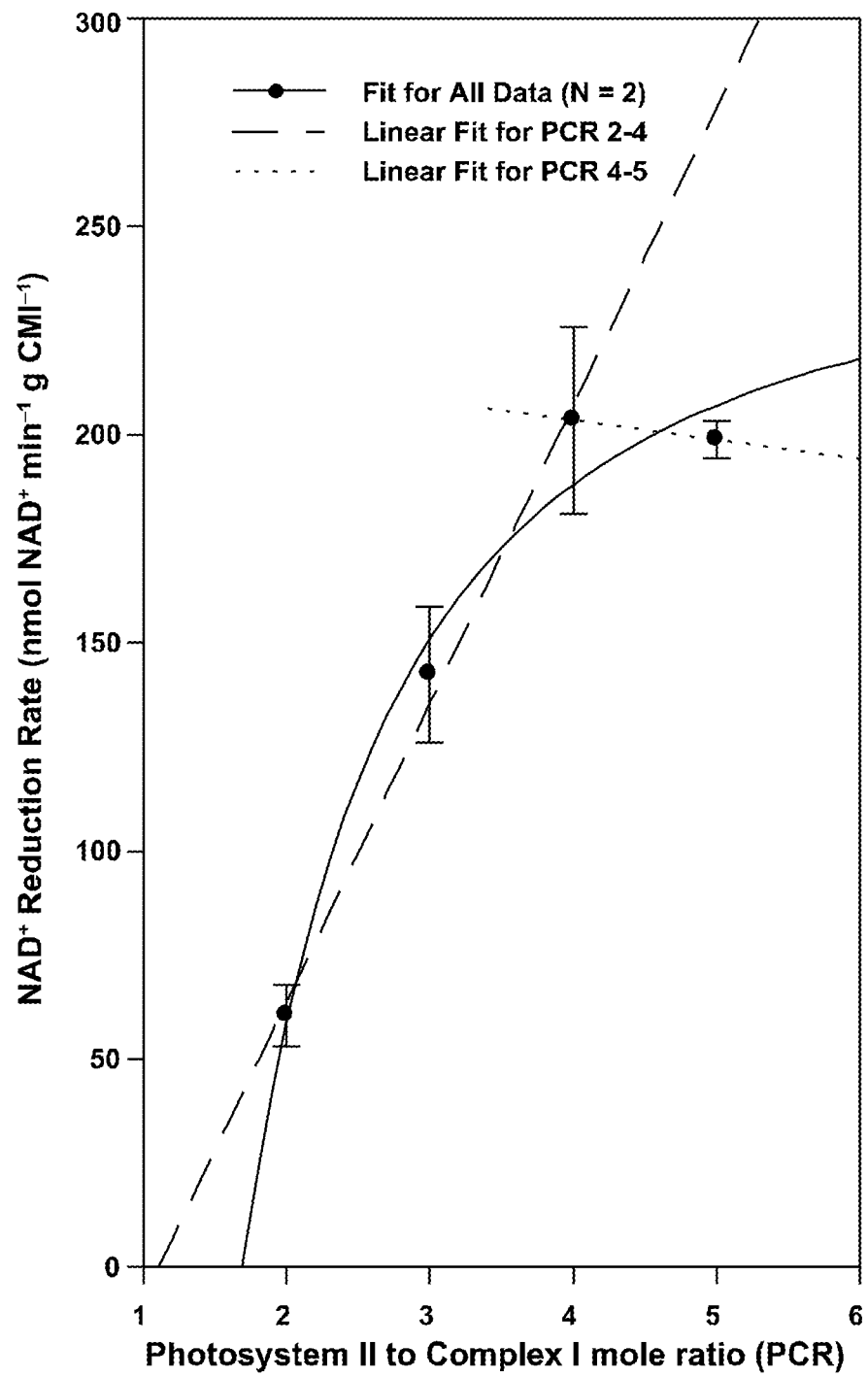
FIG. 7 shows the relationship between PCR and NADH production rate and total NADH produced. The rate of $NAD^+$ reduction versus Photosystem II to Complex I mole ratio (PCR). The error bars represent the standard deviation of n technical repeats of single biological replicate.

Results are shown in FIG. 7. FIG. 7A shows results at 1 mM NAD$^+$, and FIG. 7B shows results with 200 micromolar NADH. FIG. 7C and FIG. 7D show the images inset in FIG. 7A and FIG. 7B, respectively, and include results for empty liposome controls. Data are presented as the mean and standard deviation of three independent measurements of a single preparation.

The first series of NAD$^+$ photoreduction experiments were performed using 1 mM NAD$^+$ as the substrate (FIG. 7A). These initial experiments indicated that the rate of NAD$^+$ photoreduction of the samples containing higher PSII to CMI ratios (4PSII:1CMI) to be 28.6 nmol min$^{-1}$ mg CMI$^{-1}$ which is nearly twice that of rates from samples containing lower PSII to CMI (2PSII:1CMI), 15.1 nmol min$^{-1}$ mg CMI$^{-1}$.

Figure 8A:
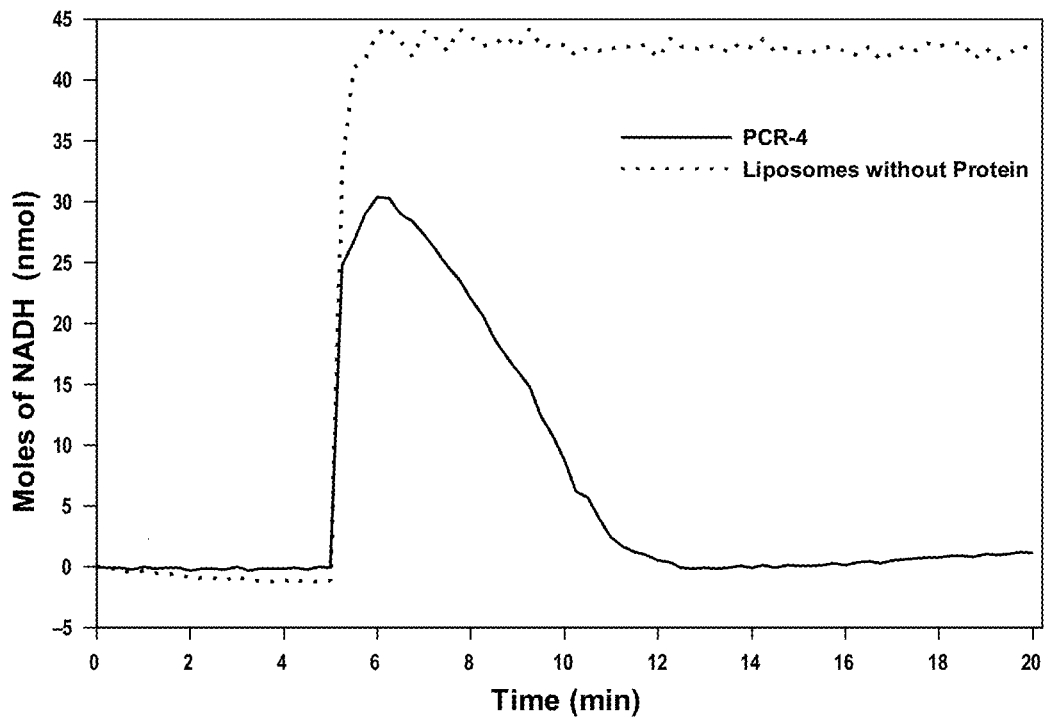
FIG. 8A-B show pre-initiation of $NAD^+$ photoreduction. Typical results from experiments which used 200 µM NADH as substrate before initiating photoreduction. Samples were incubated for 5 minutes prior to addition of 200 µM NADH (added at 5 min) and incubated for an additional 10-15 minutes to allow the ACMA signal to stabilize before starting photoreduction experiments.
Figure 8B:
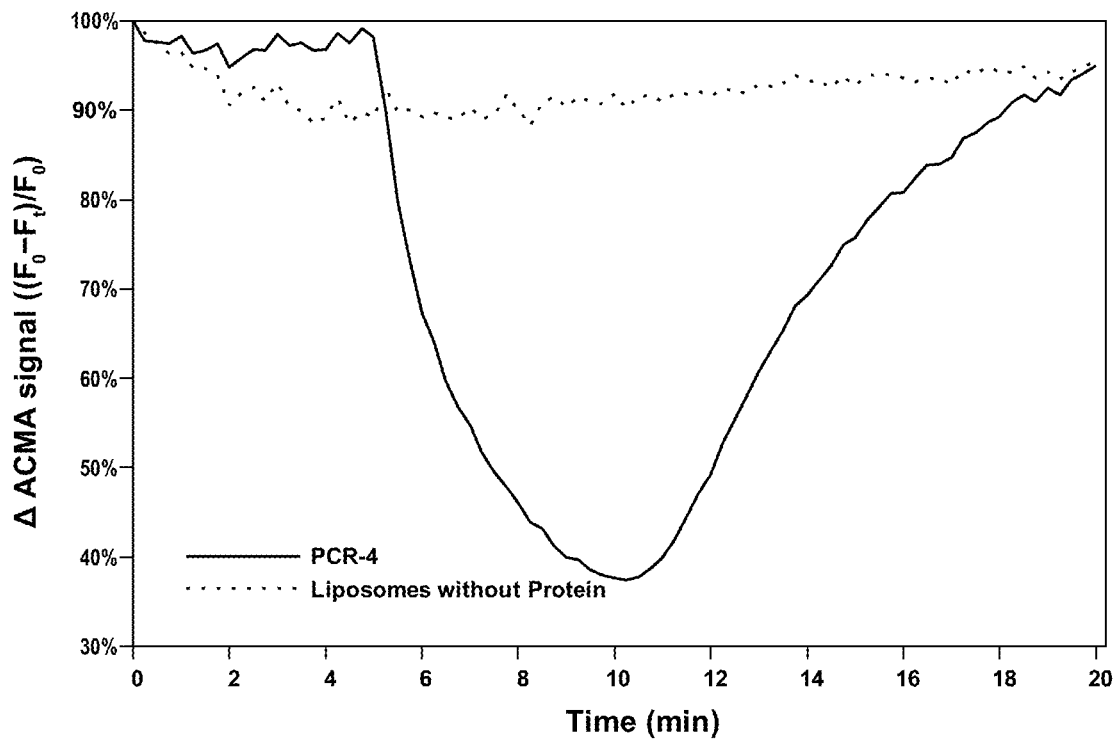

Previous studies on the succinate-supported NAD$^+$ oxidoreduction with submitochondrial particles (SMPs) revealed the addition of NADH activated CMI and rates of RET activity increased [42-43]. Without being bound by theory, results from this example are consistent with these earlier works when NAD$^+$ photoreduction assays are conducted by the addition of 200 μM NADH and initiating photoreduction after CMI no longer is oxidizing the substrate (results shown in FIG. 7B), pre-initiation of NAD$^+$ photoreduction using 200 μM NADH as the substrate is shown in FIG. 8A (NADH concentration) and FIG. 8B (ACMA signal). The resulting NAD$^+$ photoreduction rates were 323 and 89 nmol min$^{-1}$ mg CMI$^{-1}$ for 4PSII:1CMI and 2PSII:1CMI, respectively. In comparison to the experiments using 1 mM NAD$^+$ as the substrate, the rates were nearly an order of magnitude greater. Additionally, the NAD$^+$ photoreduction rate for the 4PSII:1CMI samples approached 4 times of the 2PSII:1CMI samples.

Results from experiments performed to determine the influence of PSII to CMI ratios on $NAD^+$ photoreduction concluded that proteoliposomes 4PSII:1CMI outperformed 2PSII:1CMI. This indicates that more PSII is necessary to maintain the activity of CMI, most likely to maintain the PMF. 4PSII:1CMI preparations, using 200 µM NADH as the substrate were selected for further characterization in subsequent experiments.

Example 4

Inhibition of PSII by DCMU

Figure 9A:
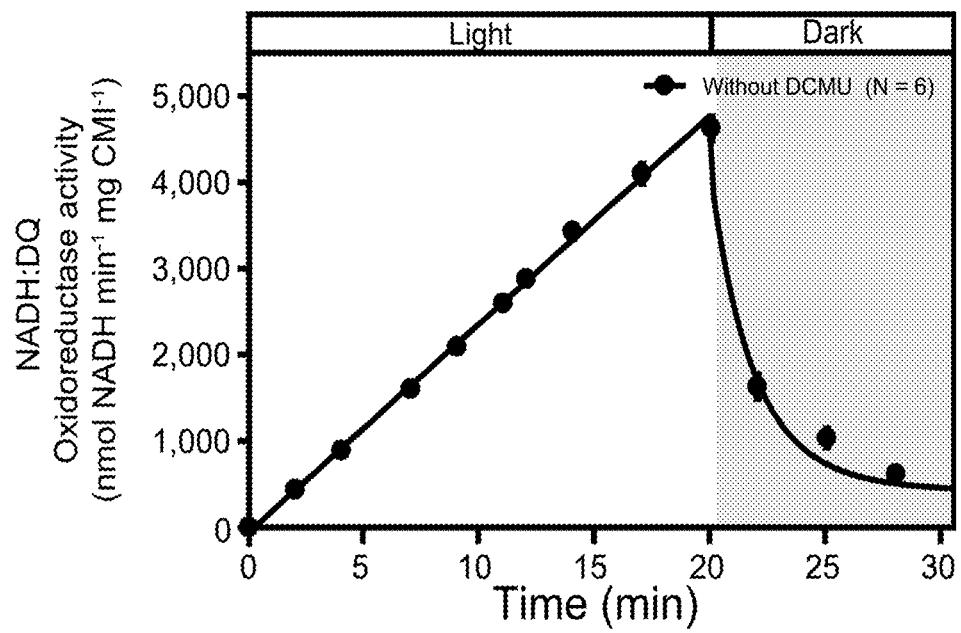
FIG. 9A-D show the relationship between $NAD^+$ photoreduction activity and ACMA signal of PCR-4 proteoliposomes.

To determine the consistency of the methods for preparing the 4PSII:1CMI proteoliposomes, three separate preparations were used. The preparations yielded consistent results, with an average maximum $NAD^+$ photoreduction rate of 354.85±38.71 nmol $min^{-1}$ mg $CMI^{-1}$ (FIG. 9A). Comparing the production rates of $H^+$ to NADH, it is possible to calculate the coupling efficiency of the two enzymes using the reaction stoichiometry of 5 $H^+$ to produce one NADH molecule. During the reaction PSII produces $H^+$ at 4.36±0.79 nmol $min^{-1}$ [calculated from the oxygen evolution activity of 4PSII:1CMI proteoliposomes 377.37±67.97 mol $O_2$ $hr^{-1}$ mg Chlorophyll-$a^{-1}$], whereas CMI is responsible for their consumption at −1.77±0.19 nmol $min^{-1}$ yielding a coupling efficiency of 38.32%±10.80%. Without being bound by theory, the remainder of unused $H^+$ could be accounted for by the protons required to generate the PMF together with protons produced by PSII molecules reconstituted in the incorrect orientation and proton leakage across the vesicle membrane.

When $NAD^+$ photoreduction is initiated both ACMA signal and NADH concentration increase in a similar fashion, suggesting that CMI is pumping protons out of the proteoliposomes as it is reducing $NAD^+$. After photoreduction, confirmation that NADH was being produced was obtained by letting the sample remain in the dark while continuing to monitor ACMA and NADH concentration. Once placed in the dark the NADH accumulated was oxidized. Additionally, as NADH concentration decreased the ACMA signal also decreased, indicating that CMI is pumping protons into the interior of the proteoliposomes. Both observations affirm NADH is being produced through coupling of PSII and CMI activity.

Figure 9B:
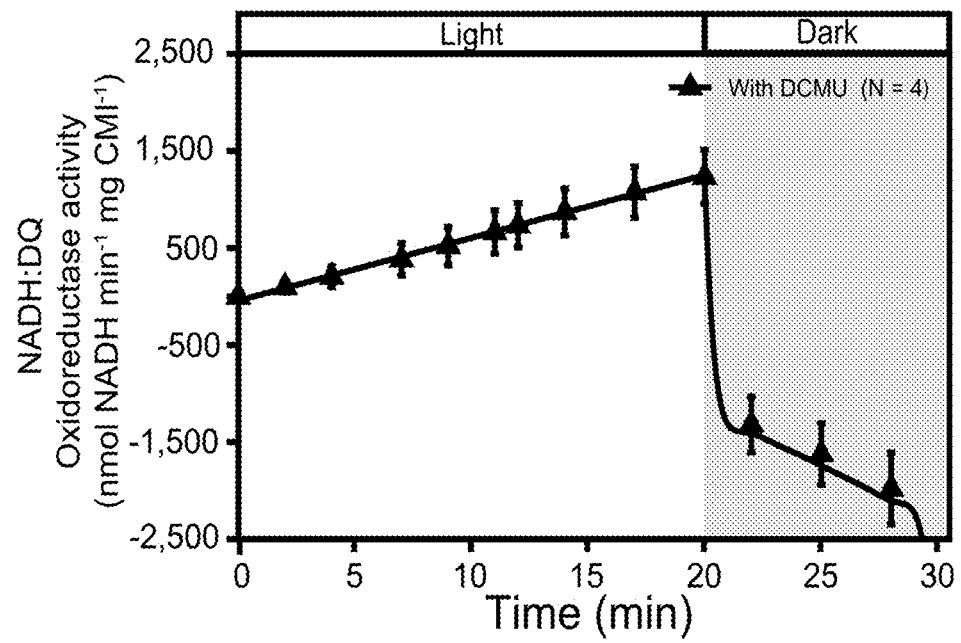
Figure 9C:
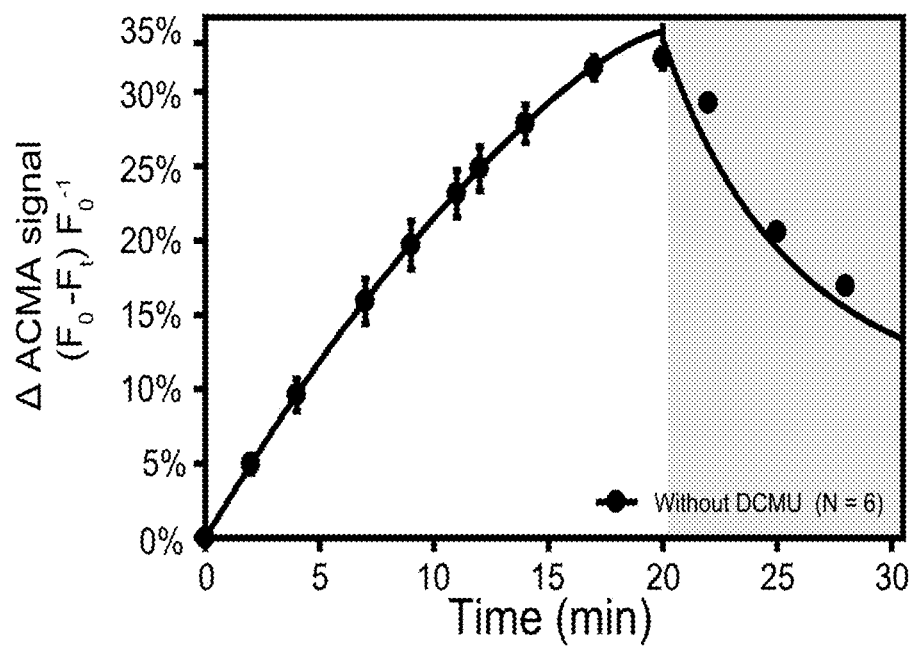
Figure 9D:
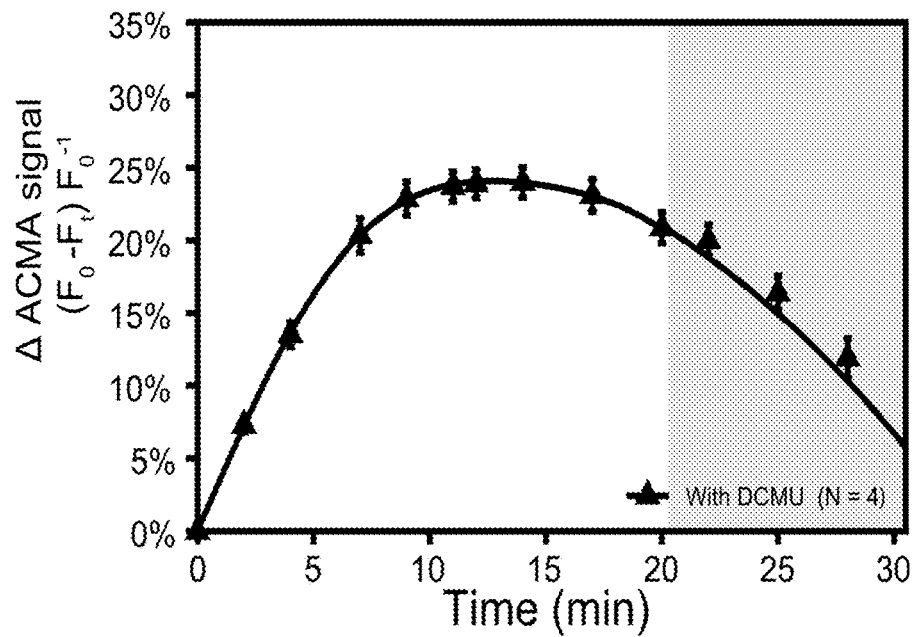

To reinforce the conclusion that PSII is providing electrons through decylubiquinol ($DQH_2$) and the PMF required for CMI to reduce $NAD^+$, PSII inhibition experiments were conducted (FIG. 9B). Prior to the initiation of photoreduction, proteoliposomes were incubated for 5 minutes with 100 µM 3-(3,4-dicholorophenyl)-1,1-dimethylurea (DCMU) an inhibitor of PSII [44-45]. While under illumination the inhibited sample shows a maximum rate of NADH production of 6.44±24.97 nmol $min^{-1}$ mg $CMI^{-1}$ compared to 222.29±12.57 nmol $min^{-1}$ mg $CMI^{-1}$ for the non-inhibited sample. After the removal of light, the average rate of NADH production are −170.65±2.26 and −198.19±13.67 nmol $min^{-1}$ mg $CMI^{-1}$ for the inhibited and non-inhibited samples, respectively. Comparing the results between the samples during and post illumination, PSII is indisputably providing both the electrons and PMF required to drive $NAD^+$ reduction by CMI.

Figure 10:
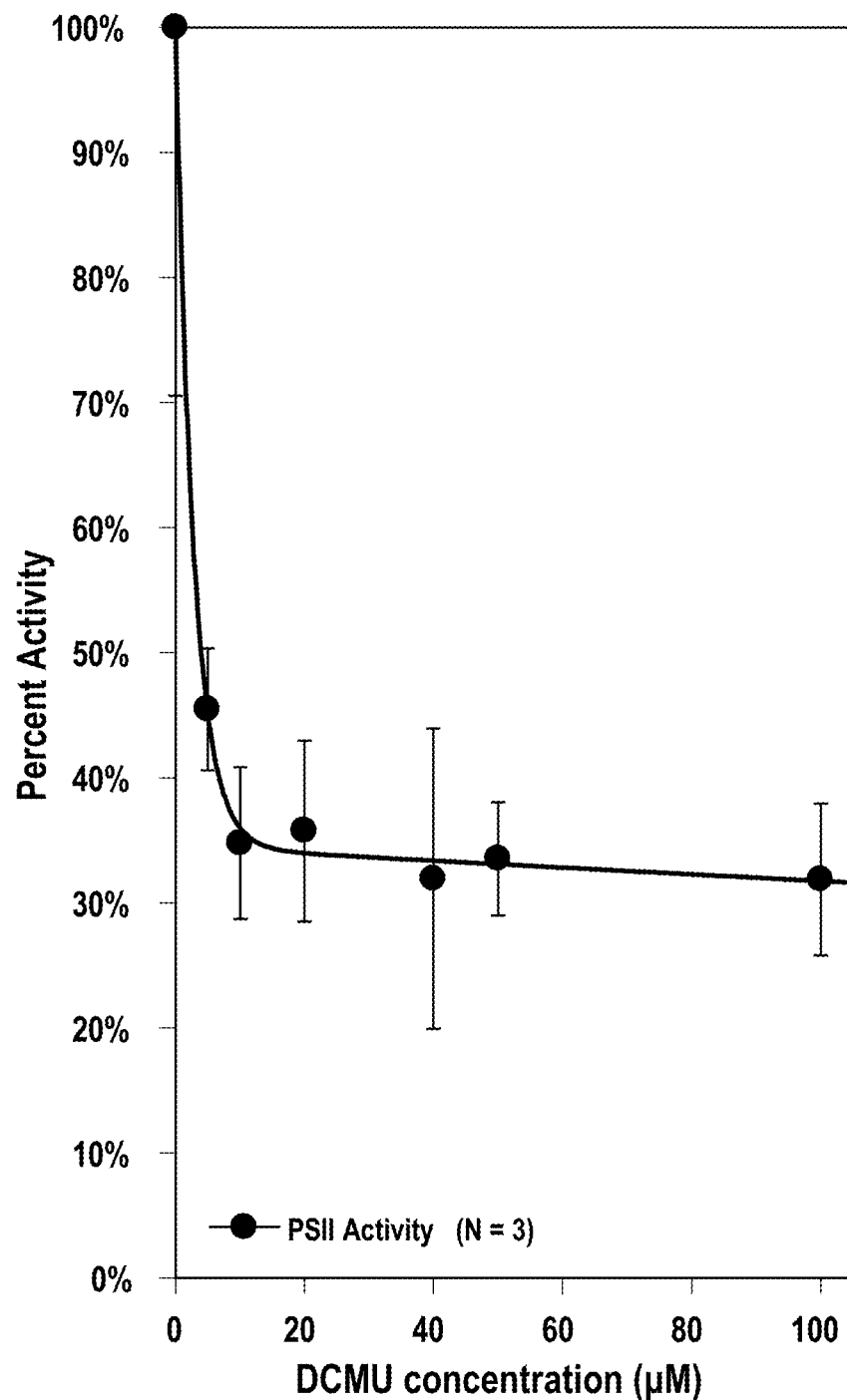
FIG. 10 shows the oxygen evolution activity vs. DCMU concentration for PCR-4 proteoliposomes. The error bars represent N biological replicates with one technical replicate.

Nonetheless, the similarity between the rates post illumination suggest that PSII is not completely inhibited, as experiments showed that isolated PSII was only 70% inhibited by 100 µM DCMU (FIG. 10). Without being bound by theory, the ACMA data is consistent with the interpretation that PSII is not fully inhibited, explaining the signal increase for the inhibited sample. However, the signal increase is only approximately 60% of that seen from the non-inhibited sample. Subtracting the post illumination from the illumination $NAD^+$ production rates, the rate of NADH production of the inhibited sample is 39.05%±7.64% of the non-inhibited sample, which is in good agreement with the interpretation that PSII is inhibited by 70%.

Example 5

Evaluation of Multiple Light Dark Cycles

Figure 11A:
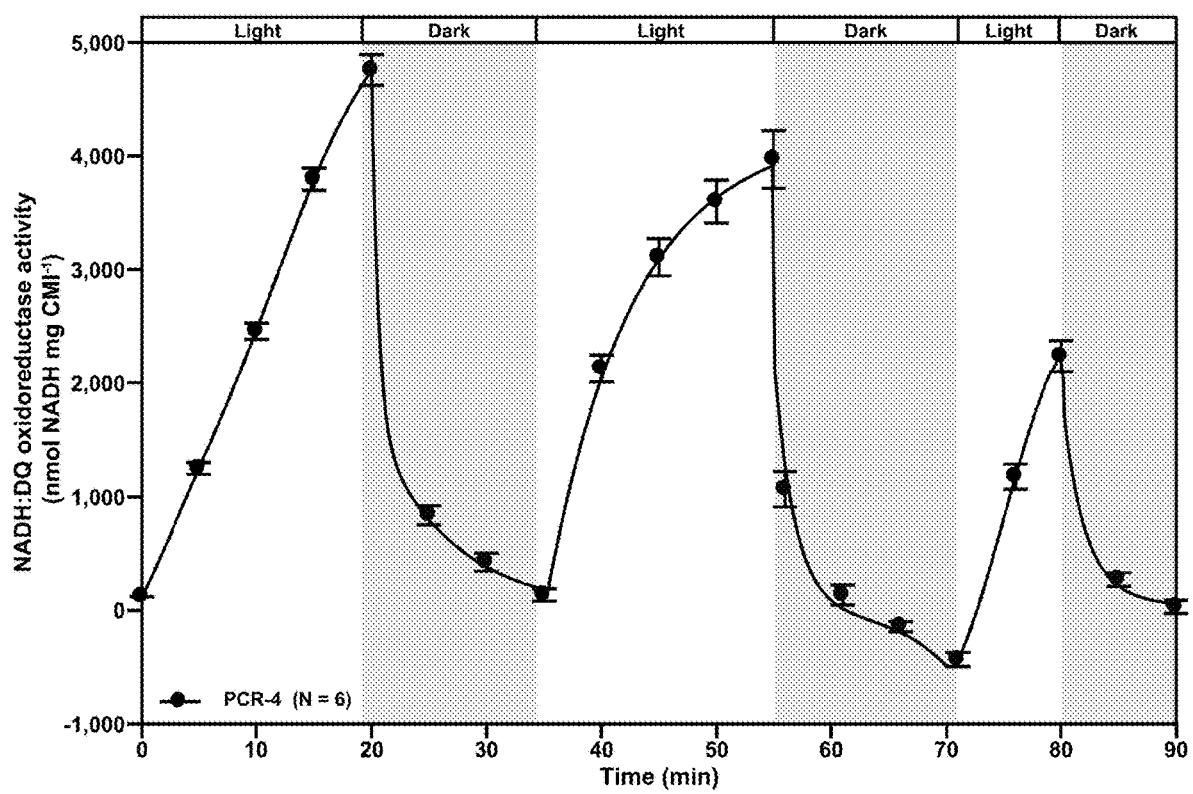
FIG. 11A-B show the photoreduction of $NAD^+$ by PCR-4 proteoliposomes through multiple light-dark cycles.
Figure 11B:
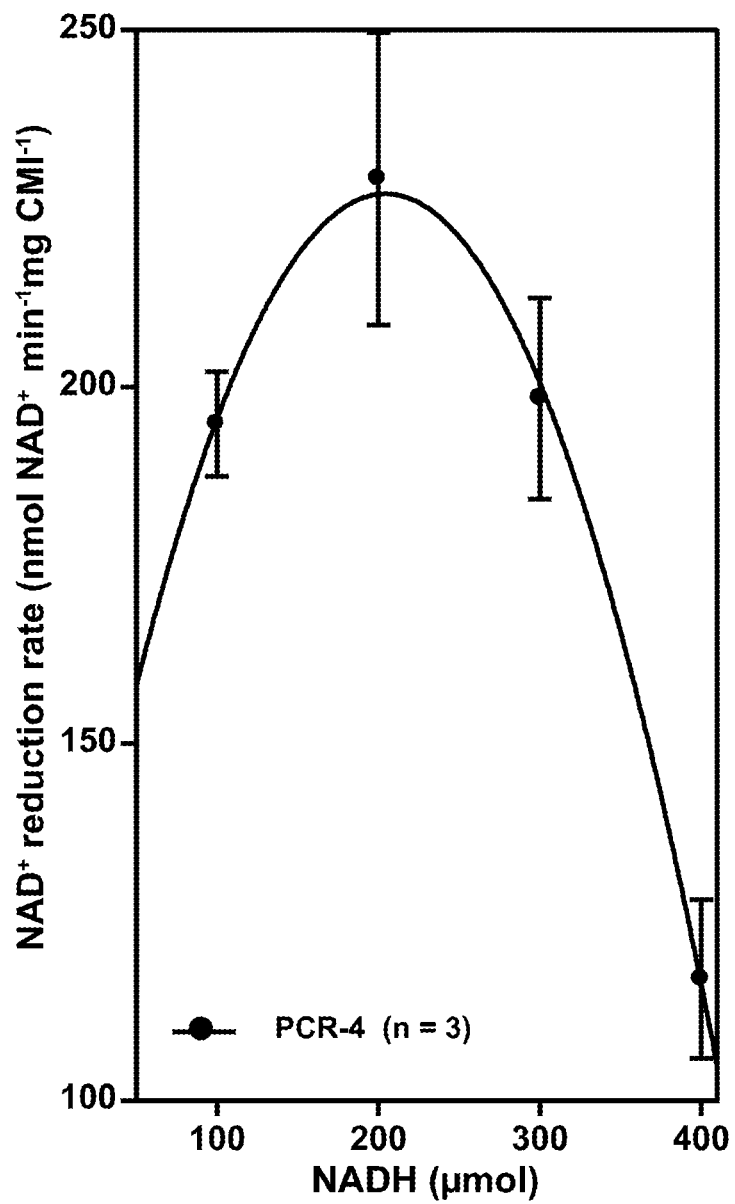

Results of $NAD^+$ photoreduction assays after exposure to light for greater than 10-20 minutes caused the rate of $NAD^+$ reduction to reduce significantly, similar to the plateau seen between 10-25 min for the non-inhibited sample in FIG. 9B. To determine if this phenomenon is due to disruption to the integrity of the system, light-dark cycle photoreduction experiments were performed (FIG. 11A) and FIG. 11C show NADH:DQ oxidoreductase activity; FIG. 11B shows ACMA signal). During the first two light-dark cycles of 20 mins the maximum rates of $NAD^+$ reduction increased from 185.34±59.06 to 319.53±22.33 nmol $min^{-1}$ mg $CMI^{-1}$. This suggests the function of the construct remains, meaning NADH must have an inhibitory effect on the RET for CMI.

To strengthen this conclusion, a NADH titration experiment was performed (FIG. 12, Table 6) to support this conclusion. Little has been published on RET for E. coli CMI, however it is reported for the ATP-driven, succinate-supported RET in SMPs [46]. Without being bound by theory, given the highly conservative nature of CMI between species, it would be logical that NADH could have an inhibitory effect on RET in this system.

TABLE 6

Results from NADH Titration Experiment

| NADH (µM) Injected | Max Rate $NAD^+$ Photoreduction (nmol $min^{-1}$ mg $CMI^{-1}$) | Max Production of NADH (µM) | NADH (µM) remaining prior to photoreduction | Sum NADH (µM) |
|---|---|---|---|---|
| 100 | 132.30 | 8.04 | 2.05 | 10.08 |
| 200 | 213.32 | 9.10 | 4.10 | 13.20 |
| 300 | 178.71 | 6.48 | 8.19 | 14.67 |
| 400 | 57.45 | 1.53 | 13.41 | 14.94 |

CONCLUSIONS BASED ON EXAMPLES

The results described herein demonstrate an engineered system which successively couples the activity of two multi-subunit membrane protein complexes that do not directly interact naturally for reduction of $NAD^+$. This system only consumes light and water, presenting a step forward in the development of a highly-versatile system that could be readily adapted for any isolated enzyme system requiring NADH recycling. This technology offers significant advantages over current techniques for NADH regeneration that utilize enzymes by eliminating the need for designing a rational reaction route in tandem with developing an efficient separation technology for removal of by-product [2]. This technology will enable the adoption of isolated enzyme systems for sequestration of $CO_2$ as no $CO_2$ is produced from this platform in contrast to many enzyme-based NADH regeneration methods [2-3, 5].

Based on the results herein and the fact that the function of PSII and CMI are conserved across species and between kingdoms, it can be soundly predicted that PSII and CMI from any species can be used in other embodiments to perform the same function as the tested PSII from *Cyanobacterium synechocystis* 6803 (*Synechocystis* sp. PCC6803) and CMI from *E. coli*. Based on the fact that variants of CMI have been engineered to have increased affinity for NADP$^+$/NADH, NADP$^+$ can be regenerated in other similar embodiments. Based on the fact that many analogues of ubiquinone are known in addition to the tested decylubiquinone, other analogues of ubiquinone or decylubiquinone can be used as the electron carrier in other embodiments. Based on the fact that water and light are the only input reactants, while oxygen is the only byproduct, some embodiments described herein can be used in any primary reaction system requiring regeneration of NADH or NADPH, because the water and oxygen are unlikely to interfere with the primary reaction system. Based on the fact that biomimetic membranes, for example based on triblock copolymers, are known to be able to stabilize and permit functioning of membrane proteins, other biomimetic membranes can be used in other embodiments, and embodiments described herein are not limited to the use of a lipid bilayer membrane. While valinomycin was used in the tested embodiments, a proton gradient is still established without the presence of valinomycin, and accordingly valinomycin can be omitted in some embodiments, or alternatively any suitable ionophore can be used in place of valinomycin.

Example 6

Purification of NADH:Ubiquinone Oxidoreductase (Complex I)

Purification of *E. coli* CMI was performed as described above.

Purification of Bacteriorhodopsin

Bacteriorhodopsin from *H. salinarum* was purified using tangential flow filtration, followed by solubilization with 5% (w/w) Trion X-100 at 1 mg ml$^{-1}$ for 24 hours. Solubilized bR was captured and detergent was exchanged using anion exchange chromatography.

Liposome preparation, enzyme reconstitution, NAD$^+$ photoreduction, and proton pumping assays were performed as described above.

Example 7

In this study, an engineered artificial organelle capable of photoreduction of NAD$^+$ was created by vectorially integrating bR from *H. salinarum* and CMI from *E. coli* into proteoliposomes. The power source for this system is light which activates the proton translocation by bR. As a result, accumulation of H$^+$ within the lumen creates a proton motive force (PMF). The PMF is requisite to diminish the thermodynamic gap of the standard redox potentials between NADH/NAD$^+$ and QH$_2$/Q. Reducing the thermodynamic barrier enables CMI to perform reverse electron transfer (RET) from QH$_2$ to NAD$^+$ [10, 46]. Combing the associated actives of these two enzymes demonstrates the foundation of a platform for NADH recycling for cell free metabolic systems.

The experiments were initially conducted to determine whether the (+)CMI-(+)bR proteoliposomes could reduce NAD$^+$ and find suitable assay conditions.

Other publications suggest RET by CMI has a higher dependence on the $\Delta$pH then the $\Delta\psi$ electrical component of the PMF for RET [42]. To generate a higher $\Delta$pH, valinomycin was included in the assay. Valinomycin is a potassium ionophore and in turn, eliminates the electrical component of the PMF allowing bR to generate higher pH gradients [47]. However, it has reported that high concentrations of valinomycin can have an inhibitory effect on bR [48]. Two concentrations of valinomycin were tested: 0.1 µM and 0.2 µM. There is significant and moderately strong correlation (r>0.44) and between valinomycin concentrations and NAD$^+$ reductase rate only when Piericidin A is present. In proton pumping assays 0.2 µM valinomycin quenched the ACMA more than 0.1 µM. The results of the experiments agree with other reports that RET by CMI has a higher dependence on $\Delta$pH then $\Delta\psi$; 0.2 µM valinomycin was used in additional experiments.

Reactive oxygen species (ROS) generation by mammalian CMI during RET is well documented [49]. Published information is limited for RET by *E. coli* CMI but, given the conservative nature of CMI between species, it is logical that bacterial CMI would also produce ROS during RET. To mitigate the possible detrimental effects that ROS would have on the system, dithiothreitol (DTT) was tested to determine whether it would have a positive effect of NAD$^+$ reduction. When 1.0 mM DTT was present that there is a significant (p-value <0.01) and adverse effect on the reduction of NAD$^+$ whereas 0.2 mM and 0.4 mM had no significant effect. These results were unexpected, and the cause for these findings are outside the scope of this work but may be caused by the electron transfer reactions between the FMN containing active site of CMI with DTT [50].

Figure 12:
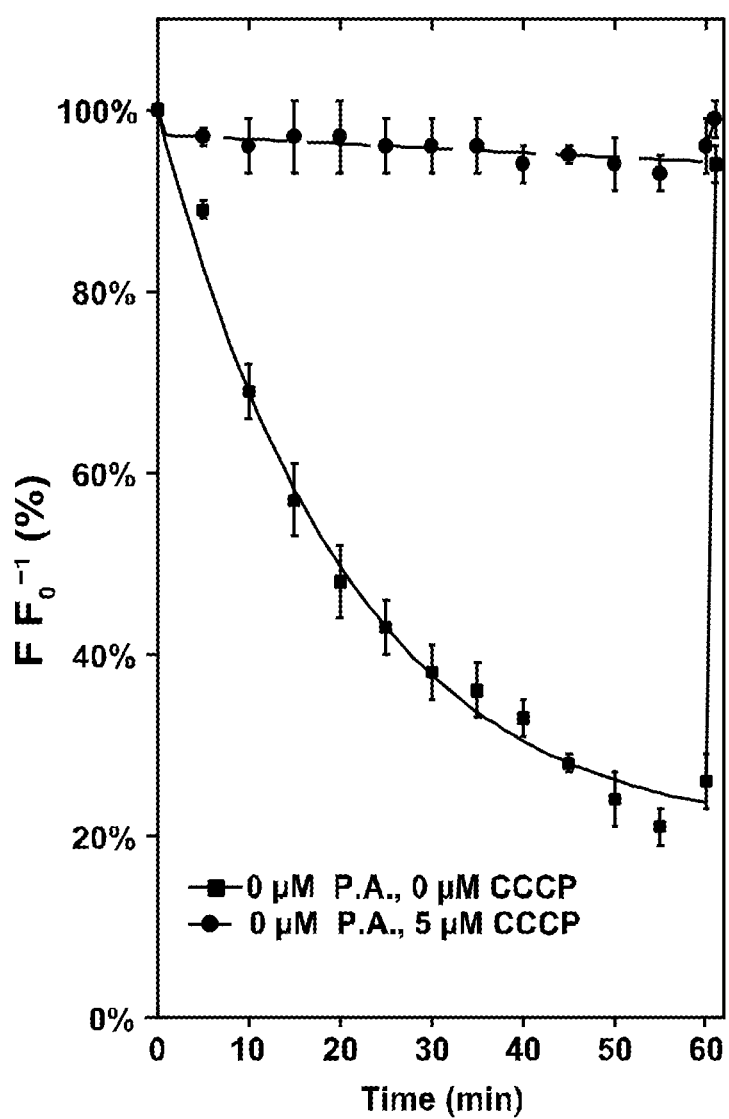
FIG. 12 shows proton pumping by bacteriorhodopsin from *H. salinarum* (bR). Typical results from (−)CMI-(+)bR proteoliposomes. Samples were incubated for 5 min. to allow the ACMA signal to stabilize before starting the experiments. After 60 min, 5 μM CCCP was added to abolish the proton gradient. The results are the representation of three technical repeats of 5 biological replicates.
Figure 13A:
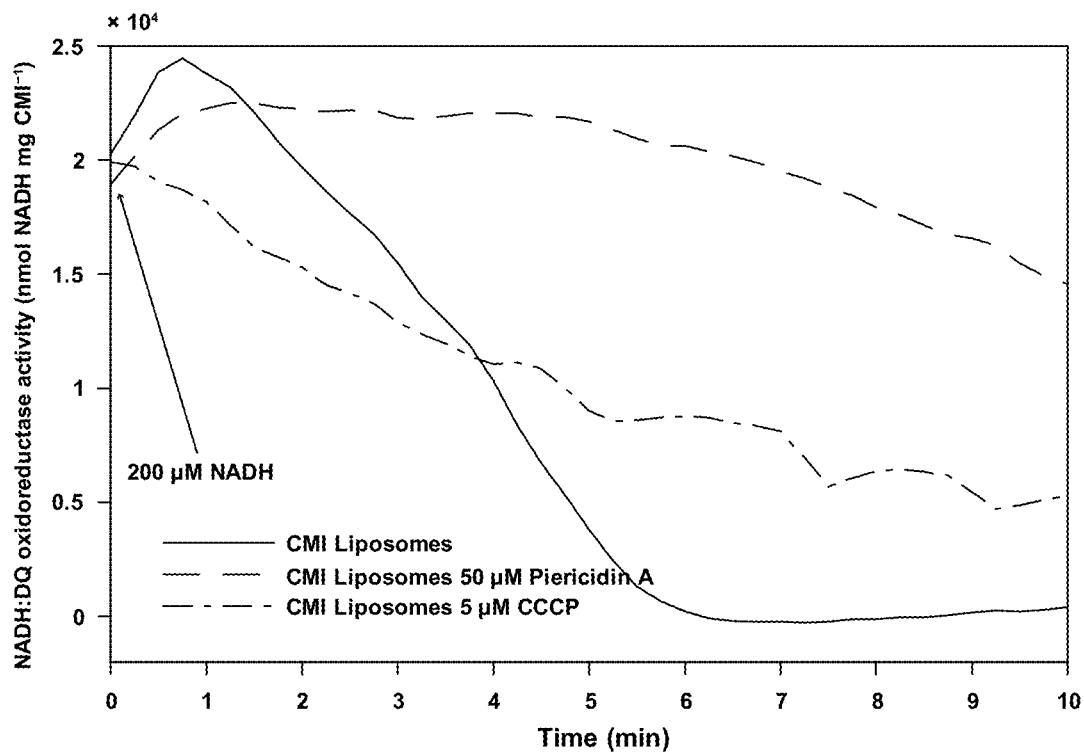
FIG. 13A-C shows proton pumping and inhibition of NADH oxidation in (+)CMI-(−)bR proteoliposomes.
Figure 13B:
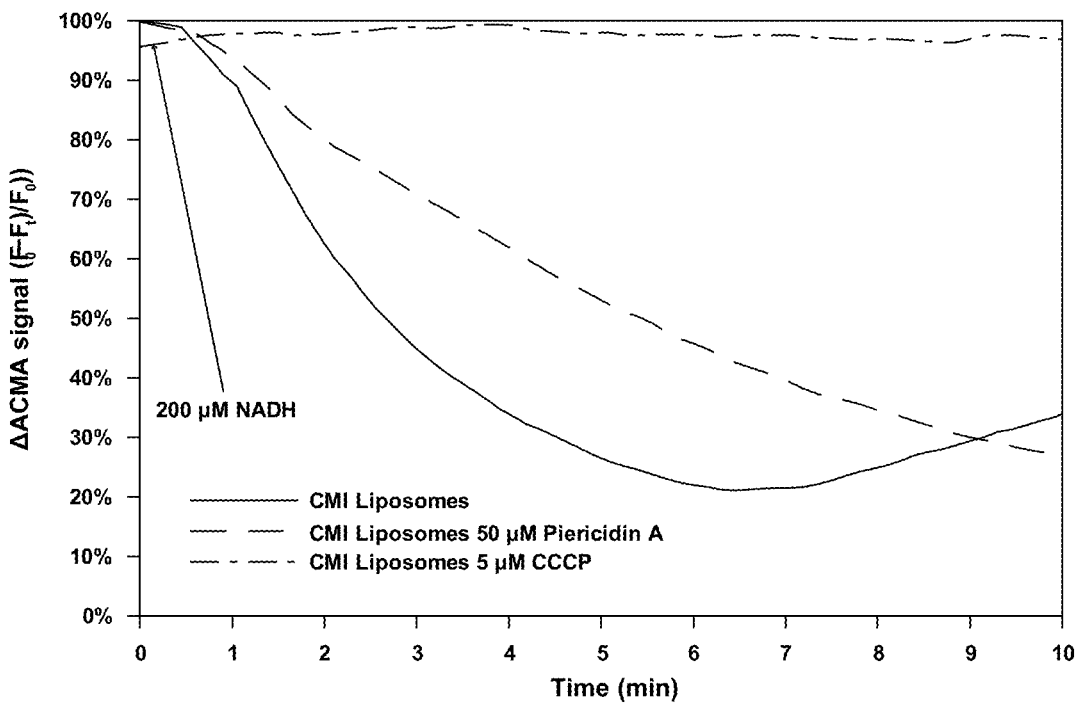
Figure 13C:
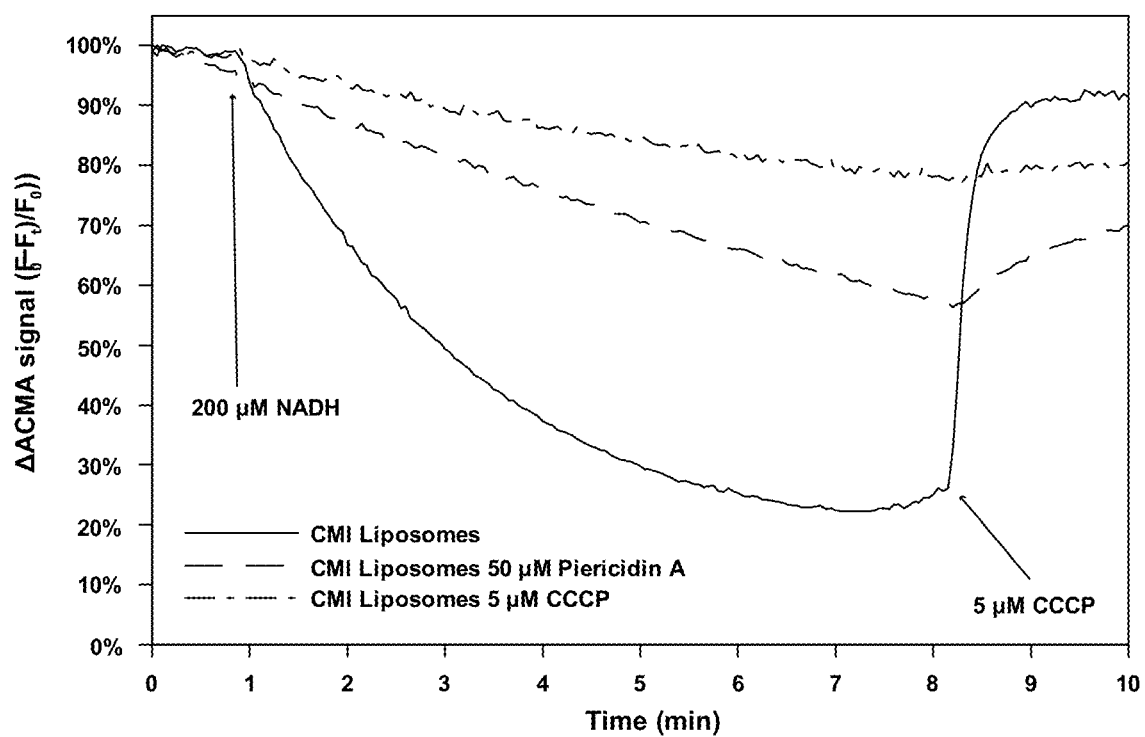

One of the most significant findings in this work was the effect of Piericidin A on the reduction of NAD$^+$. Piericidin A is a well-known and potent inhibitor of the oxidation of NADH by CMI [51]. When 50 µM Piericidin A was included, NADH oxidation was inhibited >95% however, the NAD$^+$ reductase rates were significantly increased with a strong positive correlation coefficient (r>0.92) (FIG. 12-13). This finding was most prominent in the in experiments that contained 0.0 and 1.0 mM DTT (data not shown), resulting in rates nearly 3 and 4 times that of samples which contain no Piericidin A. Kotlyar et al. reported similar findings for the inhibitor rotenone in CMI from *Paracoccus denitrificans* [16]. The two-quinone binding sites may explain the inability for Piericidin A to inhibit RET [52-53].

To confirm that NADH is produced, control experiments were performed at multiple points along the mechanism of the system. Proteoliposomes that did not contain bR were tested for confirmation that bR was providing a $\Delta$pH to activate RET by CMI. When incorporating bR into the proteoliposomes with CMI, there was a significant difference with strong positive correlation coefficients for all conditions tested indicating that bR is responsible for creating a $\Delta$pH. Samples incubated under light and dark conditions were tested. When the samples were incubated in the dark, they produced little or no NADH. Light was responsible for the NADH production through the activation of bR (r>0.96). Additionally, the experiments showed no significant difference between the (−)bR samples and the (−)Light samples and similar slopes in the response found in (±)bR. Moreover, to determine if the $\Delta$pH generated by bR was necessary for NADH production, 5 µM CCCP, a protonophore was included (not shown). With CCCP present, a $\Delta$pH is unable to establish and results in negative and significant response (p-value <0.001 and <0.0001, r<−0.95 for 0.0 and 1.0 mM DTT respectively).

Figure 14:
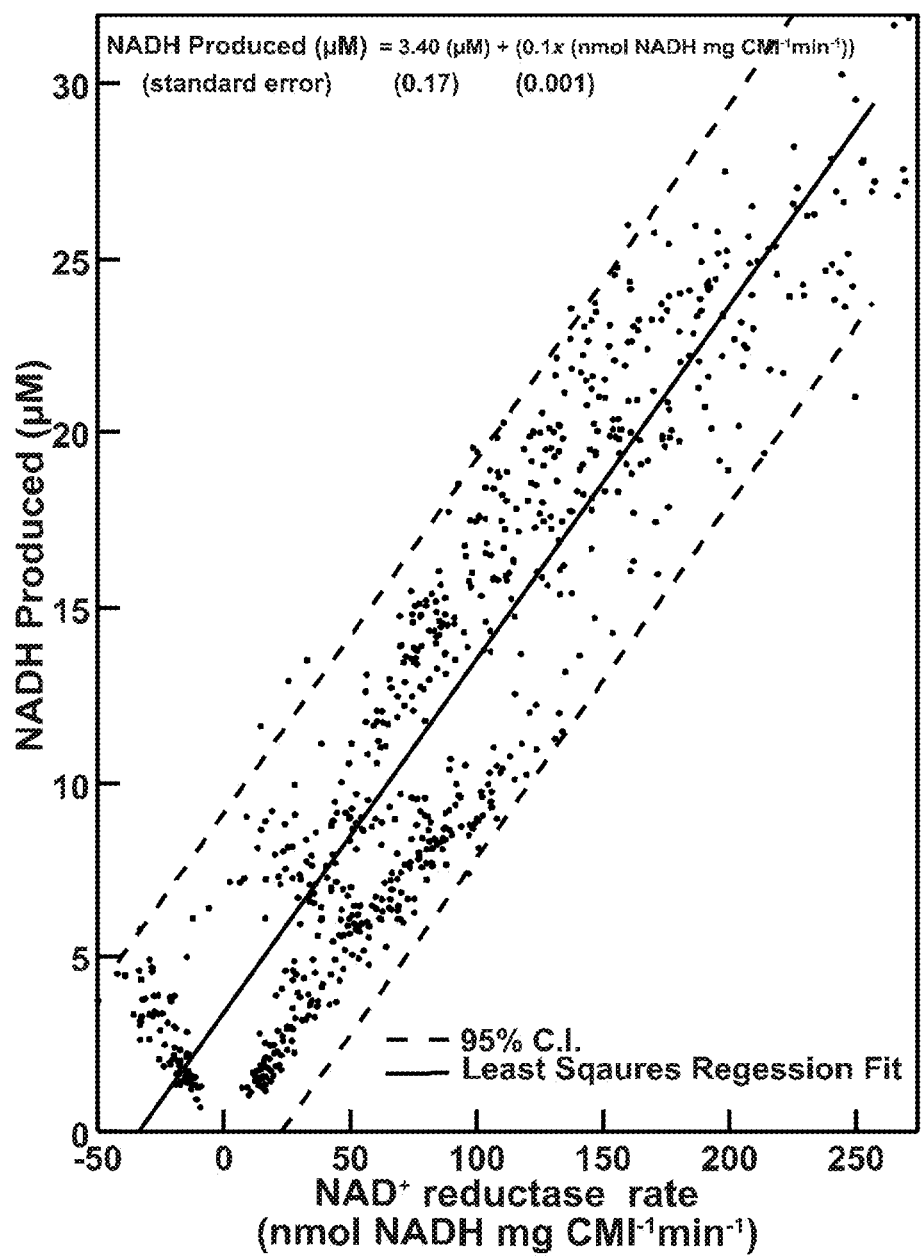
FIG. 14. The relationship between NAD⁺ reductase rate (nmol NADH mg CMI$^{-1}$ min$^{-1}$) and NADH producted (μM). The formula for the linear less squares fit is shown in the figure legend (p-value >0.0001, R$^2$>0.85). The fit was generated using all observations (N=732) from all conditions tested.

To determine if the rate of $NAD^+$ reductase had a relationship to the total NADH produced (μM) a linear least squares regression was performed on 734 observations (N=762) of (+)CMI-(+)bR proteoliposomes, under all conditions tested (FIG. 14). The estimated gradient 0.1±0.002 (mg CMI $min^{-1}$ nmol $NADH^{-1}$), predicts an increase in $NAD^+$ reductase rate of 10 (NADH mg $CMI^{-1}$ $min^{-1}$) with increase the NADH produced by 1 μM. The effect is small and statistically significant and the coefficient of correlation (r>0.92) indicates a strong positive linear relationship. Although several data points are negative slopes with a net production in NADH, the rates are the absolute maximum steady state values while the NADH produced represents a localized maximum.

The pH-sensitive fluorophore 9-amino-6-chloro-2-methoxyacridine (ACMA) was used to conduct proton pumping assays. The rates of ACMA quenching were measured for CMI bR independently. Because of the non-linear relationship between ACMA quenching and $\Delta pH$ [54-55], the rate of ACMA quenching and de-quenching were calculated using the linear region of the ACMA signal, between 40-70% of the baseline. Light-induced activation of bR causes the ACMA signal to decrease at a rate of −1.51±0.62 ACMA % $min^{-1}$. During photoreduction of samples with no Piericidin A. present (data not shown), the signal increased by 1.63±0.15 and 1.34±0.37 ACMA % $min^{-1}$ for 0.0 and 1.0 mM DTT, respectively. When 50 μM Piericidin A was present the rate the signal increased nearly doubled to 3.96±0.64 and 3.15±0.94 ACMA % $min^{-1}$ for 0.0 and 1.0 mM DTT, respectively. These results are in good agreement with measured rates of $NAD^+$
reduction for two reasons. Since ACMA reports the signal for the entire population of proteoliposomes and Piericidin A only inhibits the oxidation of NADH by CMI, proteoliposomes may be oxidizing NADH and simultaneously reduced by another population. Furthermore, when Piericidin A is present the rate of NADH produced reduces by 95% after 35 minutes while with no Piericidin A the rate reduced by 72% (data not shown). There is effectively no $\Delta pH$ remaining for CMI to reduce $NAD^+$ after 35 min when Piericidin A is present in comparison to when Piericidin A not present, a $\Delta pH$ is present for the all but the last 5 min of the 60-min assay.

Another interesting finding from the proton pumping assays occurring during the initial 5 mins of illumination. When Piericidin A is not present there is an initial decrease of ACMA quenching before dequenching and starting NADH production which is not evident when Piericidin A is present or in dark incubated samples (data not shown). The ACMA data is difficult to precisely decouple the actions of each of the two enzymes but, the initial decrease in ACMA signal can be attributed to a charging of the system by bR. This observation indicates that RET through CMI may require a specific magnitude of $\Delta pH$ before switching on and continuing.

These results demonstrate the assembly and testing of an artificial organelle comprising bacteriorhodopsin from *Halobacterium salinarum* and *E. coli* CMI that enables reduction of $NAD^+$. The significances of findings reported here are that the reversible machine CMI can utilize a $\Delta pH$ to transfer electrons from $QH_2$ to $NAD^+$ while the addition of Piericidin A enhances $NAD^+$ reduction by inhibiting the oxidation of NADH by CMI. This, in turn, allows NADH to be readily available for other synthetic biochemical reaction pathways.

This research provides the foundation for further development of systems for power generation in in vitro metabolic systems. Additionally, this technology reduces the constraints on designing metabolic pathways found in other methods for maintaining redox balance, enabling development of more diverse and complex cell free metabolic systems. Coupling this system, with ATP-producing artificial organelles, will permit the creation biological energy power systems for various applications.

SEQUENCE LISTING

```
Sequence total quantity: 34
SEQ ID NO: 1            moltype = AA  length = 507
FEATURE                 Location/Qualifiers
source                  1..507
                        mol_type = protein
                        organism = Synechocystis sp.
SEQUENCE: 1
MGLPWYRVHT VVLNDPGRLI SVHLMHTALV AGWAGSMALY ELAIFDSSDA VLNPMWRQGM  60
FVLPFMARLG VTSSWNGWSV TGETGLDPGF WSFEGVAAAH IVLSGLLFLA AVWHWVFWDL 120
ELFVDPRTGE SALDLPKMFG IHLFLSGLLC FGFGAFHLTG VWGPGMWVSD PYGLTGHVQP 180
VAPEWGPAGF NPFNPGVVA  HHIAAGIVGI IAGLFHLTVR PPERLYKALR MGNIETVLSS 240
SIAAVFFAAF VVAGTMWYGN ATTPIELFGP TRYQWDKGYF QEEIQRRVDS QLAEGASLSE 300
AWSTIPEKLA FYDYVGNSPA KGGLFRTGAM NSGDGIAQEW IGHPIFKDKE GRELEVRRMP 360
NFFETFPVIM TDADGVVRAD IPFRRSESKF SVEQTGVTVS FYGGALDGQT FSNPSDVKKF 420
ARKAQLGEGF DFDTETFNSD GVFRTSPRGW FTFGHAVFAL LFFFGHIWHG SRTLFRDVFA 480
GVDPGLEEQV EFGVFAKVGD LSTRKEA                                    507

SEQ ID NO: 2            moltype = AA  length = 460
FEATURE                 Location/Qualifiers
source                  1..460
                        mol_type = protein
                        organism = Synechocystis sp.
SEQUENCE: 2
MVTLSNTSMV GGRDLPSTGF AWWSGNARLI NLSGKLLGAH VAHAGLIVFW AGAMTLFEVA  60
HFIPEKPMYE QGLILLPHIA TLGWGVGPAG EVTDIFPFFV VGVLHLISSA VLGLGGIYHA 120
LRGPEVLEEY SSFFGYDWKD KNQMTNIIGY HLILLGCGAL LLVFKAMFFG GVYDTWAPGG 180
GDVRVITNPT LNPAIIFGYL LKAPFGGEGW IISVNNMEDI IGGHIWIGLI CISGGIWHIL 240
TKPFGWARRA LIWSGEAYLS YSLGALSLMG FIASVFVWFN NTAYPSEFYG PTGMEASQSQ 300
AFTFLVRDQR LGANIASAQG PTGLGKYLMR SPSGEIIFGG ETMRFWDFRG PWLEPLRGPN 360
```

```
GLDLDKLRND IQPWQVRRAA EYMTHAPLGS LNSVGGVITD VNSFNYVSPR AWLATSHFVL    420
GFFFLVGHLW HAGRARAAAA GFEKGIDRET EPTLFMPDLD                         460

SEQ ID NO: 3              moltype = AA   length = 64
FEATURE                   Location/Qualifiers
source                    1..64
                          mol_type = protein
                          organism = Synechocystis sp.
SEQUENCE: 3
MAQRTRLGDI LRPLNSEYGK VVPGWGTTPV MGVFMALFLV FLLIILQIYN SSLILEGFSV    60
DWAG                                                                64

SEQ ID NO: 4              moltype = AA   length = 38
FEATURE                   Location/Qualifiers
source                    1..38
                          mol_type = protein
                          organism = Synechocystis sp.
SEQUENCE: 4
MLTLKIAVYI VVGLFISLFI FGFLSSDPTR NPGRKDFE                            38

SEQ ID NO: 5              moltype = AA   length = 39
FEATURE                   Location/Qualifiers
source                    1..39
                          mol_type = protein
                          organism = Synechocystis sp.
SEQUENCE: 5
MFAEGRIPLW VVGVVAGIGA IGVLGLFFYG AYAGLGSSM                           39

SEQ ID NO: 6              moltype = AA   length = 45
FEATURE                   Location/Qualifiers
source                    1..45
                          mol_type = protein
                          organism = Synechocystis sp.
SEQUENCE: 6
METIYLLAKL PEAYQIFDPL VDVLPVIPLF FLALAFVWQA AVGFK                    45

SEQ ID NO: 7              moltype = AA   length = 39
FEATURE                   Location/Qualifiers
source                    1..39
                          mol_type = protein
                          organism = Synechocystis sp.
SEQUENCE: 7
MDRNSNPNRQ PVELNRTSLY LGLLLVAVLG ILFSSYFFN                           39

SEQ ID NO: 8              moltype = AA   length = 35
FEATURE                   Location/Qualifiers
source                    1..35
                          mol_type = protein
                          organism = Synechocystis sp.
SEQUENCE: 8
MQVNNLGFIA SILFVLVPTV FLLILFIQTG KQSES                               35

SEQ ID NO: 9              moltype = AA   length = 31
FEATURE                   Location/Qualifiers
source                    1..31
                          mol_type = protein
                          organism = Synechocystis sp.
SEQUENCE: 9
MESVAYILVL TMALAVLFFA IAFREPPRIE K                                   31

SEQ ID NO: 10             moltype = AA   length = 39
FEATURE                   Location/Qualifiers
source                    1..39
                          mol_type = protein
                          organism = Synechocystis sp.
SEQUENCE: 10
MTPSLANFLW SLVLGAAIVL IPATVGLIFI SQKDKITRS                           39

SEQ ID NO: 11             moltype = AA   length = 39
FEATURE                   Location/Qualifiers
source                    1..39
                          mol_type = protein
                          organism = Synechocystis sp.
SEQUENCE: 11
MDWRVIVVVS PLLIAATWAA INIGAAAIRQ LQDVLGREA                           39
```

```
SEQ ID NO: 12            moltype = AA  length = 39
FEATURE                  Location/Qualifiers
source                   1..39
                         mol_type = protein
                         organism = Synechocystis sp.
SEQUENCE: 12
MELLAALNLE PIFQLTFLGL IVLAGPAVVF VLAFRGGDL                            39

SEQ ID NO: 13            moltype = AA  length = 62
FEATURE                  Location/Qualifiers
source                   1..62
                         mol_type = protein
                         organism = Synechocystis sp.
SEQUENCE: 13
MSIVFQIALA ALVLFSFVMV VGVPVAYASP QNWDRSKPLL YLGSGIWAIL VIVVALLNFL     60
VV                                                                   62

SEQ ID NO: 14            moltype = AA  length = 112
FEATURE                  Location/Qualifiers
source                   1..112
                         mol_type = protein
                         organism = Synechocystis sp.
SEQUENCE: 14
MAEIQFSKGV AETVVPEVRL SKSKNGQSGM AKFYFLEPTI LAKESTDDIT GMYLIDDEGE     60
IITREVKGKF INGRPTAIEA TVILNSQPEW DRFMRFMERY GAENGLGFSK SE            112

SEQ ID NO: 15            moltype = AA  length = 360
FEATURE                  Location/Qualifiers
source                   1..360
                         mol_type = protein
                         organism = Synechocystis sp.
SEQUENCE: 15
MTTTQLGLQE QSLWSRFCCW ITSTSNRLYI GWFGVLMIPT LLTATTCFII AFIAAPPVDI     60
DGIREPIAGS LLYGNNIITA AVVPSSNAIG LHFYPIWEAH SLDEWLYNGG PYQLIVFHFL    120
IGIFCYLGRQ WELSYRLGMR PWICVAYSAP VAAATATLLI YSIGQGSFSD GLPLGISGTF    180
NFMLVLQAEH NVLMHPFHML GVAGVFGGAL FAAMHGSLVT SSLIRETTEV ESQNQGYKFG    240
QEEETYNIVA AHGYFGRLIF QYASFNNSRA LHFFLGAWPV VGIWFAALAV CCFAFNLNGF    300
NFNQSILDAQ GRPVSTWADV INRANIGFEV MHERNVHNFP LDLASGDAQM VALNAPAIEG    360

SEQ ID NO: 16            moltype = AA  length = 360
FEATURE                  Location/Qualifiers
source                   1..360
                         mol_type = protein
                         organism = Synechocystis sp.
SEQUENCE: 16
MTTTLQQRES ASLWEQFCQW VTSTNNRIYV GWFGTLMIPT LLTATTCFII AFIAAPPVDI     60
DGIREPVAGS LLYGNNIISG AVVPSSNAIG LHFYPIWEAA SLDEWLYNGG PYQLVVFHFL    120
IGIFCYMGRQ WELSYRLGMR PWICVAYSAP VSAATAVFLI YPIGQGSFSD GMPLGISGTF    180
NFMIVFQAEH NILMHPFHML GVAGVFGGSL FSAMHGSLVT SSLVRETTEV ESQNYGYKFG    240
QEEETYNIVA AHGYFGRLIF QYASFNNSRS LHFFLGAWPV IGIWFTAMGV STMAFNLNGF    300
NFNQSILDSQ GRVIGTWADV LNRANIGFEV MHERNAHNFP LDLASGEQAP VALTAPAVNG    360

SEQ ID NO: 17            moltype = AA  length = 352
FEATURE                  Location/Qualifiers
source                   1..352
                         mol_type = protein
                         organism = Synechocystis sp.
SEQUENCE: 17
MTIAVGRAPV ERGWFDVLDD WLKRDRFVFI GWSGLLLFPC AFMALGGWLT GTTFVTSWYT     60
HGLASSYLEG ANFLTVAVSS PADAFGHSLL FLWGPEAQGN LTRWFQIGGL WPFVALHGAF    120
GLIGFMLRQF EISRLVGIRP YNAIAFSGPI AVFVSVFLMY PLGQSSWFFA PSFGVAGIFR    180
FILFLQGFHN WTLNPFHMMG VAGILGGALL CAIHGATVEN TLFEDGEDSN TFRAFEPTQA    240
EETYSMVTAN RFWSQIFGIA FSNKRWLHFF MLFVPVTGLW MSSVGIVGLA LNLRAYDFVS    300
QELRAAEDPE FETFYTKNIL LNEGMRAWMA PQDQPHENFI FPEEVLPRGN AL            352

SEQ ID NO: 18            moltype = AA  length = 274
FEATURE                  Location/Qualifiers
source                   1..274
                         mol_type = protein
                         organism = Synechocystis sp.
SEQUENCE: 18
MRFRPSIVAL LSVCFGLLTF LYSGSAFAVD KSQLTYDDIV NTGLANVCPE ISSFTRGTIE     60
VEPNTKYFVS DFCMEPQEYF VKEEPVNKRQ KAEYVKGKVL TRQTTSLEQI RGSIAVGADG    120
TLTFKEKDGI DFQPITVLLP GGEEVPFFFT VKNFTGTTEP GFTSINSSTD FVGDFNVPSY    180
RGAGFLDPKA RGLYTGYDNA VALPSAADKF RTNKKETPLG KGTLSLQVTQ VDGSTGEIAG    240
IFESEQPSDT DLGAKEPLDV KVRGIFYGRV DTDV                                274

SEQ ID NO: 19            moltype = AA  length = 134
```

```
FEATURE                 Location/Qualifiers
source                  1..134
                        mol_type = protein
                        organism = Synechocystis sp.
SEQUENCE: 19
MSFLKNQLSR LLALILVVAI GLTACDSGTG LTGNYSQDTL TVIATLREAI DLPQDAPNRQ    60
EVQDTARGQI NDYISRYRRK GDAGGLKSFT TMQTALNSLA GYYTSYGARP IPEKLKKRLQ   120
LEFTQAERSI ERGV                                                    134

SEQ ID NO: 20           moltype = AA  length = 131
FEATURE                 Location/Qualifiers
source                  1..131
                        mol_type = protein
                        organism = Synechocystis sp.
SEQUENCE: 20
MKFISRLLVA CSLLIGLMGF LGADLAQALT PNPILAELNA VDAKLTTDFG QKIDLNNSDI    60
RDFRGLRGFY PNLASEIIKN APYDTVEEVL DIPGLSETQK SRLEANLGSF TVTEPSIELT   120
SGDDRINPGV Y                                                       131

SEQ ID NO: 21           moltype = AA  length = 262
FEATURE                 Location/Qualifiers
source                  1..262
                        mol_type = protein
                        organism = Halobacterium salinarum
SEQUENCE: 21
MLELLPTAVE GVSQAQITGR PEWIWLALGT ALMGLGTLYF LVKGMGVSDP DAKKFYAITT    60
LVPAIAFTMY LSMLLGYGLT MVPFGGEQNP IYWARYADWL FTTPLLLLDL ALLVDADQGT   120
ILALVGADGI MIGTGLVGAL TKVYSYRFVW WAISTAAMLY ILYVLFFGFT SKAESMRPEV   180
ASTFKVLRNV TVVLWSAYPV VWLIGSEGAG IVPLNIETLL FMVLDVSAKV GFGLILLRSR   240
AIFGEAEAPE PSAGDGAAAT SD                                           262

SEQ ID NO: 22           moltype = AA  length = 147
FEATURE                 Location/Qualifiers
source                  1..147
                        mol_type = protein
                        organism = Escherichia coli
SEQUENCE: 22
MSMSTSTEVI AHHWAFAIFL IVAIGLCCLM LVGGWFLGGR ARARSKNVPF ESGIDSVGSA    60
RLRLSAKFYL VAMFFVIFDV EALYLFAWST SIRESGWVGF VEAAIFIFVL LAGLVYLVRI   120
GALDWTPARS RRERMNPETN SIANRQR                                      147

SEQ ID NO: 23           moltype =     length =
SEQUENCE: 23
000

SEQ ID NO: 24           moltype = AA  length = 596
FEATURE                 Location/Qualifiers
source                  1..596
                        mol_type = protein
                        organism = Escherichia coli
SEQUENCE: 24
MTDLTAQEPA WQTRDHLDDP VIGELRNRFG PDAFTVQATR TGVPVVWIKR EQLLEVGDFL    60
KKLPKPYVML FDLHGMDERL RTHREGLPAA DFSVFYHLIS IDRNRDIMLK VALAENDLHV   120
PTFTKLFPNA NWYERETWDL FGITFDGHPN LRRIMMPQTW KGHPLRKDYP ARATEFSPFE   180
LTKAKQDLEM EALTFKPEEW GMKRGTENED FMFLNLGPNH PSAHGAFRIV LQLDGEEIVD   240
CVPDIGYHHR GAEKMGERQS WHSYIPYTDR IEYLGGCVNE MPYVLAVEKL AGITVPDRVN   300
VIRVMLSELF RINSHLLYIS TFIQDVGAMT PVFFAFTDRQ KIYDLVEAIT GFRMHPAWFR   360
IGGVAHDLPR GWDRLLREFL DWMPKRLASY EKAALQNTIL KGRSQGVAAY GAKEALEWGT   420
TGAGLRATGI DFDVRKARPY SGYENFDFEI PVGGGVSDCY TRVMLKVEEL RQSLRILEQC   480
LNNMPEGPFK ADHPLTTPPP KERTLQHIET LITHFLQVSW GPVMPANESF QMIEATKGIN   540
SYYLTSDGST MSYRTRVRTP SFAHLQQIPA AIRGSLVSDL IVYLGSIDFV MSDVDR       596

SEQ ID NO: 25           moltype = AA  length = 166
FEATURE                 Location/Qualifiers
source                  1..166
                        mol_type = protein
                        organism = Escherichia coli
SEQUENCE: 25
MHENQQPQTE AFELSAAERE AIEHEMHHYE DPRAASIEAL KIVQKQRGWV PDGAIHAIAD    60
VLGIPASDVE GVATFYSQIF RQPVGRHVIR YCDSVVCHIN GYQGIQAALE KKLNIKPGQT   120
TFDGRFTLLP TCCLGNCDKG PNMMIDEDTH AHLTPEAIPE LLERYK                 166

SEQ ID NO: 26           moltype = AA  length = 445
FEATURE                 Location/Qualifiers
source                  1..445
                        mol_type = protein
                        organism = Escherichia coli
SEQUENCE: 26
MKNIIRTPET HPLTWRLRDD KQPVWLDEYR SKNGYEGARK ALTGLSPDEI VNQVKDAGLK    60
```

```
GRGGAGFSTG LKWSLMPKDE SMNIRYLLCN ADEMEPGTYK DRLLMEQLPH LLVEGMLISA    120
FALKAYRGYI FLRGEYIEAA VNLRRAIAEA TEAGLLGKNI MGTGFDFELF VHTGAGRYIC    180
GEETALINSL EGRRANPRSK PPFPATSGAW GKPTCVNNVE TLCNVPAILA NGVEWYQNIS    240
KSKDAGTKLM GFSGRVKNPG LWELPFGTTA REILEDYAGG MRDGLKFKAW QPGGAGTDFL    300
TEAHLDLPME FESIGKAGSR LGTALAMAVD HEINMVSLVR NLEEFFARES CGWCTPCRDG    360
LPWSVKILRA LERGEGQPGD IETLEQLCRF LGPGKTFCAH APGAVEPLQS AIKYFREEFE    420
AGIKQPFSNT HLINGIQPNL LKERW                                         445

SEQ ID NO: 27           moltype = AA  length = 908
FEATURE                 Location/Qualifiers
source                  1..908
                        mol_type = protein
                        organism = Escherichia coli
SEQUENCE: 27
MATIHVDGKE YEVNGADNLL EACLSLGLDI PYFCWHPALG SVGACRQCAV KQYQNAEDTR     60
GRLVMSCMTP ASDGTFISID DEEAKQFRES VVEWLMTNHP HDCPVCEEGG NCHLQDMTVM    120
TGHSFRRYRF TKRTHRNQDL GPFISHEMNR CIACYRCVRY YKDYADGTDL GVYGAHDNVY    180
FGRPEDGTLE SEFSGNLVEI CPTGVFTDKT HSERYNRKWD MQFAPSICQQ CSIGCNISPG    240
ERYGELRRIE NRYNGTVNHY FLCDRGRFGY GYVNLKDRPR QPVQRRGDDF ITLNAEQAMQ    300
GAADILRQSK KVIGIGSPRA SVESNFALRE LVGEENFYTG IAHGEQERLQ LALKVLREGG    360
IYTPALREIE SYDAVLVLGE DVTQTGARVA LAVRQAVKGK AREMAAAQKV ADWQIAAILN    420
IGQRAKHPLF VTNVDDTRLD DIAAWTYRAP VEDQARLGFA IAHALDNSAP AVDGIEPELQ    480
SKIDVIVQAL AGAKKPLIIS GTNAGSLEVI QAAANVAKAL KGRGADVGIT MIARSVNSMG    540
LGIMGGGSLE EALTELETGR ADAVVVLEND LHRHASAIRV NAALAKAPLV MVVDHQRTAI    600
MENAHLVLSA ASFAESDGTV INNEGRAQRF FQVYDPAYYD SKTVMLESWR WLHSLHSTLL    660
SREVDWTQLD HVIDAVVAKI PELAGIKDAA PDATFRIRGQ KLAREPHRYS GRTAMRANIS    720
VHEPRQPQDI DTMFTFSMEG NNQPTAHRSQ VPFAWAPGWN SPQAWNKFQD EVGGKLRFGD    780
PGVRLFETSE NGLDYFTSVP ARFQPQDGKW RIAPYYHLFG SDELSQRAPV FQSRMPQPYI    840
KLNPADAAKL GVNAGTRVSF SYDGNTVTLP VEIAEGLTAG QVGLPMGMSG IAPVLAGAHL    900
EDLKEAQQ                                                            908

SEQ ID NO: 28           moltype = AA  length = 325
FEATURE                 Location/Qualifiers
source                  1..325
                        mol_type = protein
                        organism = Escherichia coli
SEQUENCE: 28
MSWISPELIE ILLTILKAVV ILLVVVTCGA FMSFGERRLL GLFQNRYGPN RVGWGGSLQL     60
VADMIKMFFK EDWIPKFSDR VIFTLAPMIA FTSLLLAFAI VPVSPGWVVA DLNIGILFFL    120
MMAGLAVYAV LFAGWSSNNK YSLLGAMRAS AQTLSYEVFL GLSLMGVVAQ AGSFNMTDIV    180
NSQAHVWNVI PQFFGFITFA IAGVAVCHRH PFDQPEAEQE LADGYHIEYS GMKFGLFFVG    240
EYIGIVTISA LMVTLFFGGW QGPLLPPFIW FALKTAFFMM MFILIRASLP RPRYDQVMSF    300
GWKICLPLTL INLLVTAAVI LWQAQ                                         325

SEQ ID NO: 29           moltype = AA  length = 180
FEATURE                 Location/Qualifiers
source                  1..180
                        mol_type = protein
                        organism = Escherichia coli
SEQUENCE: 29
MTLKELLVGF GTQVRSIWMI GLHAFAKRET RMYPEEPVYL PPRYRGRIVL TRDPDGEERC     60
VACNLCAVAC PVGCISLQKA ETKDGRWYPE FFRINFSRCI FCGLCEEACP TTAIQLTPDF    120
EMGEYKRQDL VYEKEDLLIS GPGKYPEYNF YRMAGMAIDG KDKGEAENEA KPIDVKSLLP    180

SEQ ID NO: 30           moltype = AA  length = 184
FEATURE                 Location/Qualifiers
source                  1..184
                        mol_type = protein
                        organism = Escherichia coli
SEQUENCE: 30
MEFAFYICGL IAILATLRVI THTNPVHALL YLIISLLAIS GVFFSLGAYF AGALEIIVYA     60
GAIMVLFVFV VMMLNLGGSE IEQERQWLKP QVWIGPAILS AIMLVVIVYA ILGVNDQGID    120
GTPISAKAVG ITLFGPYVLA VELASMLLLA GLVVAFHVGR EERAGEVLSN RKDDSAKRKT    180
EEHA                                                                184

SEQ ID NO: 31           moltype = AA  length = 100
FEATURE                 Location/Qualifiers
source                  1..100
                        mol_type = protein
                        organism = Escherichia coli
SEQUENCE: 31
MIPLQHGLIL AAILFVLGLT GLVIRRNLLF MLIGLEIMIN ASALAFVVAG SYWGQTDGQV     60
MYILAISLAA AEASIGLALL LQLHRRRQNL NIDSVSEMRG                          100

SEQ ID NO: 32           moltype = AA  length = 613
FEATURE                 Location/Qualifiers
source                  1..613
                        mol_type = protein
                        organism = Escherichia coli
```

```
SEQUENCE: 32
MNMLALTIIL PLIGFVLLAF SRGRWSENVS AIVGVGSVGL AALVTAFIGV DFFANGEQTY    60
SQPLWTWMSV GDFNIGFNLV LDGLSLTMLS VVTGVGFLIH MYASWYMRGE EGYSRFFAYT   120
NLFIASMVVL VLADNLLLMY LGWEGVGLCS YLLIGFYYTD PKNGAAAMKA FVVTRVGDVF   180
LAFALFILYN ELGTLNFREM VELAPAHFAD GNNMLMWATL MLLGGAVGKS AQLPLQTWLA   240
DAMAGPTPVS ALIHAATMVT AGVYLIARTH GLFLMTPEVL HLVGIVGAVT LLLAGFAALV   300
QTDIKRVLAY STMSQIGYMF LALGVQAWDA AIFHLMTHAF FKALLFLASG SVILACHHEQ   360
NIFKMGGLRK SIPLVYLCFL VGGAALSALP LVTAGFFSKD EILAGAMANG HINLMVAGLV   420
GAFMTSLYTF RMIFIVFHGK EQIHAHAVKG VTHSLPLIVL LILSTFVGAL IVPPLQGVLP   480
QTTELAHGSM LTLEITSGVV AVVGILLAAW LWLGKRTLVT SIANSAPGRL LGTWWYNAWG   540
FDWLYDKVFV KPFLGIAWLL KRDPLNSMMN IPAVLSRFAG KGLLLSENGY LRWYVASMSI   600
GAVVVLALLM VLR                                                     613

SEQ ID NO: 33        moltype = AA  length = 509
FEATURE              Location/Qualifiers
source               1..509
                     mol_type = protein
                     organism = Escherichia coli
SEQUENCE: 33
MLLPWLILIP FIGGFLCWQT ERFGVKVPRW IALITMGLTL ALSLQLWLQG GYSLTQSAGI    60
PQWQSEFDMP WIPRFGISIH LAIDGLSLLM VVLTGLLGVL AVLCSWKEIE KYQGFFHLNL   120
MWILGGVIGV FLAIDMFLFF FFWEMMLVPM YFLIALWGHK ASDGKTRITA ATKFFIYTQA   180
SGLVMLIAIL ALVFVHYNAT GVWTFNYEEL LNTPMSSGVE YLLMLGFFIA FAVKMPVVPL   240
HGWLPDAHSQ APTAGSVDLA GILLKTAAYG LLRFSLPLFP NASAEFAPIA MWLGVIGIFY   300
GAWMAFAQTD IKRLIAYTSV SHMGFVLIAI YTGSQLAYQG AVIQMIAHGL SAAGLFILCG   360
QLYERIHTRD MRMMGGLWSK MKWLPALSLF FAVATLGMPG TGNFVGEFMI LFGSFQVVPV   420
ITVISTFGLV FASVYSLAML HRAYFGKAKS QIASQELPGM SLRELFMILL LVVLLVLLGF   480
YPQPILDTSH SAIGNIQQWF VNSVTTTRP                                    509

SEQ ID NO: 34        moltype = AA  length = 485
FEATURE              Location/Qualifiers
source               1..485
                     mol_type = protein
                     organism = Escherichia coli
SEQUENCE: 34
MTITPQNLIA LLPLLIVGLT VVVVMLSIAW RRNHFLNATL SVIGLNAALV SLWFVGQAGA    60
MDVTPLMRVD GFAMLYTGLV LLASLATCTF AYPWLEGYND NKDEFYLLVL IAALGGILLA   120
NANHLASLFL GIELISLPLF GLVGYAFRQK RSLEASIKYT ILSAAASSFL LFGMALVYAQ   180
SGDLSFVALG KNLGDGMLNE PLLLAGFGLM IVGLGFKLSL VPFHLWTPDV YQGAPAPVST   240
FLATASKIAI FGVVMRLFLY APVGDSEAIR VVLAIIAFAS IIFGNLMALS QTNIKRLLGY   300
SSISHLGYLL VALIALQTGE MSMEAVGVYL AGYLFSSLGA FGVVSLMSSP YRGPDADSLF   360
SYRGLFWHRP ILAAVMTVMM LSLAGIPMTL GFIGKFYVLA VGVQAHLWWL VGAVVVGSAI   420
GLYYYLRVAV SLYLHAPEQP GRDAPSNWQY SAGGIVVLIS ALLVLVLGVW PQPLISIVRL   480
AMPLM                                                              485
```

What is claimed is:

1. A method or means for converting light energy and water into oxygen and reduced NADH, NADPH, or analogues thereof using artificial photosynthesis in an artificial cell free system, the method comprising:
   (a) providing an artificial cell free organelle system comprising:
      a membrane having two sides comprising an inner surface in contact with an inner aqueous medium and an outer surface in contact with an outer aqueous medium;
      one or more photosynthetic proteins comprising photosystem II or bacteriorhodopsin vectorially embedded within and traversing the membrane;
      one or more oxidoreductase proteins comprising Respiratory Complex I vectorially embedded within and traversing the membrane;
      ubiquinone or an analogue thereof;
      $NAD^+$, $NADP^+$ or an analogue thereof;
      water, and
      a photon energy source;
   (b) directing one or more photons to the one or more photosynthetic proteins;
   (c) the one or more photosynthetic proteins catalyzes the electron transfer from photon energy to ubiquinone or an analogue thereof, generating ubiquinol or an analogue thereof; and
   (d) the one or more oxidoreductase proteins catalyzes the electron transfer from ubiquinol or an analogue thereof to $NAD^+$, $NADP^+$, or analogues thereof, producing NADH, NADPH, or analogues thereof, and oxidizing ubiquinol or analogue thereof to ubiquinone or an analogue thereof.

2. The method of claim 1, wherein:
   when one or more photons are directed on the one or more photosynthetic proteins, the photosynthetic proteins harvest the photon energy and catalyze the oxidation of at least one water molecule in the inner aqueous medium, generating 0.5 equivalents of oxygen gas and yielding up to two protons and two electrons per two photons that are transferred to ubiquinone or an analogue thereof, generating ubiquinol or an analogue thereof;
   the accumulation of protons in the inner aqueous medium generates a proton concentration gradient between the inner aqueous medium and the outer aqueous medium; and
   the oxidoreductase enzyme comprising Respiratory Complex I pumps protons from the inner aqueous medium through the membrane to the outer aqueous medium to reduce the proton concentration gradient and simultaneously catalyzes the transfer of electrons from ubiquinol or an analogue thereof to NAD+, NADP+, or analogues thereof, producing NADH, NADPH, or analogues thereof, and oxidizing ubiquinol or analogue thereof back to ubiquinone or an analogue thereof.

3. The method of claim 1, wherein the membrane comprises a biomimetic bilayer, a biomimetic three-dimensional bilayer, a unilamellar liposome, a planar membrane, or a membraneous polymer construct.

4. The method of claim 3, wherein the membraneous polymer construct comprises a triblock co-polymer membrane comprising varying lengths of poly(dimethylsiloxane) (PDMS) as the hydrophobic membrane-forming block and poly(2-methyloxazoline) (PMOXA) as the hydrophilic membrane-forming block.

5. The method of claim 1, wherein the membrane comprises a closed unilamellar liposome comprising a phospholipid bilayer.

6. The method of claim 1, wherein the one or more photosynthetic proteins and one or more oxidoreductase proteins are vectorially embedded in the membrane using a detergent.

7. The method of claim 6, wherein the detergent comprises one or more of CHAPS (3-[(3-cholamidopropyl) dimethylammonio]-1-propanesulfonate), DDM (n-dodecyl-β-D-maltoside), OG (octyl-β-D-glucopyranoside), or Triton X-100.

8. The method of claim 1, wherein the photosystem II complex of proteins comprises the photosystem II complexes from *Cyanobacterium synechocystis, Synechococcus elongates, The rmosynechococcus elongatus, The rmosynechococcus vulcans, Pisum sativum, Chlamydomonas reihhardtii, Spinacia oleracea*, or *Arabidopsis thaliana*; and
the bacteriorhodopsin comprises the bacteriorhodopsin from *Halobacterium salinarum*.

9. The method of claim 1, wherein photosystem II complex of proteins or bacteriorhodopsin are purified or recombinant.

10. The method of claim 1, wherein the one or more photosynthetic proteins comprise the photosystem II complex of proteins from *Cyanobacterium synechocystis*.

11. The method of claim 1, wherein the Respiratory Complex I complex of proteins comprises the Respiratory Complex I of *Eschericia coli, Thermus thermophilus, Vibrio cholerae, Yarrowia lipolytica, Ovis aries, Bos taurus, Mus musculus*, or *Homo sapiens*.

12. The method of claim 11, wherein the Respiratory Complex I complex of proteins are purified or recombinant.

13. The method of claim 1, wherein the one or more oxidoreductase enzymes comprises the Respiratory Complex I complex of proteins from *E. coli*.

14. The method of claim 1, wherein the one or more oxidoreductase enzymes comprises a Respiratory Complex I that has been engineered to preferentially reduce NADPH or an analogue thereof.

15. The method of claim 1, wherein the one or more oxidoreductase enzymes are vectorially incorporated into the membrane in an orientation opposite to the orientation of the oxidoreductase enzyme in vivo.

16. The method of claim 1, wherein the ubiquinone analogue has the structure:

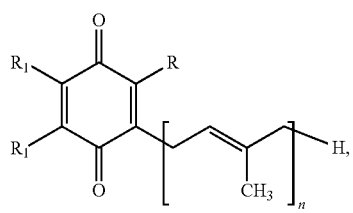

wherein R is methyl, hydroxyl, or hydrogen and $R_1$ is independently methoxy, methyl, hydroxyl or hydrogen, and n is an integer between 0 to 20, 6 to 12, or 7 to 10, including all integers within the specified ranges.

17. The method of claim 1, wherein the $NAD^+$ or $NADP^+$ analogue has the structure:

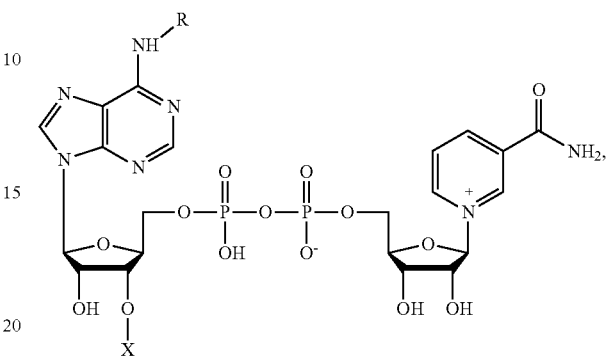

where R is a polyethylene glycol of 100 to 10,000 MW, a carbohydrate moiety or a polypeptide, and X is phosphate or hydrogen.

18. The method of claim 1, wherein the ubiquinol analogue has the structure:

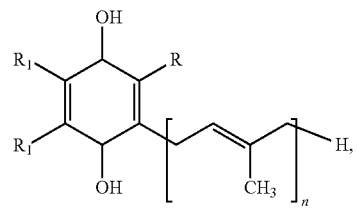

wherein R is methyl, hydroxyl, or hydrogen and $R_1$ is independently methoxy, methyl, hydroxyl or hydrogen, and n is an integer between 0 to 20, 6 to 12, or 7 to 10, including all integers within the specified ranges.

19. The method of claim 1, wherein the NADH or NADPH analogue has the structure:

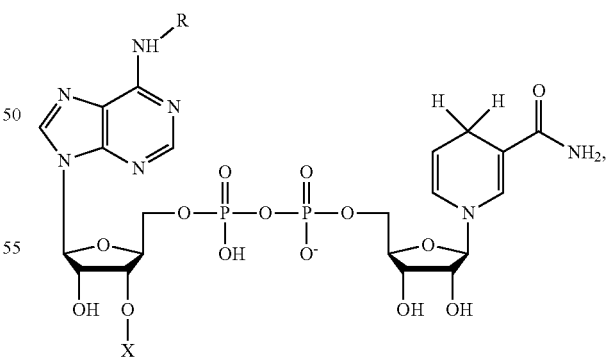

where R is a polyethylene glycol of 100 to 10,000 MW, a carbohydrate moiety, or a polypeptide, and X is phosphate or hydrogen.

20. The method of claim 1, further comprising adding an ionophore comprising one or more of valinomycin, salinomycin, lasalocid, ionomycin, nonactin, beauvericin, or calcimycin.

21. The method of claim 1, further comprising adding an ionophore comprising a potassium ionophore, and wherein the potassium ionophore comprises valinomycin or salinomycin.

* * * * *